United States Patent
Fan et al.

(10) Patent No.: US 12,297,417 B2
(45) Date of Patent: May 13, 2025

(54) LATERAL FILTER ARRAY MICROFLUIDIC DEVICE

(71) Applicant: UNIVERSITY OF FLORIDA RESEARCH FOUNDATION, INCORPORATED, Gainesville, FL (US)

(72) Inventors: Zhonghui Hugh Fan, Gainesville, FL (US); Kangfu Chen, Gainesville, FL (US)

(73) Assignee: UNIVERSITY OF FLORIDA RESEARCH FOUNDATION, INCORPORATED, Orlando, FL (US)

( * ) Notice: Subject to any disclaimer, the term of this patent is extended or adjusted under 35 U.S.C. 154(b) by 968 days.

(21) Appl. No.: 17/270,167

(22) PCT Filed: Aug. 21, 2019

(86) PCT No.: PCT/US2019/047505
§ 371 (c)(1),
(2) Date: Feb. 22, 2021

(87) PCT Pub. No.: WO2020/041471
PCT Pub. Date: Feb. 27, 2020

(65) Prior Publication Data
US 2021/0236992 A1 Aug. 5, 2021

Related U.S. Application Data

(60) Provisional application No. 62/720,592, filed on Aug. 21, 2018.

(51) Int. Cl.
*B01D 61/14* (2006.01)
*B01D 61/18* (2006.01)
(Continued)

(52) U.S. Cl.
CPC .......... *C12M 33/14* (2013.01); *B01D 61/147* (2013.01); *B01D 61/18* (2013.01); *B01D 63/005* (2013.01);
(Continued)

(58) Field of Classification Search
CPC ...... C12M 33/14; C12M 23/14; C12M 23/16; C12M 25/10; C12M 47/04; B01D 61/147;
(Continued)

(56) References Cited

U.S. PATENT DOCUMENTS

| 5,646,001 A | 7/1997 | Terstappen et al. |
| 5,726,026 A | 3/1998 | Wilding et al. |

(Continued)

FOREIGN PATENT DOCUMENTS

| WO | 2013044240 | 3/2013 |
| WO | 2020041471 A1 | 2/2020 |

OTHER PUBLICATIONS

Adams, Andre' A. et al., "Highly efficient circulating tumor cell isolation from whole blood and label-free enumeration using polymer-based microfluidics with an integrated conductivity sensor," J. Am. Chem. Soc. vol 130, pp. 8633-8641, 2008.

(Continued)

*Primary Examiner* — Jill A Warden
*Assistant Examiner* — Michael Stanley Gzybowski
(74) *Attorney, Agent, or Firm* — Timothy H. Van Dyke; Wolter Van Dyke Davis, PLLC

(57) ABSTRACT

A lateral filter array microfluidic (LFAM) device for highly efficient immunoaffinity isolation of target cells from a population of cells. The LFAM device may include of one or more serpentine main channels incorporated with lateral filter arrays. Antibodies are immobilized on the channel surface including the lateral filters and are capable of specific binding to one or more biomolecules on the surface of (Continued)

the target cell. The device may include one or more arrays of lateral filters with different sizes. The overall filters sizes are close to the diameter of the target cell, therefore the interaction between biomarkers on the target cells and corresponding antibodies immobilized on the filter surface is largely strengthened due to the direct contact between target cells and lateral filters. Methods include flowing a population of cells through an antibody-coated LFAM device for target cells capture, followed by washing the device to remove non-specific captured cells.

26 Claims, 40 Drawing Sheets

(51) Int. Cl.
*B01D 63/00* (2006.01)
*C12M 1/00* (2006.01)
*C12M 1/12* (2006.01)
*C12M 1/26* (2006.01)
*C12M 3/06* (2006.01)
*G01N 33/543* (2006.01)
*G01N 33/574* (2006.01)

(52) U.S. Cl.
CPC ............ *C12M 23/14* (2013.01); *C12M 23/16* (2013.01); *C12M 25/10* (2013.01); *C12M 47/04* (2013.01); *G01N 33/54366* (2013.01); *G01N 33/57492* (2013.01); *B01D 2313/08* (2013.01); *B01D 2313/40* (2013.01)

(58) Field of Classification Search
CPC ................ B01D 61/18; B01D 2313/08; B01D 2313/40; G01N 33/54366; G01N 33/558; G01N 33/57492
See application file for complete search history.

(56) References Cited

U.S. PATENT DOCUMENTS

| | | | |
|---|---|---|---|
| 6,632,655 | B1 | 10/2003 | Mehta et al. |
| 9,957,472 | B2* | 5/2018 | Chung .................. C12M 23/16 |
| 2003/0087265 | A1 | 5/2003 | Sauter et al. |
| 2006/0140871 | A1 | 6/2006 | Sillerud |
| 2006/0147941 | A1 | 7/2006 | Su |
| 2008/0020368 | A1 | 1/2008 | Yang et al. |
| 2009/0298067 | A1 | 12/2009 | Irimia et al. |
| 2010/0105053 | A1 | 4/2010 | Cho et al. |
| 2010/0123457 | A1 | 5/2010 | Shinoda |
| 2010/0323388 | A1 | 12/2010 | Chiu et al. |
| 2011/0070581 | A1 | 3/2011 | Gupta et al. |
| 2011/0158901 | A1 | 6/2011 | Santra |
| 2012/0070833 | A1 | 3/2012 | Wang et al. |
| 2012/0077246 | A1 | 3/2012 | Hong et al. |
| 2012/0100521 | A1 | 4/2012 | Soper et al. |
| 2013/0035630 | A1 | 2/2013 | Chen |
| 2013/0190212 | A1* | 7/2013 | Handique ......... B01L 3/502746 506/40 |
| 2015/0056614 | A1* | 2/2015 | Mikolajczyk .... G01N 33/57415 435/6.12 |
| 2016/0262934 | A1* | 9/2016 | Siegele ............... A61F 9/00827 |
| 2016/0279637 | A1 | 9/2016 | Sarioglu et al. |

OTHER PUBLICATIONS

Allard, W. Jeffery et al., "Tumor cells circulate in the peripheral blood of all major carcinomas but not in healthy subjects or patients with nonmalignant diseases," Clinical Cancer Research, vol. 10, pp. 6897-6904, Oct. 15, 2004.

Arya, Sunil K. et al., "Enrichment, detection and clinical significance of circulating tumor cells," Lab Chip, 2013, vol. 13, p. 1995-2027.
Bruus, Henrik, "Acoustofluidics 1: Governing equations in microfluidics," Lab on a Chip, 11(22), 3742-3751, 2011.
Capretto, Lorenzo et al., "Micromixing within microfluidic devices," Top Curr. Chem. 2011, vol. 304, pp. 27-68.
Carpenter, Ann E. et al., "CellProfiler: image analysis software for identifying and quantifying cell phenotypes," Genome Biology, 2006, 7:R100, vol. 7, issue 10, 11 pages.
Cen, Putao et al., "Circulating tumor cells in the diagnosis and management of pancreatic cancer," Biochimica et Biophysica Acta, 1826 (2012) 350-356.
Chen, Kangfu et al., "Integration of lateral filter arrays with immunoaffinity for circulating-tumor-cell isolation," Angew. Chem. Int. Ed. 2019, 58, 7606-7610.
Chen, Jian et al., "Microfluidic approaches for cancer cell detection, characterization, and separation," Lab Chip, 2012, 12, 1753-1767.
Chen, Li et al., "Aptamer-mediated efficient capture and release of T Lymphocytes on nanostructured surfaces," Adv. Mater., 2011, 23, 4376-4380.
Chen, Weiqiang et al., "Nanoroughened surfaces for efficient capture of circulating tumor cells without using capture antibodies," AcsNano, vol. 7, No. 1, pp. 566-575, 2013.
Chen, Kangfu et al., "Incorporation of lateral microfiltration with immunoaffinity for enhancing the capture efficiency of rare cells," Scientific Reports, (2010) 10:14210, 12 pages.
Chiu, Yun-Yen et al., "Enhancement of microfluidic particle separation using cross-flow filters with hydrodynamic focusing," Biomicrofluidics 10, 011906 (2016).
Dharmasiri, Udara et al., "Microsystems for the capture of low-abundance cells," Annual Review of Analytical Chemistry, vol. 3, 2010, pp. 409-432.
Dharmasiri, Udara et al., "High-throughout selection, enumeration, electrokinetic manipulation, and molecular profiling of low-abundance circulating tumor cells using a microfluidic system," Anal. Chem. 2011, 83, 2301-2309.
Dokukin, Maxim E. et al., "Quanitative study of the elastic modulus of loosely attached cells in AFM indentation experiments," Biophysical Journal, vol. 104, May 2013, pp. 2123-2131.
Forbes, Thomas P. et al., "Engineering and analysis of surface interactions in a microfluidic herringbone micromixer," Lab Chip, 2012, 12, pp. 2634-2637.
Gleghorn, Jason P. et al., "Capture of circulating tumor cells from whole blood of prostate cancer patients using geometrically enhanced differential immunpcapture (GEDI) and prostate-specific antibody," Lab Chip, 2010, 10, 27-29.
Guo, Junming PhD. et al., "Detecting carcinoma cells in peripheral blood of patients with hepatocellular carcinoma by Immunomagnetic beads and RT-PCR," J. Clin Gastroenterol, vol. 41, No. 8, Sep. 2007, pp. 783-788.
Han, Woojin et al., "Nanoparticle coatings for enhanced capture of flowing cells in microtubes," AcsNano, vol. 4, No. 1, pp. 174-180.
He, Wei et al., "In vivo quanitation of rare circulating tumor cells by multiphoton intravital flow cytometry," PNAS, Jul. 10, 2007, vol. 104, No. 28, pp. 11760-11765.
Helo, Pauliina et al., "Circulating prostate tumor cells detected by reverse transcription-PCR in men with localized or castration-refractory prostate cancer: Concordance with CellSearch assay and association with bone metastases and with survival," Clinical Chemistry, 2009, 765-773.
Hoshino, Kazunori et al., "Microchip-based immunomagnetic detection of circulating tumor cells," Lab Chip, 2011, 11, 3449-3457.
Hu, Shuhuan et al., "Multiparametric biomechanical and biochemical phenotypic profiling of single cancer cells using an elasticity microcytometer," Small, 2016, 12, No. 17, pp. 2300-2311.
Huang, Yu-Fen et al., "Cancer cell targeting using multiple aptamers conjugated on nanorods," Anal. Chem. 2008, 80, 567-572.
Hurst, Sarah J., "Biomedical Nanotechnology: Methods in molecular biology," Human Press, 2011, pp. 140-150.
Issadore, David et al., "Ultrasensitive clinical enumeration of rare calls ex vivo using a u-Hall detector," Sci. Transl. Med., Jul. 4, 2012; 4(141), 22 pages.

(56) References Cited

OTHER PUBLICATIONS

Jiao, P.F. et al., "Cancer-targeting multifunctionalized gold nanoparticles in imaging and therapy," Current Medicinal Chemistry, 2011, 18, 2086-2102.

Kang, Joo H. et al., "A combined micromagnetic-microfluidic device for rapid capture and culture of rare circulating tumor cells," Lab Chip, 2012, 12, 2175-2181.

Karabacak, Nezihi Murat et al., "Microfluidic, marker-free isolation of circulating tumor cells from blood samples," Nat Protoc., Mar. 2014; 9(3): 694-710.

Khoja, L. et al., "A pilot study to explore circulating tumor cells in pancreatic cancer as a novel biomarker," British Journal of Cancer, (2012) 106, 508-516.

Kirpotin, Dmitri B. et al., "Antibody Targeting of Long-Circulating Lipidic Nanoparticles Does Not Increase Tumor Localization but Does Increase Internalization in Animal Models," Cancer Res 2006; 66: (13). Jul. 1, 2006, pp. 6732-6740.

Kotz, Kenneth T. et al., "Clinical microfluidics for neutrophil genomics and proteomics," Nature Medicine, vol. 16, No. 9, Sep. 2010, pp. 1042-1048.

Kuo, Jason S. et al., "Deformability considerations in filtration of biological cells," Lab Chip, 2010, 10, 837-842.

Lee, Sang-Kwon et al., "Nanowire substrate-based laser scanning cytometry for quantitation of circulating tumor cells," Nano Lett., Jun. 13, 2012; 12(6): 2697-2704.

Lin, Yu-Li et al., "Compression and deformation of soft spherical particles," Chemical Engineering Science, 63, (2008) 195-203.

Lustberg, Maryam et al., "Emerging technologies for CTC detection based on depletion of normal cells," in Minimal Residual Disease and circulating Tumor Cells in Breast Cancer, recent Results in Cancer Research, eds M. Ignatiadis et al., 2012, 97-110, vol. 195.

Maheswann, Shyamala et al., "Detection of mutations in EGFR in circulating lung cancer cells," The New England Journal of Medicine, 2008, 359, 366-377.

Meunier, Anne et al., "Combination of mechanical and molecular filtration for enhanced enrichment of circulating tumor cells," Anal. Chem., 2016, 88, 8510-8517.

Mikolajczyk, Stephen D. et al., "Detection of EpCAM-Negative and Cytokeratin-Negative Circulating Tumor Cells in Peripheral Blood," Journal of Oncology, vol. 2011, Article ID 252361, 10 pages, 2011.

Murlidhar, Vasudha, "A radial flow microfluidic device for ultra-high-throughput affinity-based isolation of circulating tumor cells," Small, Dec. 10, 2014; 10(23): 4897-4904.

Myung, Ja Hye et al., "Dendrimer-Mediated multivalent binding for the enhanced capture if tumor cells," Angew. Chem. Int. ed., 2011, 50, 11769-11772.

Nagrath, Sunitha et al., "Isolation of rare circulating tumor cells in cancer patients by microchip technology," Nature, Dec. 20, 2007; 450(7173): 1235-1239.

O'Donoghue, Meghan B. et al., "Single-molecule atomic force microscopy on live cells compares aptamer and antibody rupture forces," Anal Bioanal Chem (2012) 402:3205-3209.

Ozhumur, Emre et al., "Inertial focusing for tumor antigen-dependent and -independent sorting of rare circulating tumor cells," Sci Transl Med., Apr. 3, 2013; 5(179), 20 pages.

Pantel, K. et al., "Detection, clinical relevance and specific biological properties of disseminating tumor cells," Nature Reviews Cancer, vol. 8, May 2008, pp. 329-340.

Phillips, Joseph A. et al., "Enrichment of cancer cells using aptamers immobilized on a microfluidic channel," Anal. Chem., 2009, 81, 1033-1039.

Rice, AJ et al., "Matrix stiffness induces epithelial-mesenchymal transition and promotes chemoresistance in pancreatic cancer cells," Oncogenesis (2017) 6, e352, 9 pages.

Riethdorf, Sabine et al., "Detection of circulating tumor cells in peripheral blood of patients with metastatic breast cancer: A validation study of the cellSearch system," Clin Cancer Res., 2007:13(3) Feb. 1, 2007, pp. 920-928.

Saliba, Antoine-Emmanuel et al., "Microfluidic sorting and multimodal typing of cancer cells in self-assembled magnetic arrays," PNAS, Aug. 17, 2010, vol. 107, No. 33, pp. 14524-14529.

Schiro, Perry G. et al., "Sensitive and High-Throughput Isolation of Rare Cells from Peripheral Blood with Ensemble-Decision Aliquot Ranking," Angew Chem Int Ed Engl., May 7, 2012; 51(19): 4618-4622.

Shangguan, Dihua et al., "Aptamers evolved from live cells as effective molecular probes for cancer study," PNAS, Aug. 8, 2006, vol. 103, No. 32, pp. 11838-11843.

Sheng, Weian et al., "Aptamer-Enabled Efficient Isolation of Cancer Cells from Whole Blood Using Microfluidic Device," Anal. Chem. 2012, 84, 4199-4206.

Sheng, Weian et al., "Multivalent DNA Nanospheres for Enhanced Capture of Cancer Cells in Microfluidic Devices," AcsNano, vol. 7, No. 8, 7067-7076, 2013.

Sheng, Weian et al., "Capture, Release and Culture of Circulating Tumor Cells from Pancreatic Cancer Patients using an Enhanced Mixing Chip," Lab Chip, Jan. 7, 2014, 14(1): 89-98.

Sia, Samual K. et al., "Microfluific devices fabricated in poly(dimethylsiloxane) for biological studies," Electrophoresis, 2003, 24, 3563-3576.

Stott, Shannon L. et al., "Isolation of circulating tumor cells using a microvortex-generating herringbone-chip," PNAS, Oct. 26, 2010, vol. 107, No. 43, pp. 18392-18397.

Stroock, Abraham D. et al., "Chaotic Mixer for Microchannels," Science, vol. 295, Jan. 25, 2002, pp. 647-651.

Tang, Yadong et al., "Microfluidic device with integrated microfilter of conical-shaped holes for high efficiency and high purity capture of circulating tumor cells," Scientific Reports, 4:6052, 2014.

Tang, Zhiwen et al., "Selection of Aptamers for Molecular Recognition and Characterization of Cancer Cells," Anal. Chem., 2007, 79, 4900-4907.

Tjensvoll, Kjersti et al., "Circulating tumor cells in pancreatic cancer patients: Methods of detection and clinical Implications," Int. J. Cancer: 134, 1-8, 2014.

PCT/US2019/047505, Search Report and Written Opinion, Mailed date Dec. 20, 2019, 9 pages.

Valencia, Pedro M. et al., "Microfluidic technologies for accelerating the clinical translation of nanoparticles," Nat. Nanotechnol., Oct. 2012; 7(10):623-629.

Wang, Shutao et al., "Three-Dimentional Nanostructured Substrates towards Efficient Capture of Circulating Tumor Cells," Angew. Chem. Int. Ed., 2009, 48, 8970-8973.

Wang, Shutao et al., "Highly Efficient Capture of Circulating Tumor Cells by Using Nanostructured Silicon Substrates with Integrated Chaotic Micromixers," Angew. Chem. Int. Ed., 2011, 50, 3084-3088.

Xu, Lei et al., "Optimization and Evaluation of a Novel Size Based Circulating Tumor Cell Isolation System," PLOS ONE, Sep. 23, 2015, 23 pages.

Xu, Ye et al., "Aptamer-Based Microfluidic Device for Enrichment, Sorting, and Detection of Multiple Cancer Cells," Anal. Chem., 2009, 81, 7436-7442.

Yamamura, Shohei et al., "Accurate Detection of Carcinoma Cells by use of a Cell Microarray Chip," PLOS ONE, Mach 2012, vol. 7, issue 3, 9 pages.

Yoon, Yousang et al., "Clogging-free microfluidics for continuous size-based separation of microparticles," Scientific Reports, Sci. Rep., 6, 26531, 8 pages.

Yu, Min et al., "Circulating tumor cells: approaches to isolation and characterization," The Journal of Cell Biology, 2011, pp. 373-382, vol. 192, No. 3.

Zhang, Weijia et al., "Microfluidics separation reveals the stem-cell-like deformability of tumor-initiating cells," PNAS, Nov. 13, 2012, vol. 109, No. 46, pp. 18707-18712.

Zhao, Weian et al., "Bioinspired multivalent DNA network for capture and release of cells," PNAS, Nov. 27, 2012, vol. 109, No. 48, pp. 19626-19631.

Zhao, Mengxia et al., "An Automated High-Throughput Counting Method for Screening Circulating Tumor Cells in Peripheral Blood," Anal. Chem., 2013, 85, 2465-2471.

(56) References Cited

OTHER PUBLICATIONS

Zheng, Xiangjun et al., "A high-performance microsystem for isolating circulating tumor cells," Lab Chip, 2011, 11, 3269-3276.

Gashaw, Metages et al., "Isolation, Detection, and Antigen-Based Profiling of Circulating Tumor Cells Using a Size-Dictated Immunocapture Chip," Angew. Chem. Int. Ed., 2017, 56, 10681-10685.

McFaul, Sarah M. et al., "Cell separation based on size and deformability using microfluidic funnel ratchets," Lab Chip, 2012, 12, 2369-2376.

Moon, Hui-Sung et al., "Continuous separation of breast cancer cells from blood samples using multi-orifice flow fractionation (MOFF) and dielectrophoresis (DEP)," Lab Chip, 2011, 11, 1118-1125.

Thege, Fredrik I. et al., "Microfluidic immunocapture of circulating pancreatic cells using parrallel EpCAM and MUC1 capture: characterization, optimization and downstream ananlysis," Lab Chip, 2014, 14, 1775-1784.

Zhang, Nangang et al., "Electrospun TiO2 Nanofiber-Based Cell Capture Assay for Detecting Circulating Tumor Cells from Colorectal and Gastric Cancer Patients, " Adv. Mater., 2012, 24, 2756-2760.

Saliba, A-E. et al., "Microfluidic sorting and multimodal typing of cancer cells in self-assembled magnetic arrays," Proceedings of the National Academy of Sciences of the United States of America, Aug. 17, 2010, pp. 14524-14529, vol. 107, No. 33.

Wang, S. et al., "Nano "Fly Paper" Technology for the Capture of Circulating Tumor Cells" Methods in Molecular Biology, 2011, pp. 141-150, vol. 726, Cpt. 10.

Written Opinion in International Application No. PCT/US2014/066590, Feb. 19, 2015, pp. 1-9.

\* cited by examiner

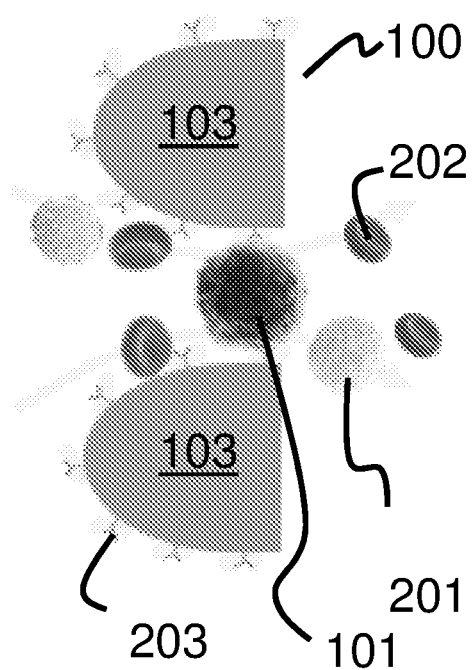 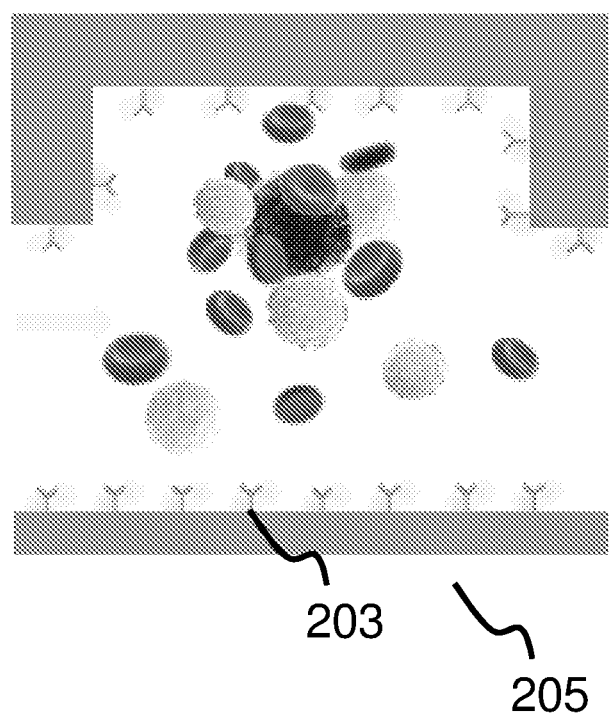
FIG. 2A  FIG. 2B

FIG. 6A
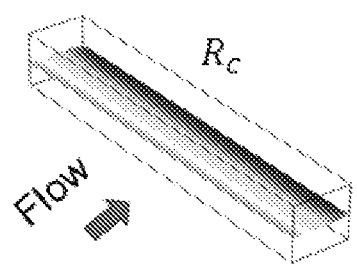
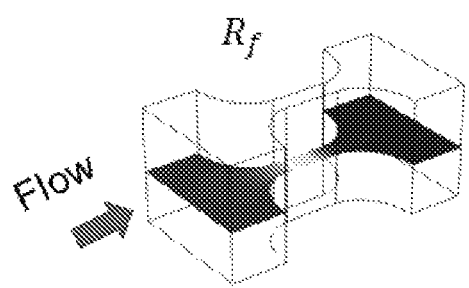
FIG. 6C
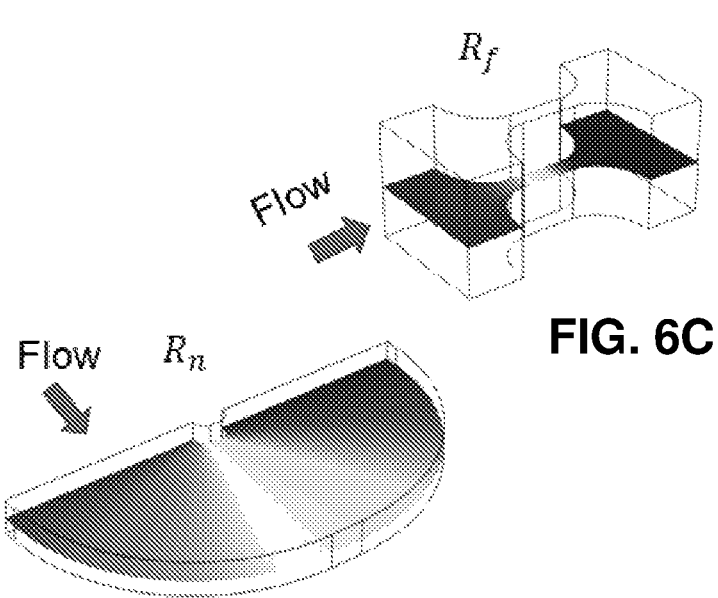
FIG. 6B

FIG. 7A  FIG. 7B  FIG. 7C  FIG. 7D
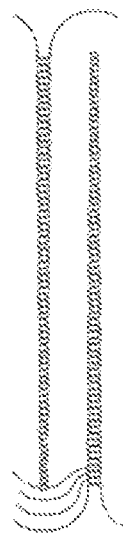 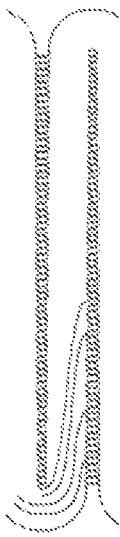 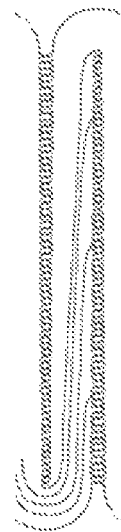 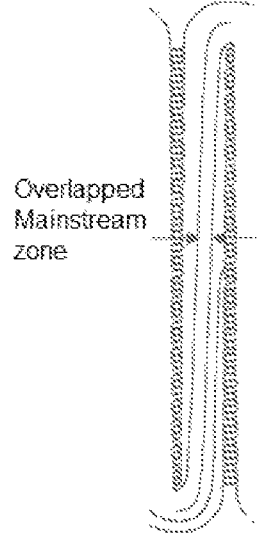
Overlapped Mainstream zone
Mainstream ratio <<50%   Mainstream ratio <50%   Mainstream ratio =50%   Mainstream ratio >50%
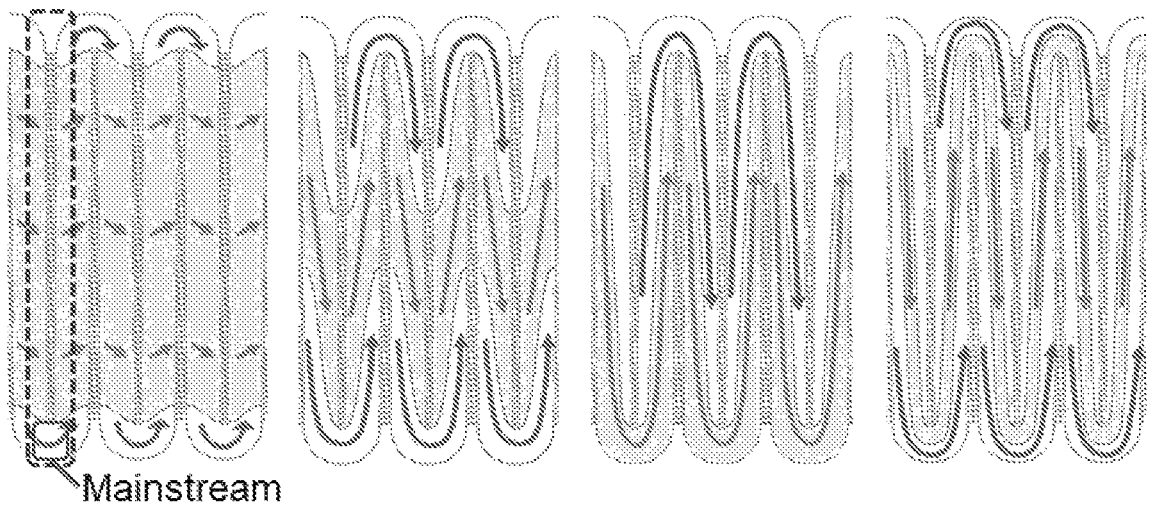
Total flow
Mainstream
FIG. 7E  FIG. 7F  FIG. 7G  FIG. 7H

FIG. 23A          FIG. 23B
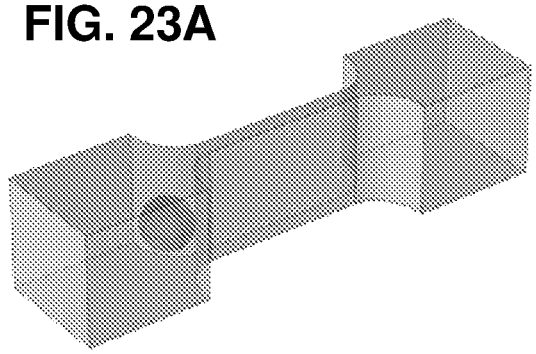
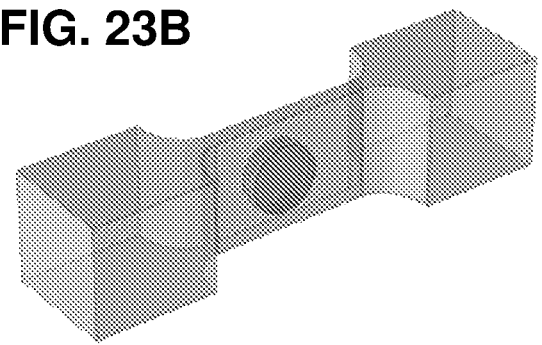
Velocity magnitude (mm/s)        Viscous stress (Pa)
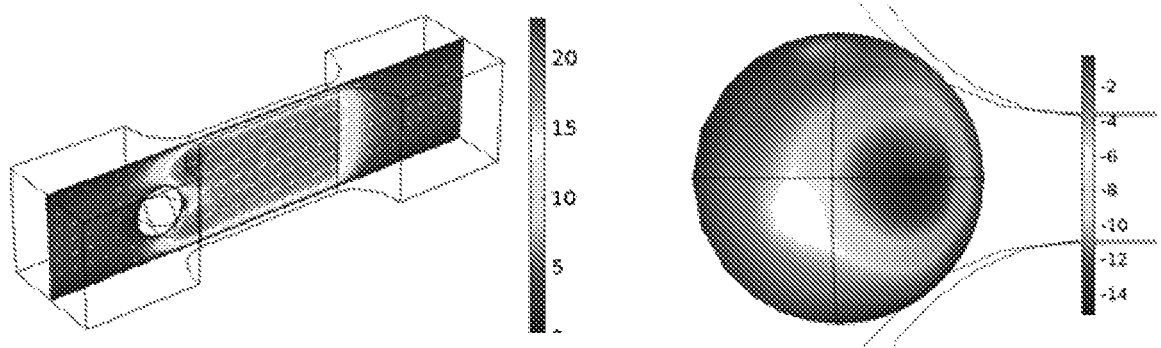
FIG. 23C          FIG. 23D
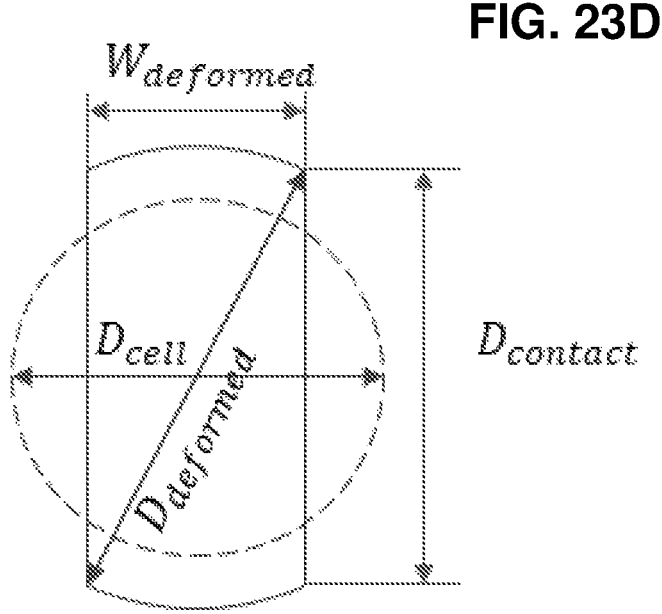
FIG. 23E

FIG. 27A     FIG. 27B     FIG. 27C
10-μm-filter     9-μm-filter     8-μm-filter
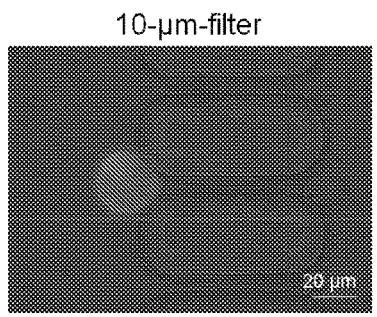 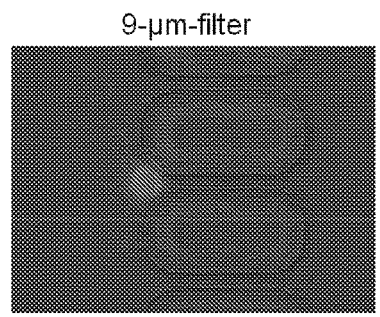 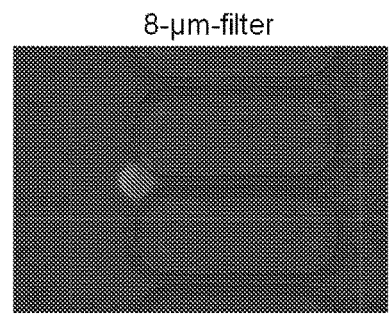
7-μm-filter     6-μm-filter
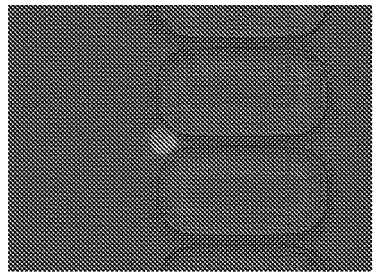 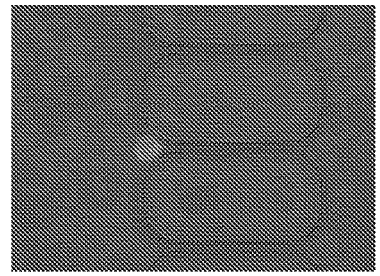
FIG. 27D     FIG. 27E

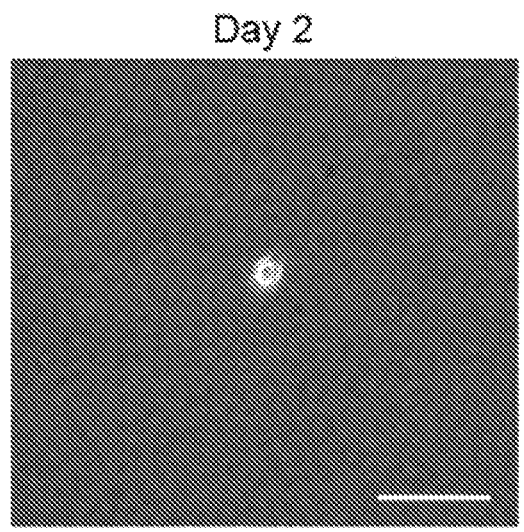
FIG. 30A Day 2
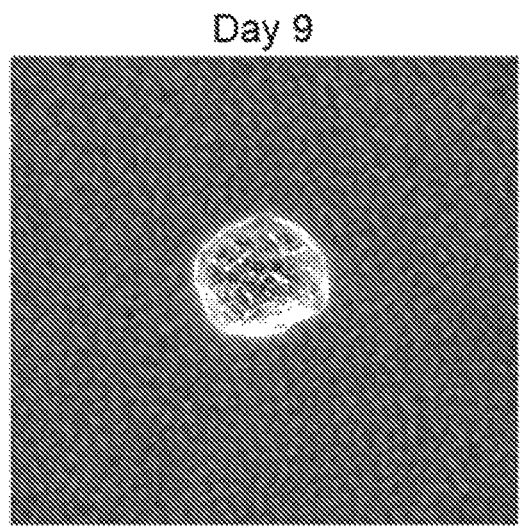
FIG. 30B Day 9
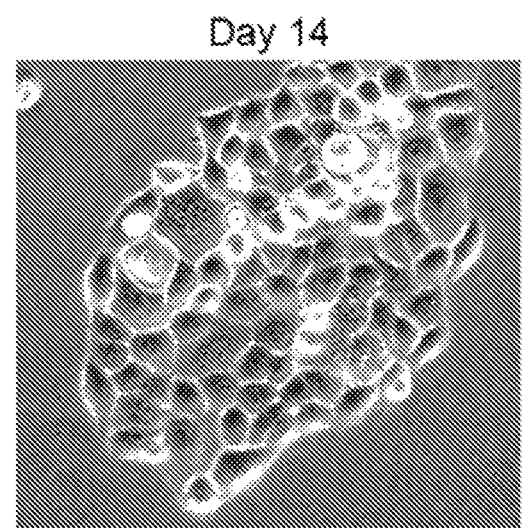
FIG. 30C Day 14

FIG. 37A
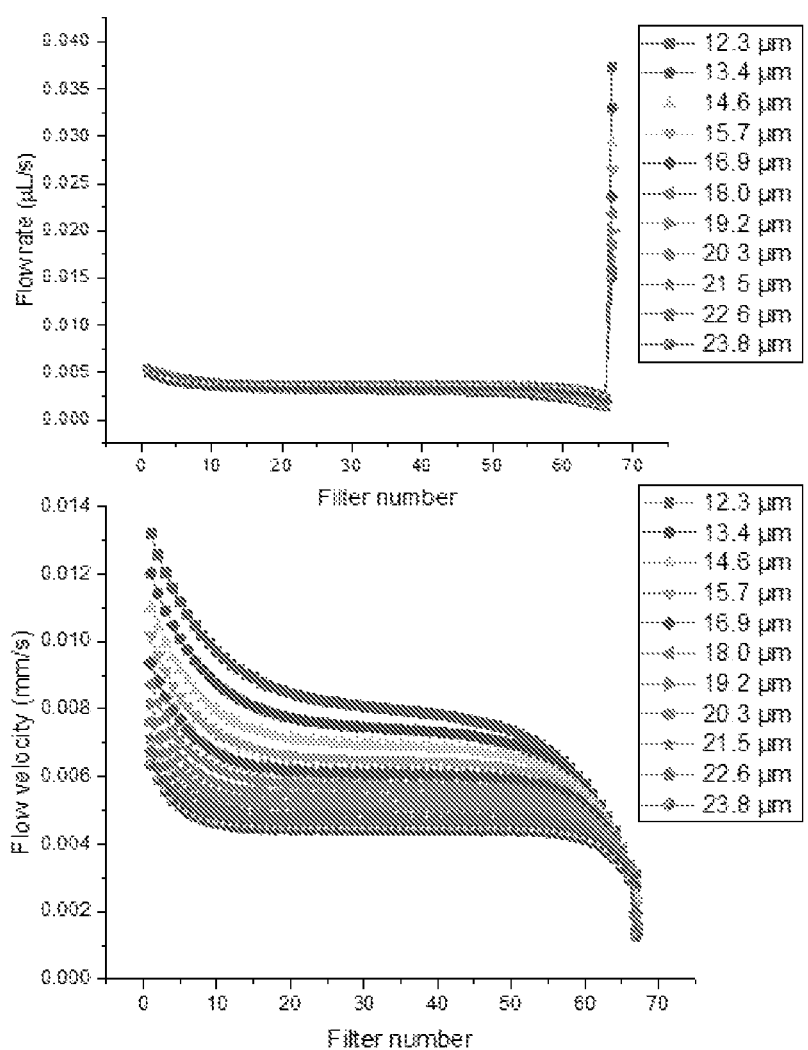
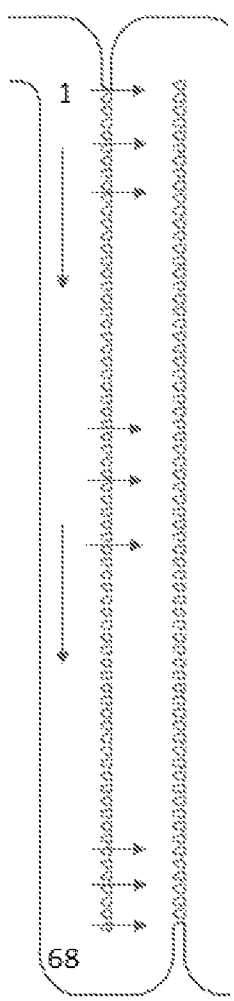
FIG. 37C  FIG. 37B

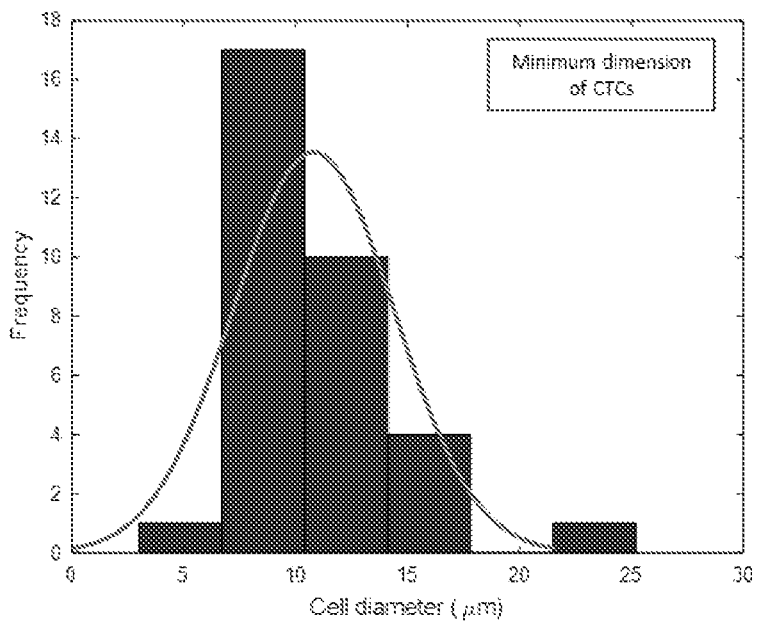
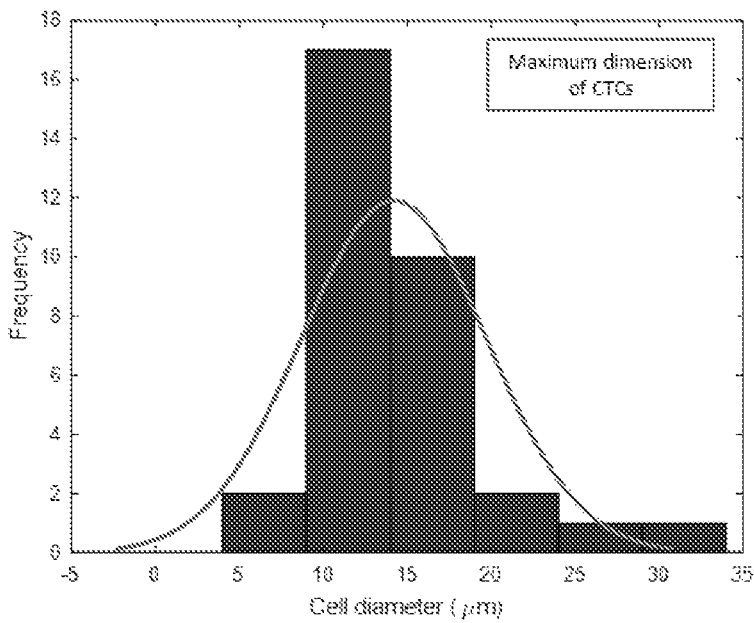
FIG. 39

LATERAL FILTER ARRAY MICROFLUIDIC DEVICE

CROSS-REFERENCE TO RELATED APPLICATION

This application claims the benefit of U.S. Provisional Patent Application No. 62/720,592, filed Aug. 21, 2018, titled LATERAL FILTER ARRAY MICROFLUIDIC DEVICE, which is incorporated by reference herein in its entirety.

STATEMENT REGARDING FEDERALLY SPONSORED RESEARCH OR DEVELOPMENT

This invention was made with government support under grant number K25 CA149080 awarded by the National Institutes of Health. The government has certain rights in the invention.

BACKGROUND

Circulating tumor cells (CTC) are cancer cells in the circulating system shredded from a primary tumor into peripheral blood. CTCs have been considered as important biomarkers for early detection of cancer metastasis, therapy monitoring and disease prognosis. Also, they offer insights into mechanisms of drug resistance. Compared with traditional biopsy which require tissue removal, the noninvasive 'liquid biopsy' using CTCs for cancer therapy may be potentially cheaper, less harmful to the patient, while keeping accuracy. However, the rarity of CTCs in the blood (tens of CTCs per mL blood) remains a technological barricade. The FDA-approved CellSearch® may be hindered by relatively low sensitivity and high cost. As comparison, different strategies based on microfluidics have been proposed which potentially leads to advanced technology for CTC isolation. The common methods for CTC enumeration are generally classified into two categories: physical-property-based separation and biological-property-based isolation. Physical property-based CTC isolation differentiate CTCs from other blood cells based on their physical properties such as size, deformity, electrophoretic properties, etc. Size may be one of the most prevalent physical properties used to differentiate CTCs from normal blood cells. Size-based CTC isolation assumes that CTCs are larger than most normal blood cells. Immunoaffinity-based CTC isolation relies on the specific conjugation between biomarkers on CTCs and antibodies immobilized in the microfluidic device. Immunoaffinity may be the primary biological property used to isolate CTCs because of the specific conjugation between surface biomarkers on CTCs (e.g., epithelial cell adhesion molecules or EpCAM) and antibodies immobilized on a solid surface. However, the heterogeneity of CTCs in both physical and biological properties makes such 'single-criterion' CTC isolation methods not universally applicable for clinical applications. For example, CTCs can have the similar size with white blood cells (WBCs), and some CTCs express little or no EpCAM (or other epithelial markers) due to epithelial-to-mesenchymal transition (EMT).

Combining size and immunoaffinity for CTC isolation has been explored by Juncker's group who used an antibody-functionalized membrane filter for tumor cell detection. Lee et al. enlarged the size of tumor cells by binding them with antibody-conjugated beads before filtration. However, membrane filters are limited by the pore size selected and possible cell clogging in the membrane can lower the cell purity (defined as the number of target cells captured over the number of all types of cells isolated). The short contact time between a tumor cell and a pore as well as only one contact opportunity limits the capture efficiency (defined as the number of target cells captured over the number of cells introduced). For binding tumor cells with antibody-conjugated beads, this sample treatment can cause cell fragmentation or loss as in the FDA-approved CellSearch assay.

On the other hand, the idea of integrating different CTC isolation approaches into a device seems more appealing. The development of integrated systems such as CTC i-chip [1], Size Dictated Immunocapture Chip (SDI-Chip) [2], MOFF-DEP separator[3] etc. shows the great potential of method integration for highly efficient CTC isolation. Nonetheless, challenges persist while some technologies require complicated sample pretreatment and others are limited by relatively low throughput. Developing a more user friendly, high-throughput, integrated device maintaining high capture efficiency and cell purity may be worth exploration.

BRIEF SUMMARY

Various embodiments relate to a lateral filter array microfluidic device for capturing a target isolate in a liquid sample. The device may include a substrate; and at least one series of boundaries associated with the substrate. The at least one series of boundaries may be arranged to define at least one serpentine main channel coupled with an inlet and an outlet that allows flow of the liquid sample in serpentine flow pattern. The at least one series of boundaries may include filters that allow lateral flow of the liquid sample relative to flow in the at least one serpentine main channel. The width of the at least one serpentine main channel may be greater than a filter size of the filters. The at least one serpentine main channel may have a width ranging from 3 µm to 1000 µm. The filter size may be from about 0.03 µm to about 100 µm. At least one boundary of the at least one series of boundaries may be formed by one or more filter support structures having a height ranging from 3 µm to 100 µm. At least one boundary of the at least one series of boundaries may be functionalized to include a binding molecule having an affinity to the target isolate. The binding molecule may include an antibody or aptamer or their combinations. The target isolate may be a cell or cell component, extracellular vesicle, virus, or particle. The cell may be a circulating tumor cell (CTC) or any of a variety of cells. The cell may be a rare cell. As used herein, the term rare cell refers to a cell not ordinarily found in a healthy subject. For example, a CTC cell may be a rare cell. Rare cells may include any cell that is either not present or is present in an undetectable or seldom detectable amount in a healthy subject. A healthy subject may be, for example, a person without a particular disease or with an average level of physical well-being as compared to the general population. The binding molecule may be attached to one or more filters. The binding molecule may be attached adjacent to a filter channel and on the channel walls of the device. At least one series of boundaries may include two or more series of boundaries that each defines a separate serpentine main channel. The series of boundaries may include a first boundary having filters of a first filter size and a second boundary having a filters of a second filter size. The first filter size and second filter size may be the same or different. The first boundary may be closer to the inlet and the second boundary may be closer to the outlet and wherein the first filter size may be greater than the second filter size. The lateral fluid microfluidic device may further include a third boundary having filters of a third filter size and a fourth boundary having filters of a fourth filter size. The third filter size may be smaller than the second filter size, and the fourth filter size may be smaller than the third filter size. The lateral fluid microfluidic device may further include a cover over the boundaries. The cover may be any suitable material, such as a glass slide. The substrate may be any suitable material such as polydimethylsiloxane (PDMS). The device may be made of or may include a thermoplastic material, silicon, glass, adhesive tapes, or any suitable combination thereof. The thermoplastic material may include cyclic olefin copolymer (COC), poly(methyl methacrylate) (PMMA), polycarbonate (PC), polystyrene, polyester, polypropylene, polyurethane, acrylonitrile butadiene styrene (ABS), polylactic acid (PLA), and polytetrafluoroethylene (PTFE).

Various embodiments relate to a method of capturing a target isolate in a liquid sample. The method may include applying the liquid sample to an inlet of a microfluidic device according any of the various embodiments described herein; and asserting a force to direct flow of the liquid sample along the serpentine main channel and laterally through filters in the series of boundaries, wherein the target isolate is captured at one or more of the filters. The filters may include a binding molecule having affinity for the target isolate. The binding molecule may be an antibody, or aptamer, or multiple antibodies, multiple aptamer, or their combination. The target isolate may be a particle, virus, exosome, extracellular vesicles, bacterium, cell or cell component. The cell may be a CTC.

These and other features, aspects, and advantages of various embodiments will become better understood with reference to the following description, figures, and claims.

BRIEF DESCRIPTION OF THE DRAWINGS

Certain embodiments are illustrated by way of example, and not by way of limitation, in the Figures of the accompanying drawings. Many aspects of this disclosure can be better understood with reference to the following figures, in which:

FIG. 2A: is an example according to various embodiments illustrating immunocapture of a circulating tumor cell 101 in the LFAM device 100;

FIG. 2B: is an example according to various embodiments illustrating a less-preferred affinity-based method of immunocapture in a microfluidic device 205;

FIG. 6A: is an example according to various embodiments illustrating a hydrodynamic resistance model within a channel component of a LFAM device;

FIG. 6B: is an example according to various embodiments illustrating a hydrodynamic resistance model within a bend component of a LFAM device;

FIG. 6C: is an example according to various embodiments illustrating a hydrodynamic resistance model within a lateral filter component of a LFAM device;

FIG. 7A: is an example according to various embodiments illustrating flow velocity along a mainstream flow channel of a LFAM device when the mainstream ratio is <<50%;

FIG. 7B: is an example according to various embodiments illustrating flow velocity along a mainstream flow channel of a LFAM device when the mainstream ratio is <50%;

FIG. 7C: is an example according to various embodiments illustrating flow velocity along a mainstream flow channel of a LFAM device when the mainstream ratio is =50%;

FIG. 7D: is an example according to various embodiments illustrating flow velocity along a mainstream flow channel of a LFAM device when the mainstream ratio is >50%;

FIG. 7E: is an example according to various embodiments illustrating a streamline pattern in an LFAM device with a mainstream ratio<<50%;

FIG. 7F: is an example according to various embodiments illustrating a streamline pattern in an LFAM device with a mainstream ratio<50%;

FIG. 7G: is an example according to various embodiments illustrating a streamline pattern in an LFAM device with a mainstream ratio=50%;

FIG. 7H: is an example according to various embodiments illustrating a streamline pattern in an LFAM device with a mainstream ratio>50%;

FIG. 23A: is an example according to various embodiments illustrating a CTC cell coming into contact with the filter without deformation;

FIG. 23B: is an example according to various embodiments illustrating a CTC cell fully compressed in the filter;

FIG. 23C: is an example according to various embodiments illustrating the hydrodynamic force a cell experiences near the entrance of a lateral filter;

FIG. 23D: is an example according to various embodiments illustrating the hydrodynamic force a cell experiences near the entrance of a lateral filter;

FIG. 23E: is an example according to various embodiments illustrating the deformation of the cell from the initial state to the fully deformed state;

FIG. 27A: is an example according to various embodiments illustrating an images of L3.6pl cells captured in a 10-μm-filter zone;

FIG. 27B: is an example according to various embodiments illustrating an images of L3.6pl cells captured in a 9-μm-filter zone;

FIG. 27C: is an example according to various embodiments illustrating an images of L3.6pl cells captured in a 8-μm-filter zone;

FIG. 27D: is an example according to various embodiments illustrating an images of L3.6pl cells captured in a 7-μm-filter zone;

FIG. 27E: is an example according to various embodiments illustrating an images of L3.6pl cells captured in a 6-μm-filter zone;

FIG. 30A: is an example according to various embodiments illustrating a photograph of a culture of L3.6pl cells on day 2 after release;

FIG. 30B: is an example according to various embodiments illustrating a photograph of a culture of L3.6pl cells on day 9 after release;

FIG. 30C: is an example according to various embodiments illustrating a photograph of a culture of L3.6pl cells on day 14 after release;

Figure 34:
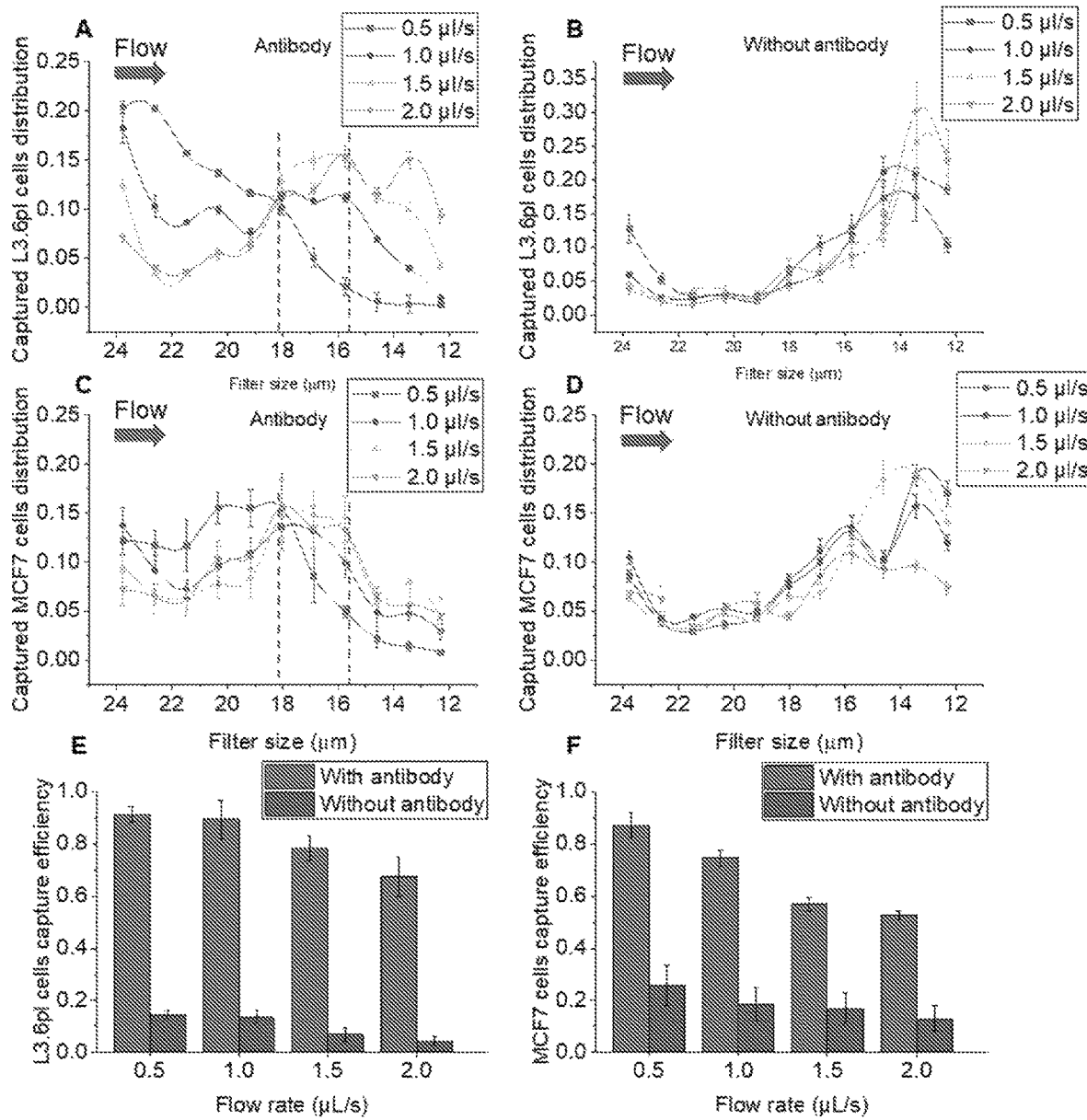
FIG. 34A: is an example according to various embodiments illustrating captured L3.6pl cell distribution in the LFAM device with antibody under different flow rates.
Figure 35:
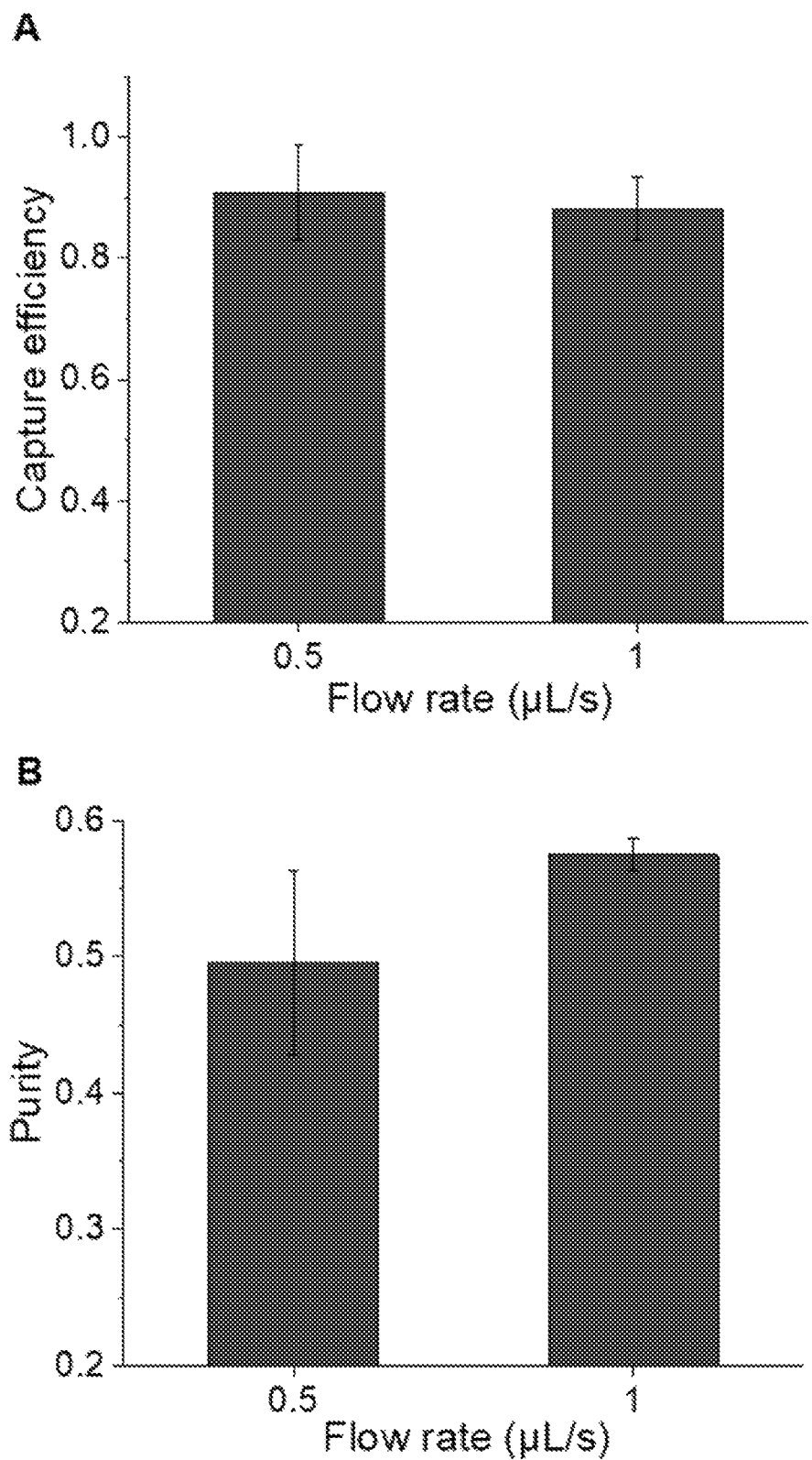
Figure 36:
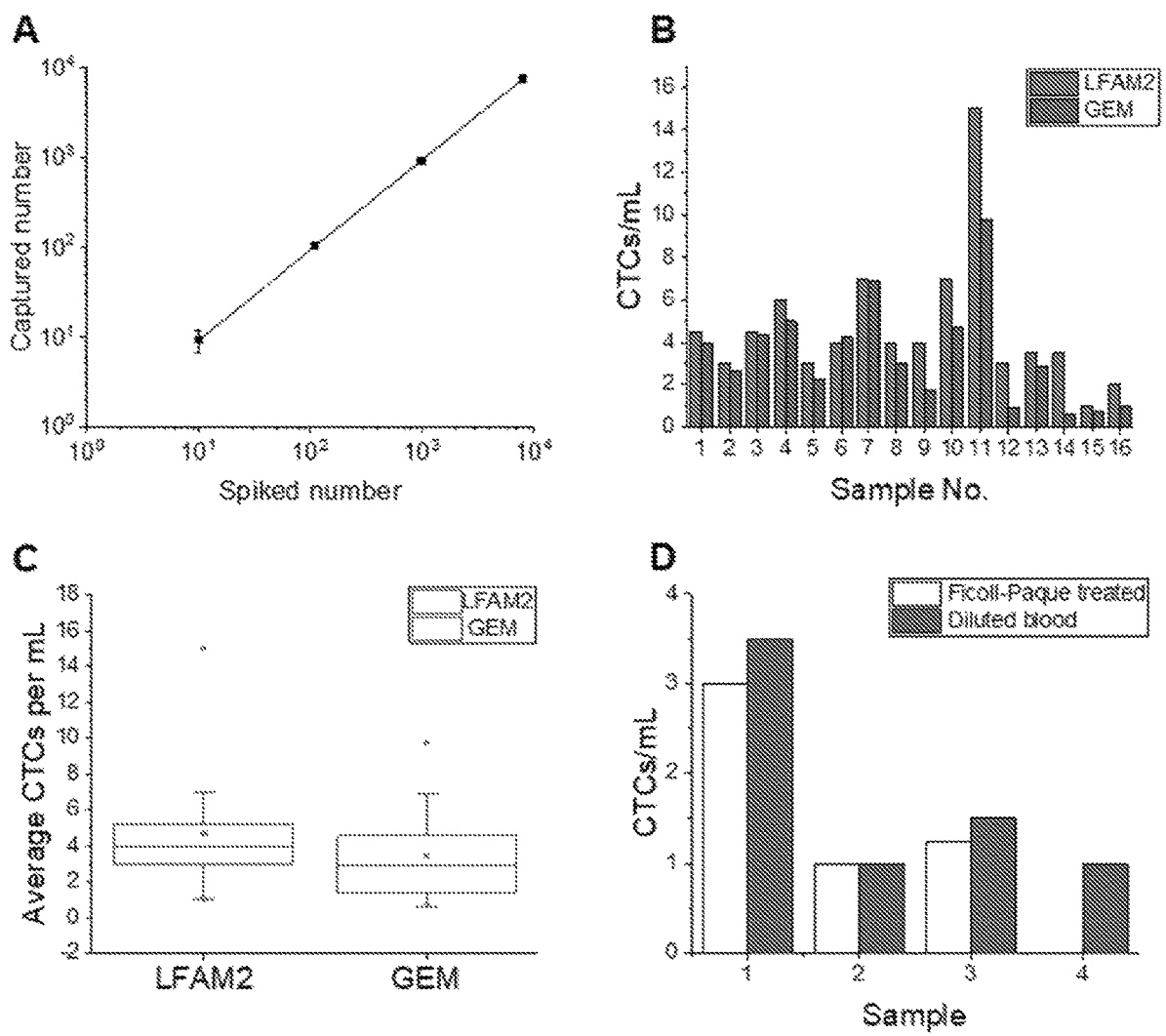

FIG. 34B: is an example according to various embodiments illustrating captured L3.6pl cell distribution in the LFAM device without antibody under different flow rates;

FIG. 34C: is an example according to various embodiments illustrating captured MCF7 cell distribution in the LFAM device with antibody under different flow rates;

FIG. 34D: is an example according to various embodiments illustrating captured MCF7 cell distribution in the LFAM device without antibody under different flow rates;

FIG. 34E: is an example according to various embodiments illustrating L3.6pl cells captured in the LFAM device under different flow rates;

FIG. 34F: is an example according to various embodiments illustrating MCF7 cells captured in the LFAM device under different flow rates;

FIG. 35A: is an example according to various embodiments illustrating capture efficiency of target L3.6pl cells in the antibody-functionalized LFAM device from a population of cells at 0.5 μL/s and 1 μL/s;

FIG. 35B: is an example according to various embodiments illustrating cell purity of target L3.6pl in the antibody-functionalized LFAM device at 0.5 μL/s and 1 μL/s;

FIG. 36A: is an example according to various embodiments illustrating capture of target cells from diluted blood. Different amount of L3.6pl cells are spiked in 1 mL of 2-time diluted blood sample and infused to the antibody functionalized LFAM device;

FIG. 36B: is an example according to various embodiments illustrating CTCs per mL enumerated from the LFAM device and GEM chip from 16 clinical samples;

FIG. 36C: is an example according to various embodiments illustrating the average CTCs per mL in the LFAM device and the GEM device;

FIG. 36D: is an example according to various embodiments illustrating a comparison of different blood pretreatment methods using LFAM;

FIG. 37A: is an example according to various embodiments illustrating a flow rate distribution in different filters in the same column as compared with flow rate in the channel elbow;

FIG. 37B: is an example according to various embodiments illustrating a flow velocity distribution in different filters in the same column as compared with flow velocity in the channel elbow;

FIG. 37C: is an example according to various embodiments illustrating a schematic diagram of the channel for which data is presented in FIG. 37A and FIG. 37B;

FIG. 38A: is an example according to various embodiments illustrating sample images of captured CTC (CK+/DAPI+/CD45−);

FIG. 38B: is an example according to various embodiments illustrating sample images of captured and nonspecific captured white blood cells (CK−/DAPI+/CD45+);

FIG. 39A: is an example according to various embodiments illustrating the distribution of minimum dimensions of CTCs measured by CellSens; and FIG. 39B: is an example according to various embodiments illustrating the distribution of maximum dimensions of CTCs measured by CellSens.

It should be understood that the various embodiments are not limited to the examples illustrated in the figures.

DETAILED DESCRIPTION

Various embodiments may be understood more readily by reference to the following detailed description. Unless defined otherwise, all technical and scientific terms used herein have the same meaning as commonly understood by one of ordinary skill in the art to which this disclosure belongs.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

Different from existed approaches, disclosed herein is a unique lateral filter array microfluidic (LFAM) device and uses thereof for rare cell (e.g. CTCs) capture. Embodiments described herein are capable of isolating, detecting and enumerating cells (e.g. CTCs) with high throughput and superb efficiency. Through combining filtration with immunoaffinity based capture, the LFAM device, according to various embodiments, may be able to isolate target material, including cells, extracellular vesicles, virus, or particles. In a specific aspect, CTCs are captured with low deformability or high biomarker expression level. Even more deformable CTCs with lower biomarker expression are likely to be captured if the two components combination exceeds the CTC capture threshold. While cells have been captured through using antibody-decorated membrane filters for CTC isolation [4], the implementation of the unique LFAM device improves the capture efficiency cells and better preserves their structural integrity.

In one embodiment, a lateral filter array microfluidic (LFAM) device is provided for capturing a target isolate in a liquid sample. The device may include a substrate; and at least one series of boundaries associated with the substrate, wherein the at least one series of boundaries are arranged to define at least one serpentine main channel coupled with an inlet and an outlet that allows flow of the liquid sample in serpentine flow pattern; and wherein the at least one series of boundaries comprise filters that allow lateral flow of the liquid sample relative to flow in the serpentine main microfluidic channel. In a specific embodiment, the lateral filter array microfluidic device comprises at least one boundary of the at least one series of boundaries that may be functionalized to comprise a binding molecule having an affinity to the target isolate. In one example, the binding molecule pertains to an antibody or aptamer or their combinations. In one example, the target isolate may be a cell or cell component, extracellular vesicle, virus, or particle. In a specific embodiment, the target isolate may be a circulating tumor cell.

In a further embodiment, provided is a method of capturing a target isolate in a liquid sample. The method involves applying the liquid sample to an inlet of a lateral flow microfluidic device as described herein; and asserting a force to direct flow of the liquid sample along the serpentine main channel and laterally through filters in the series of boundaries, wherein the target isolate may be captured at one or more of the filters.

Previous works mainly relied on antibody functionalized membrane filters which may have porosity problems and cause cell clogging, leading to low purity. Also, the shortness of contact time between cells and the membrane filter can diminish the effect of immunocapture. To avoid these problems, in-plane filters in the LFAM device were used.

Figure 1:
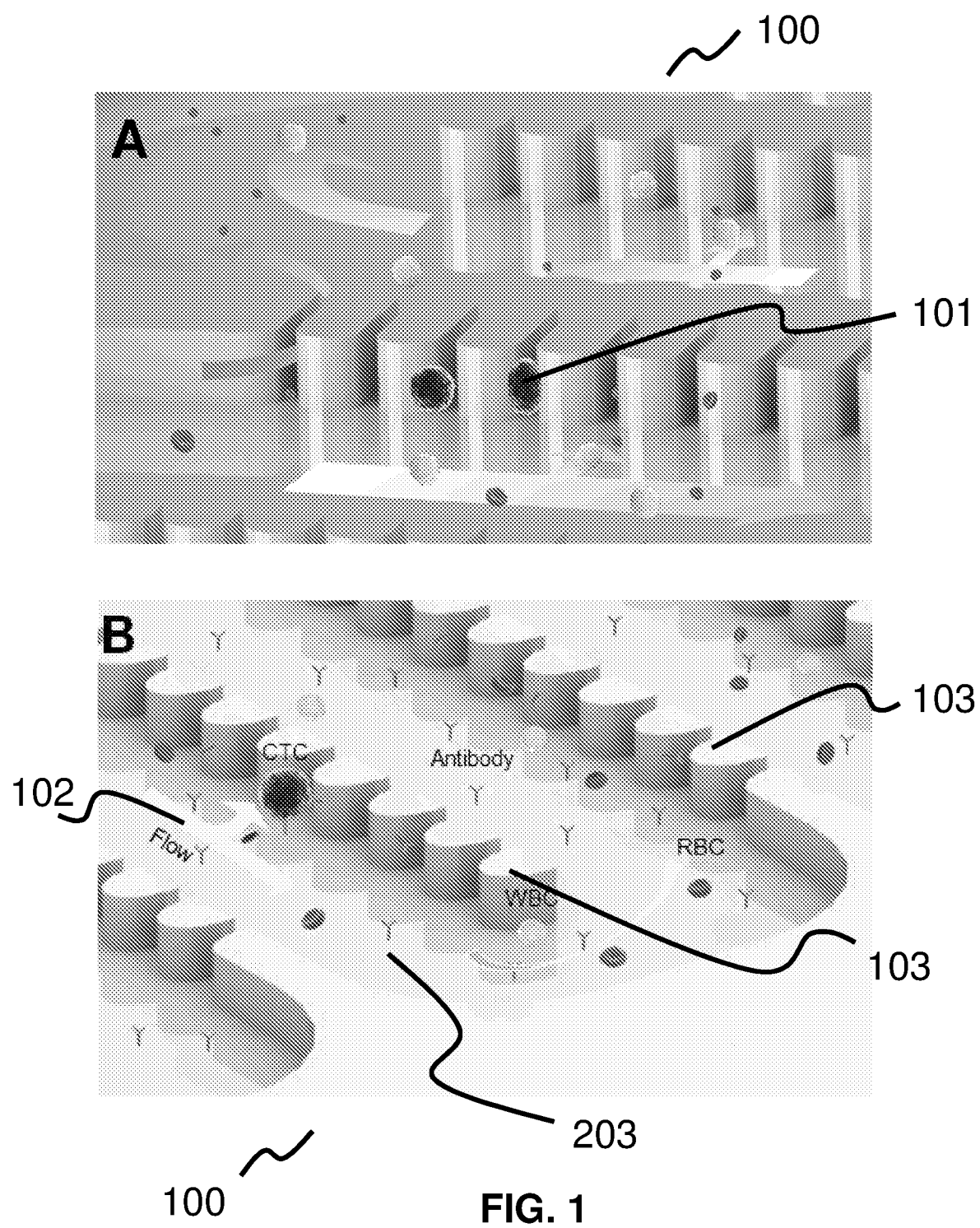
FIG. 1A: is an example according to various embodiments illustrating a lateral filter array microfluidic (LFAM) device integrating size-based separation with immunoaffinity-enabled isolation for detection of circulating tumor cells.
FIG. 1B: is an example according to various embodiments illustrating a serpentine channel in a lateral filter array microfluidic (LFAM) device for main flow and lateral filter arrays for filtration.

FIG. 1A is an example according to various embodiments illustrating a lateral filter array microfluidic (LFAM) device 100 integrating size-based separation with immunoaffinity-enabled isolation for detection of circulating tumor cells 101. FIG. 1B is an example according to various embodiments illustrating a serpentine channel in a lateral filter array microfluidic (LFAM) device 100 for main flow 102 and lateral filter arrays 103 for filtration, like a parking lot, prevent cells from clogging and increase CTC capture efficiency through combined effects.

FIG. 2A is an example according to various embodiments illustrating immunocapture of a circulating tumor cell 101 in the LFAM device 100. FIG. 2B is an example according to various embodiments illustrating a less-preferred affinity-based method of immunocapture in a microfluidic device 205. Devices like microfluidic device 205 attempt to increase the surface-area-to-volume ratio to increase CTC capture probability. However, CTCs can be surrounded by other blood cells, such as white blood cells 201 and red blood cells 202 and not interact with antibodies 203 on the channel walls. The LFAM device enforces direct contact between the CTCs and the antibody functionalized filters. Thus, the interaction between antibodies in the filter and receptors on the cell surface significantly increases.

Figure 3:
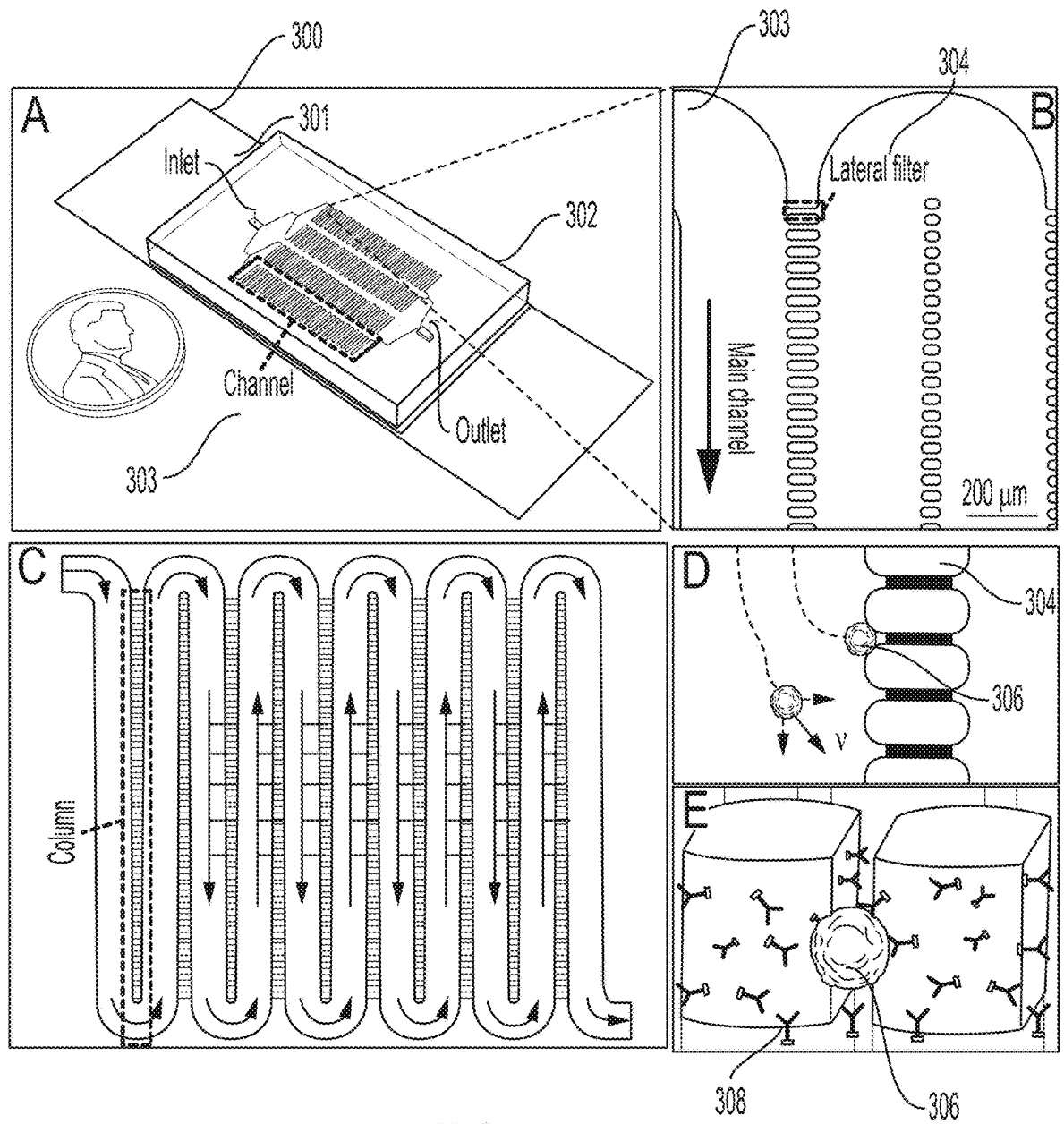
FIG. 3A: is an example according to various embodiments illustrating a prototype of the lateral filter array microfluidic device 300, showing the size of the device 300 relative to a penny.
FIG. 3B: is an example according to various embodiments illustrating an enlarged view of the lateral filter array microfluidic device 300 shown in FIG. 3A.
FIG. 3C: is an example according to various embodiments illustrating a schematic view of the LFAM device 300 as shown in FIG. 3A, with arrows indicating the flow path from the inlet to the outlet.
FIG. 3D: is an example according to various embodiments illustrating the capture of a circulating tumor cell (CTC) 306 in a filter array 304.
FIG. 3E: is an example according to various embodiments illustrating the capture of a circulating tumor cell 306 in a filter array which has been coated with antibodies 308.

FIG. 3A is an example according to various embodiments illustrating a prototype of the lateral filter array microfluidic device 300, showing the size of the device 300 relative to a penny. The device 300 has a plurality of lateral filter arrays 304 connected via channels 303 and an inlet 301 and an outlet 302. As shown in FIG. 3A, the LFAM device may include four serpentine main channels. FIG. 3B is an example according to various embodiments illustrating an enlarged view of the lateral filter array microfluidic device 300 shown in FIG. 3A. As shown in FIG. 3B, in each main channel, a filter array may be embedded. FIG. 3B also includes a scale bar showing a scale for 200 µm. FIG. 3C is an example according to various embodiments illustrating a schematic view of the LFAM device 300 as shown in FIG. 3A, with arrows indicating the flow path from the inlet to the outlet. As shown in FIG. 3C, the serpentine main channel creates a main flow while filters produce numerous branch flows in a lateral direction. A cell flowing through the channel has velocity components in both main channel direction and lateral direction. FIG. 3D is an example according to various embodiments illustrating the capture of a circulating tumor cell (CTC) 306 in a filter array 304. As shown in FIG. 3D, the parking-space-like arrangement of filters helps adjust the flow paths of subsequent cells when one CTC fills a filter. The velocity component in the main channel direction of a cell prevents it from clogging. FIG. 3E is an example according to various embodiments illustrating the capture of a circulating tumor cell 306 in a filter array which has been coated with antibodies 308. As shown in FIG. 3E, the filter geometry forces the direct interaction between a cell and antibodies immobilized on the filter surfaces, increasing the probability of cell capture.

Various embodiments provide a lateral filter array microfluidic (LFAM) device integrated with immunoaffinity-based CTC capture (FIG. 3A and FIG. 21A-F). As shown in FIG. 3B and FIG. 3C, lateral filters may be embedded in a serpentine main channel, producing a main flow in the serpentine channel and lateral flows through filters, in a design like a parking lot. The main channel allows a blood sample to pass through quickly; the filters are designed to permit normal blood cells through while trapping CTCs. The existence of lateral flows induces two velocity components of a flowing cell, as illustrated in FIG. 3D. The parking-space-like arrangement of filters helps adjust the flow pattern when a filter is "filled" by a CTC, changing the flow paths of a subsequent cell. This arrangement prevents cells from clogging, increasing the cell purity. In addition, various filter dimensions from 10 μm to 6 μm (FIG. 21A-F) are created in one device to address the size heterogeneity of CTCs. The geometry of filters forces the direct contact between CTCs and antibodies immobilized on filters (FIG. 3E) because of their comparable size. The large number of filters (13,600 filters) creates sufficiently high contact frequency between CTCs and antibody-functionalized surfaces, significantly increasing the probability of immunocapture.

A variety of LFAM devices, according to various embodiments, were fabricated using soft lithography. These LFAM devices included a glass cover and a polydimethylsiloxane (PDMS) substrate. The serpentine main channel was 300 μm wide and 45 μm in height. All filters had the same height as the main channel, and they were divided into five zones. Each filter zone included 10 columns of lateral filters. The size of filters within each zone was identical, but the sizes in different zones vary from 10 μm to 6 μm, with a deduction of 1 μm in each subsequent zone. The 10-μm-filter zone is located near the inlet and the 6-μm-filter zone is near the outlet (For additional details see: FIG. 21A-F).

Methods for accessing the performance of the LFAM device, according to various embodiments, are also provided. The method comprises introducing a population for cells to the antibodies functionalized LFAM device for filter enhanced target cells capture and washing the LFAM device for non-target cells removal. The LFAM device gives higher target cells capture efficiency than filtration or immunocapture alone.

Design of the LFAM Device

A detailed description of an LFAM device, according to various embodiments, is provided. The LFAM device can have one or more serpentine main channels. Each serpentine main channel may be incorporated with a lateral filter array. In one embodiment, the serpentine main channel may be defined by a series of boundaries that are arranged so as to allow flow of a liquid sample in a serpentine fashion. The series of boundaries comprise a plurality of filters to allow lateral flow of a liquid sample between two sections of the main serpentine channel.

In its broadest sense, the term "filter" as used herein is assembly of one or more filter support structures defining a channel or aperture that connects two sections of the serpentine main channel.

Figure 4:
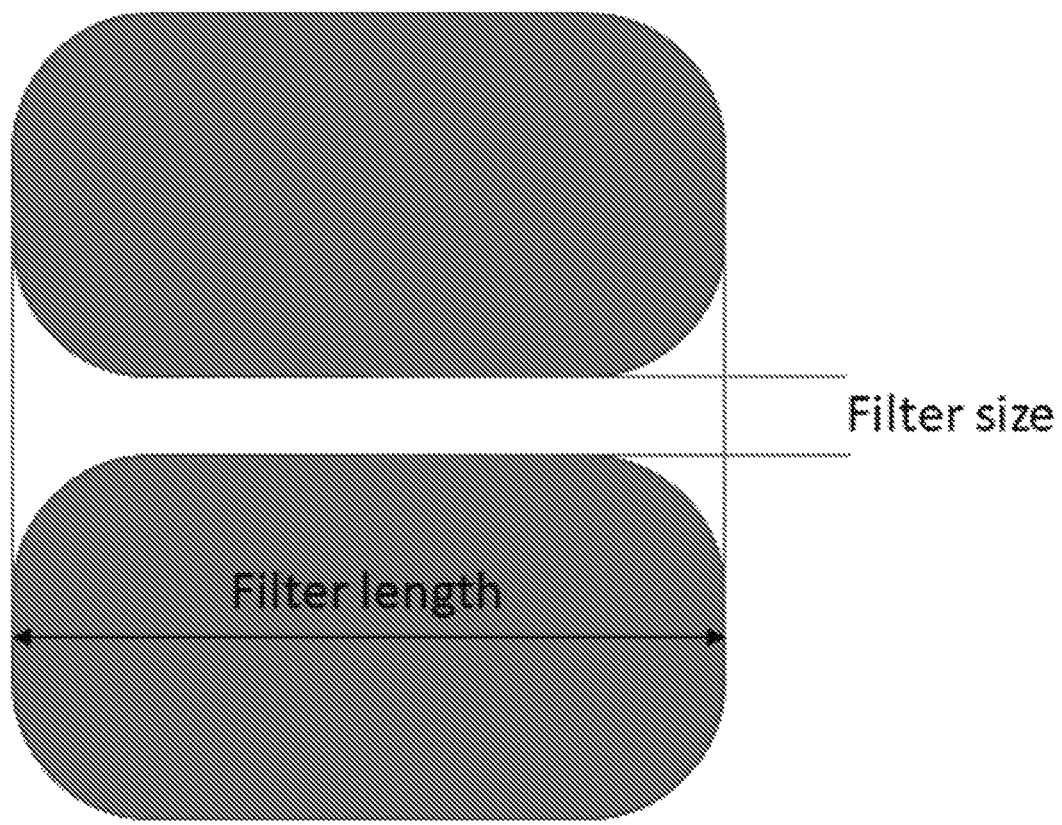
FIG. 4: is an example according to various embodiments illustrating a lateral filter.

FIG. 4. provides a diagram illustrating a lateral filter. In one example, as shown in FIG. 4, a filter may include a channel between two filter support structures. In a specific embodiment, a boundary may include of a row of alternating channels and filter support structures where the filters are arranged in a line to form a demarcation between sections of the serpentine channel. The serpentine main channel can have different widths such as 200 μm, 250 μm, 300 μm, 350 μm, 400 μm, etc. The channel dimension may be dependent on the dimension of the filters, which may be dependent on the size of targets to be isolated. In this sense, width of the serpentine main channel may be the distance between two boundaries. The main channel height can be 30 μm, 35 μm, 40 μm, 45 μm, 50 μm, 55 μm, 60 μm, etc. In this sense, channel height relates to the height of the filter support structures that form a boundary. The filter length may be defined as the distance between the two interfaces of the filter and the serpentine main channel. It can be uniformed or varied within the same column. The filter size may be the smallest dimension of the filter channel or aperture. The filter shape may be considered as the plan view shape of the filter. The filter can have different shapes. For example, the filter can have a wide entrance, a uniform middle channel, and a wide exit. The filter size herein may be defined as the smallest width of the filter. The filters can have different sizes, e.g. 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, etc. The filter dimension may be dependent on the size of targets to be isolated. For example, filters with a range of sizes around 10 μm are designed to separate CTCs from leukocytes, while filters with a range of sizes around 50 nm (0.05 μm) are designed to separate exosomes from blood cells and plasma. Exosomes are one type of cell-derived extracellular vesicles (EVs) that are present in bodily fluids including blood.

The term "target isolate" as used herein refers to a cell or cell component (cell wall, organelles, or parts thereof), extracellular vesicles, virus, and particles in a liquid sample that may be intended to be captured in the LFAM device according to various embodiments.

The term "binding molecule" refers to a molecule having affinity for the target isolate. Examples of binding molecules include but are not limited to antibodies, aptamers, antibody fragments, receptors, or their combinations. Antibodies or antibody fragments include Fab fragments, a Fab' fragments, a heavy chain antibodies, single-domain antibodies (sdAb), variable domain of a heavy chain antibodies, VHH, Nanobodies, single-chain variable fragments (scFv), a tandem scFvs, a bispecific T-cell engagers (BITEs), a diabodies, single-chain diabodies, DARTs, triple bodies, or a nanoantibodies.

Streamline Pattern Simulation

To secure interaction between CTCs and filters, it requires all cells pass through certain filters instead of staying in the serpentine main channel. Ignoring diffusion effect, the streamline pattern in the LFAM device may be a good resemblance to cell flowing paths.

A lumped element model was developed using MATLAB to simulate the streamline pattern in the LFAM device. The microflow system may be analogous to a circuit network. The basic components of the 'virtual circuit network' are hydrodynamic resistances. For example, the main channel and lateral filters are modelled as a series of hydrodynamic resistors.

Figure 5A:
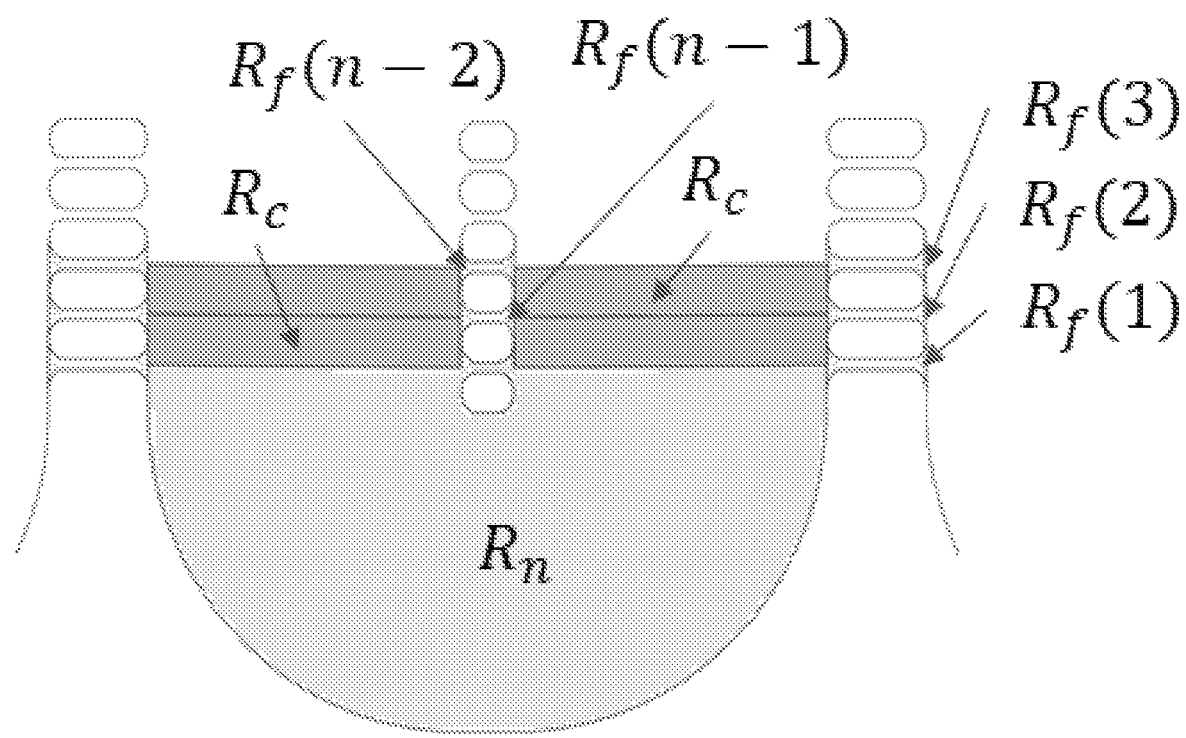
FIG. 5A: is an example according to various embodiments illustrating that a channel of a lateral filter array is analogous to a circuit network.
Figure 5B:
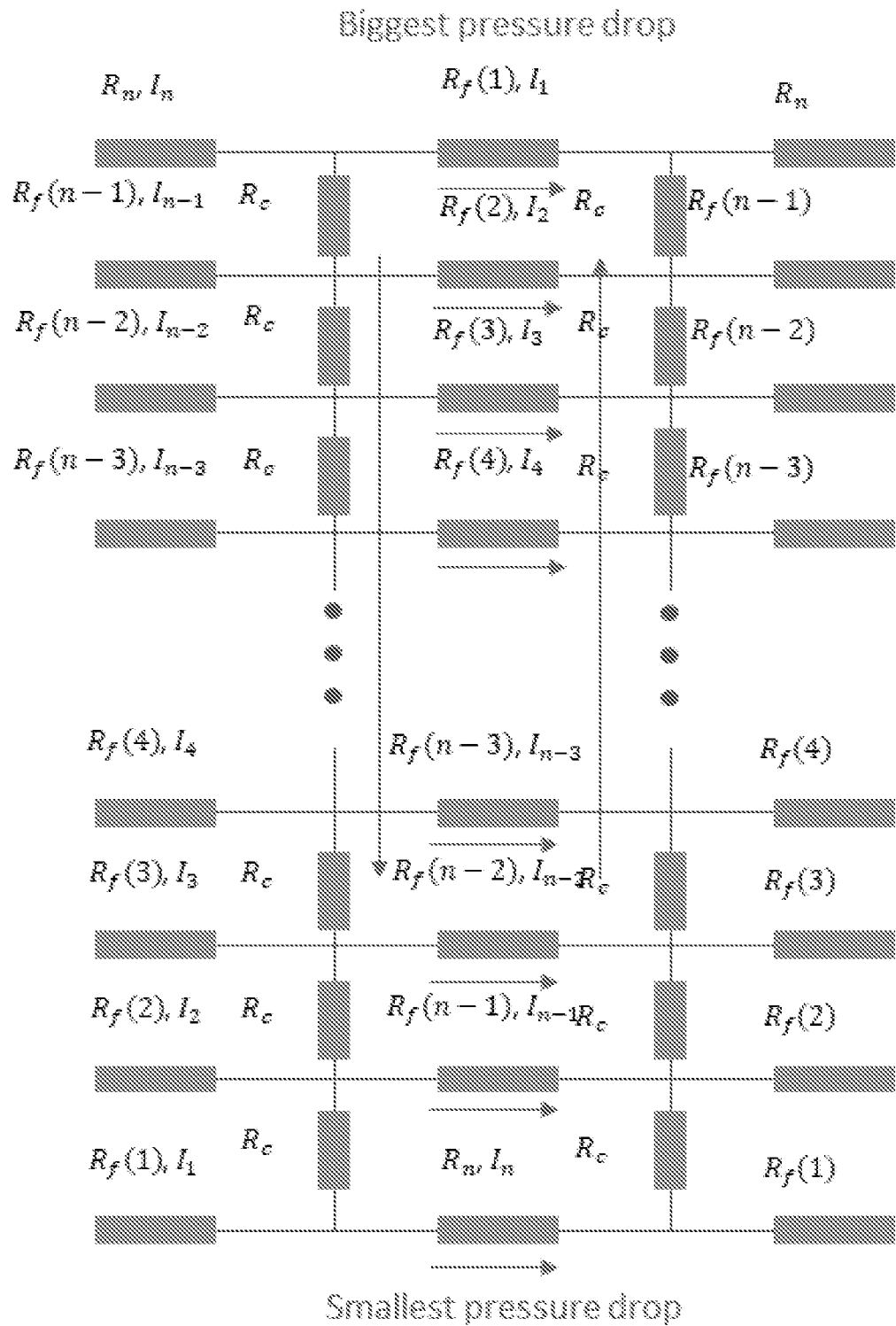
FIG. 5B: is an example according to various embodiments illustrating a channel of a lateral filter array and demonstrating that filters and channel elbows in the adjacent columns are distributed in a reversed order.

FIG. 5A is an example according to various embodiments illustrating that a channel of a lateral filter array is analogous to a circuit network. The three basic components are main channel sections ($R_c$), channel elbows ($R_n$) and filters ($R_f$). Different components are interconnected as shown in FIG. 5B. The filters and channel elbows in the adjacent columns are distributed in a reversed order. Filters from the same column are connected across a main channel section. Since the background pressure decreases along the serpentine main channel, for filters from the same column, Filter 1 (farthest from the elbow) experiences the maximum pressure drop and the channel elbow experiences the minimum pressure drop. The hydrodynamic resistance of the basic components are simulated by COMSOL. As shown, for example, in FIG. 6 pressure drop in different components are obtained by simulation.

As given in FIG. 5A, there are three types of hydrodynamic resistances: main channel sections ($R_c$), channel elbows ($R_n$) and filters ($R_f$). The channel elbow $R_n$ is defined as the elbow paralleled with the neighboring filter whose hydrodynamic resistance is much higher than elbow. The filter $R_f$ includes the wider inlet/outlet and the gap with the designated size. They are interconnected like the channel layout. FIG. 5B is an example according to various embodiments illustrating a channel of a lateral filter array and demonstrating that filters and channel elbows in the adjacent columns are distributed in a reversed order. Accordingly, the flows in the adjacent columns should also be distributed in a reversed order. Considering the total infused flow rate as I, using the Kirchhoff's current law (KCL):

$$I_1+I_2+I_3+\ldots+I_{n-2}+I_{n-1}+I_n=1 \tag{1}$$

Using the Kirchhoff's voltage law (KVL):

$$R_f(k)I_k=R_f(k+1)I_{k+1}+2R_c[(I_n+I_{n-1}+\ldots+I_{n-k+1})-(I_1+I_2+\ldots+I_k)] \tag{2}$$

With all the hydrodynamic resistances given, flow rate in each filter and the elbow can be calculated using Eq.1 and the group of equations represented by Formula (2).

FIG. 6A is an example according to various embodiments illustrating a hydrodynamic resistance model within a channel component of a LFAM device. FIG. 6B is an example according to various embodiments illustrating a hydrodynamic resistance model within a bend component of a LFAM device. FIG. 6C is an example according to various embodiments illustrating a hydrodynamic resistance model within a lateral filter component of a LFAM device. The hydrodynamic resistance of each component was simulated using COMSOL Multiphysics. Given certain flow rate, the pressure drop through the component was simulated, as shown in FIG. 6A, FIG. 6B, and FIG. 6C. Using $\Delta P=RI$, the hydrodynamic resistance of the component was calculated. To ensure the accuracy of the hydrodynamic resistance simulation using COMSOL, a single flat channel was simulated. The simulated hydrodynamic resistance of the flat channel was compared with hydrodynamic resistance calculated by a widely used formula given below $$R = \frac{12\mu L}{wh^3\left(1-\frac{0.63h}{w}\right)} \text{ for } h \ll w \tag{3}$$

Where $\mu$ is the dynamic viscosity of the fluid; L is the length of the channel; w is the width of the channel; h is the height of the channel. The difference between the two methods is 2.2%, showing the accuracy of COMSOL simulation.

The mainstream ratio, defined by the ratio of the flow through the channel elbow (or bend) to the flow through the whole column, determines the downstream zone affected by the channel elbow. This zone is called mainstream zone. FIG. 7A is an example according to various embodiments illustrating flow velocity along a mainstream flow channel of a LFAM device when the mainstream ratio is <<50%. FIG. 7B is an example according to various embodiments illustrating flow velocity along a mainstream flow channel of a LFAM device when the mainstream ratio is <50%. FIG. 7C is an example according to various embodiments illustrating flow velocity along a mainstream flow channel of a LFAM device when the mainstream ratio is =50%. FIG. 7D is an example according to various embodiments illustrating flow velocity along a mainstream flow channel of a LFAM device when the mainstream ratio is >50%. As shown in FIG. 7A, FIG. 7B, FIG. 7C, and FIG. 7D, the mainstream zones (both top and bottom) expand as the mainstream ratio increases. The bigger the mainstream zone is, the bigger the velocity component along the main channel. When the mainstream ratio exceeds 50%, the adjacent elbows will produce an overlapped mainstream zone in the main channel.

A key objective of an LFAM device design, according to various embodiments, may be to guarantee the interaction between cells and the filters. All the cells flowing through the device should cross certain filters to prevent possible cell loss. To track potential paths of cells, the streamline pattern in the LFAM device was studied. Since the Reynold's number in the channel is ~1, laminar flow is dominant. In steady state, the streamlines can be sketched. As shown in FIG. 7A, when the mainstream ratio is <<50% (much less than 50%), the streamlines going through the elbow only cover a few filters in the next column (i.e., the mainstream zones only occupy a tiny portion of the filters). The main channel direction velocity component is very small. When mainstream ratio is significantly increased but still smaller than 50%, as shown in FIG. 7B, more downstream filters are affected by the elbow and the mainstream zone occupies more filters. The main channel direction velocity component is also significantly larger. When mainstream ratio=50%, as shown in FIG. 7C, the elbow affects all filters in the next column (i.e., mainstream zone occupies all filters in the device). The main channel direction velocity component is maximum in applicable range. When mainstream ratio is >50%, as shown in FIG. 7D, the elbows in the neighboring columns have an overlapped zone, producing an overlapped mainstream zone. Cell flowing within the overlapped mainstream zone will stay in the main channel without interacting with filters. Therefore, it's not applicable for CTC isolation.

FIG. 7E is an example according to various embodiments illustrating a streamline pattern in an LFAM device with a mainstream ratio<<50%. FIG. 7F is an example according to various embodiments illustrating a streamline pattern in an LFAM device with a mainstream ratio<50%. FIG. 7G is an example according to various embodiments illustrating a streamline pattern in an LFAM device with a mainstream ratio=50%. FIG. 7H is an example according to various embodiments illustrating a streamline pattern in an LFAM device with a mainstream ratio>50%. Assisted with the lumped element model, provided is the streamline pattern in the LFAM device in FIG. 7E-H. When the mainstream ratio<<50%, as shown in FIG. 7E, the streamline pattern is divided into 3 zones: two mainstream zones occupying elbows and the filters close to the elbows; one middle zone covering majority of the filters. As the mainstream ratio increases, the middle zone is squeezed, and the two mainstream zones occupy more filters, showing bigger velocity components along the main channel, as shown in FIG. 7F. When the mainstream ratio equals 50%, as shown in FIG. 7G, only two mainstream zones are left, with each zone covering one column of filters in the periodic pattern. When mainstream ratio exceeds 50%, as shown in FIG. 7H, a new middle zone (the overlapped mainstream zone) appears which remains in the serpentine main channel without crossing any filter. The virtual zones division essentially determine the interaction between cells and filters in the LFAM device. To prevent possible cell loss along the flow in the main channel, all virtual zones must pass through filters. Therefore, various embodiments ensure mainstream ratio<50%. In FIG. 7E, FIG. 7F, FIG. 7G, and FIG. 7H, the mainstream zones are colored as yellow. As illustrated in FIG. 7E, the term 'mainstream' is defined as the fluid flows through the channel elbow (indicated by a solid-line rectangular). The total flow is defined as the fluid flows through the whole column including filters and the channel elbow (indicated by a dashed-line rectangular). The mainstream ratio is the ratio of flow through the mainstream elbow to flow through the whole column. Through judging the mainstream ratio, it was possible to predict the streamline pattern in the LFAM device. The mainstream ratio is defined as the ratio of flow through the mainstream elbow to flow through the whole column. As streamlines will not intersect, the streamlines through the channel elbow determines its affected zone in the downstream. This zone is considered as the mainstream zone.

To ensure interactions between CTCs and filters, the LFAM device, according to various embodiments, is designed to pass all cells through filters with no cells staying in the main channel only. The device designs may be studied and optimized by analysing the flow paths of cells.

Figure 8:
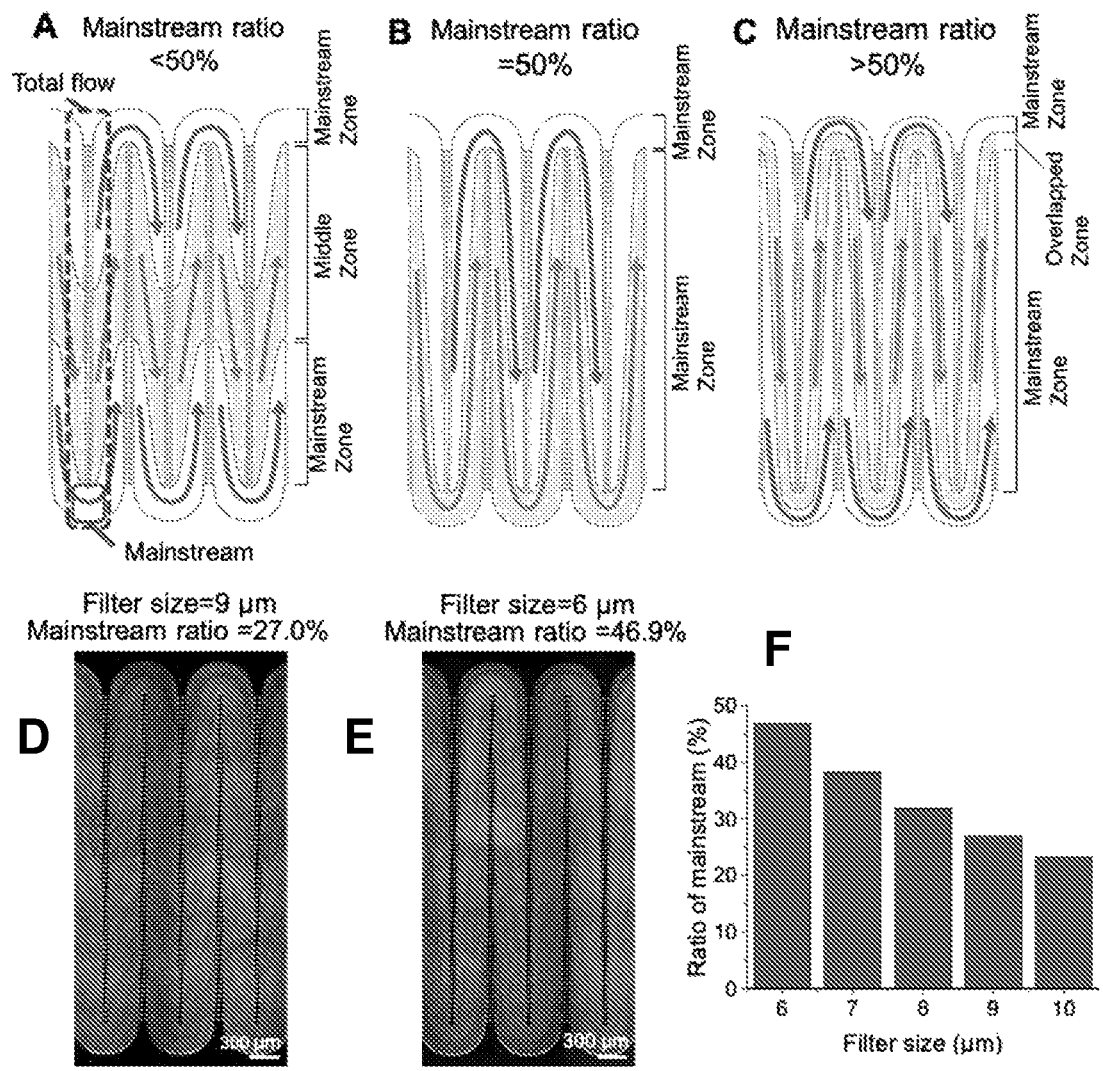
FIG. 8A: is an example according to various embodiments illustrating an annotated version of FIG. 7F.
FIG. 8B: is an example according to various embodiments illustrating an annotated version of FIG. 7G.
FIG. 8C: is an example according to various embodiments illustrating an annotated version of FIG. 7H.
FIG. 8D: is an example according to various embodiments illustrating a photograph of the observed flow pattern for 9-µm filters that have a mainstream ratio of 27.0%.
FIG. 8E: is an example according to various embodiments illustrating a photograph of the observed flow pattern for 6-µm filters that have a mainstream ratio of 46.9%.
FIG. 8F: is an example according to various embodiments illustrating a plot of the mainstream ratios for different filter sizes in LFAM.

FIG. 8A is an example according to various embodiments illustrating an annotated version of FIG. 7F. FIG. 8A shows the simulated streamline pattern in LFAM when mainstream ratio is <50%. FIG. 8B is an example according to various embodiments illustrating an annotated version of FIG. 7G. FIG. 8B shows the streamline pattern in LFAM when mainstream ratio=50%. FIG. 8C is an example according to various embodiments illustrating an annotated version of FIG. 7H. FIG. 8C shows the streamline pattern in LFAM when mainstream ratio is >50%. FIG. 8D is an example according to various embodiments illustrating a photograph of the observed flow pattern for 9-μm filters that have a mainstream ratio of 27.0%. FIG. 8E is an example according to various embodiments illustrating a photograph of the observed flow pattern for 6-μm filters that have a mainstream ratio of 46.9%. FIG. 8F is an example according to various embodiments illustrating a plot of the mainstream ratios for different filter sizes in LFAM.

The flow pattern in LFAM may be affected by the distribution of hydrodynamic resistance (For additional details see: FIG. 22A, FIG. 22B, FIG. 22C, FIG. 22D, and FIG. 22E). Within each column of a microchannel, the mainstream is defined as the flow through the channel elbow, as shown in FIG. 8A. The total flow is defined as the flow through both filters and channel elbow in the same column. The mainstream ratio is defined as the ratio of the mainstream to the total flow. Adjusting the mainstream ratio leads to various streamline patterns in LFAM. The theoretically predicted flow pattern was then compared with experimental observation. As shown in FIG. 8A, when the mainstream ratio is smaller than 50%, the streamline pattern is divided into 3 zones: one mainstream zone through the top elbow, one mainstream zone through the bottom elbow, and one middle zone covering only filters. As the mainstream ratio increases, the middle zone is squeezed, and the two mainstream zones expand. When the mainstream ratio equals 50%, the middle zone disappears, with each mainstream zone covering one column of filters periodically (FIG. 8B). When mainstream ratio exceeds 50%, a new middle zone appears due to the overlap of the neighbouring mainstream zones (FIG. 8C). The overlapped zone stays in the serpentine main channel without passing any filters. Cells staying in the overlapped zone will not interact with any lateral filters, resulting in possible cell loss. As a result, the mainstream ratio should be no more than 50%. The simulation results are summarized in FIG. 8F, which shows that the mainstream ratio increases from 23.2% to 46.9% when the filter size decreases from 10 μm to 6 μm.

EXAMPLES

The following examples are put forth to provide those of ordinary skill in the art with a complete disclosure and description of how to perform the methods, how to make, and how to use the compositions and compounds disclosed and claimed herein. Efforts have been made to ensure accuracy with respect to numbers (e.g., amounts, temperature, etc.), but some errors and deviations should be accounted for. The purpose of the following examples is not to limit the scope of the various embodiments, but merely to provide examples illustrating specific embodiments.

Example 1

Fabrication of the LFAM Device

The fabrication of LFAM devices, according to various embodiments, may include two processes: silicon master fabrication and device fabrication. For silicon master fabrication, an economic processing method was chosen based on the smallest filter size. If the smallest filter size may be bigger than 10 μm, a transparency dark field photomask may be used. SU8 photoresist may be coated on the silicon wafer and the designed pattern may be transferred from the transparency photomask to the SU8 photoresist by photolithography. For filter size smaller than 10 μm, a bright field chrome mask may be used. The pattern may be transferred from the chrome mask to a thin (~2 μm) positive photoresist layer coated on the silicon wafer through photolithography. Then the part of wafer not covered by photoresist may be etched down by specific depth (e.g. 45 μm) using deep reactive-ion etching (DRIE), followed by photoresist strip.

The LFAM device, according to various embodiments, may include a polydimethylsiloxane (PDMS) substrate and a glass slide cover. The PDMS substrate containing microfeatures may be formed by soft lithography using the silicon masters. The PDMS substrate and the glass slide are bonded after being treated with UV-Ozone for 5 minutes.

It should be noted that PDMS is just an example of thermoset materials used to fabricate LFAM devices. The device may be fabricated using silicon, glass, and thermoplastics as will be understood by those of skill in the art in view of the description provided herein.

In addition to conventional photolithography and casting mentioned above, thermoplastic microfluidic devices can be fabricating using molding, milling, machining, 3D printing, and other methods as will be understood by those of skill in the art in view of the description provided herein. Nanostructured filters can be fabricating using electron-beam lithography (often abbreviated as e-beam lithography) and other methods as will be understood by those of skill in the art in view of the description provided herein.

Functionalization of the LFAM Device

The LFAM device was first filled with 99% ethanol to exhaust air in the microchannels. Then device was washed with Dulbecco's phosphate buffered saline (DPBS; Fisher Scientific, Hampton, NH). For filtration only experiments, the LFAM device was simply passivated with 1% bovine serum albumin (BSA). For immunocapture, the LFAM device was functionalized with antibody against epithelial cellular adhesion molecule (anti-EpCAM). The first step was to immobilize avidin on the device surface by physical adsorption. About 1 channel-volume of 1 mg/ml avidin (50 µl) was introduced to the LFAM device and incubated for 15 minutes. After avidin immobilization, the LFAM device was washed with DPBS. The second step was anti-EpCAM functionalization. One channel volume of 10 µg/ml biotinylated anti-EpCAM was introduced to the device and incubated for 15 minutes. Anti-EpCAM was immobilized due to biotin-avidin interaction. Before use, the LFAM device was also passivated with 1% BSA.

Cell Culture and Sample Preparation

L3.6pl cells were obtained from Dr. Jose Trevino's lab (Department of Surgery, University of Florida). CCRF-CEM cells were purchased from American Type Culture Collection (ATCC). The L3.6pl cells were cultured in DMEM medium (ATCC) supplemented with 10% fetal bovine serum (FBS, GIBCO) and 100 units/mL penicillin-streptomycin (Cellgro, Manassas, Va.). The CCRF-CEM cells were cultured in RPMI1640 medium (ATCC) with 10% FBS and 100 units/mL penicillin-streptomycin. Different cell lines were cultured at 37° C. with 5% $CO_2$.

Cell Sample Preparation

L3.6pl cells are adherent cells. For cell sample preparation, the culture medium was first removed from the flask and DPBS was added to rinse the flask for impurities removal. 2 mL of 0.25% trypsin EDTA (GIBCO, Fisher Scientific) was introduced and incubated for 10 minutes to detach the cells from the flask. Then 6 mL of growth medium was added to the flask to neutralize the cells. The detached cells were then rinsed with DPBS 2 times to remove impurities. Finally, the cells were resuspended in 1 mL of DPBS.

CCRF-CEM cells are floating cells. For cell sample preparation. The cells were simply withdrawn from the flask and rinsed with DPBS 2 times and resuspended in 1 mL of DPBS.

Vybrant fluorescence dyes were used for cells labeling. Vybrant dyes are lipophilic membrane stains that can emit fluorescence under activation after incorporating with the membrane of a cell. The dye was added to the suspended cells at 7 µL per $10^6$ cells. The labeling solution was incubated for 20 minutes at 37° C. Afterwards, the cells were washed with DPBS 3 times and resuspended in DPBS. The labeled cells were then spiked in buffer or healthy blood samples.

Spiked Sample Processing Using the LFAM Device.

A sample including cells spiked in a buffer or cells spiked in blood was loaded in a 1 mL or 3 mL or 5 mL syringe. The syringe was fixed in a syringe pump and connected to the LFAM device through tubing. The sample was infused to the antibody-functionalized LFAM device by syringe pumping. A rotating magnetic bar was put in the syringe to agitate the sample during infusion to prevent cells settling in the syringe. The infused flow rate can be 1.8 ml/h, 3.6 ml/h, 5.4 ml/h, or 7.2 ml/h. After sample infusion, 250 µL DPBS was infused to LFAM device to wash away leftover non-target cells.

Clinical Sample

Blood samples of 10~20 mL from patients with metastatic pancreatic cancer were obtained from the University of Florida Health Cancer Center. The samples were collected in BD Vacutainers containing anti-coagulant sodium heparin. All samples were processed within 5 hours after sample collection. A clinical sample of 2-4 mL was processed using the anti-EpCAM functionalized-LFAM device. After sample processing, 100 µL of 4% paraformaldehyde was infused through the LFAM device and incubated for 10 minutes for fixation. After washing with 200 µL of DPBS, 100 µL of 0.2% Triton X-100 was introduced and incubated for another 10 minutes for cell permeabilization. After washing with 200 µL of DPBS, a cocktail of fluorescence dye including 60 µL of 500 nM DAPI, 10 µL of 10 µg/mL anti-cytokeratin-FITC, 10 µL of 10 µg/mL anti-CD45-PE, was introduced and incubated for 25 minutes for labeling captured cells. The LFAM device was then washed with 500 µL DPBS after cells labeling. Captured cells were enumerated under the fluorescence microscope, Olympus IX71 microscope. CTCs were counted as DAPI+, CK+, CD45−, while white blood cells were detected as DAPI+, CK−, CD45+. Triple positive cells were considered as false positive signals that may come from impurities.

Example 2

Geometry of LFAM Device

For affinity-based CTC isolation, the direct contact between CTCs and antibody immobilized inner surface of the microchannels may be required. Increasing the area-to-volume ratio can help increasing the probability of interaction between CTCs and antibodies. However, the CTC may not interact with antibody-functionalized inner surface especially when they are surrounded by a huge number of blood cells. On the other hand, filter-based devices usually drive cells through filters that are smaller than CTCs. Direct contact between CTCs and the device may be inevitable. The objective here is applying filter-like features to enforce the interaction between CTCs and antibody-functionalized device. The filter size may be designed to be about the size of the CTC. When entering the filter, the flow may be regulated so that only a single CTC can cross the filter. This prevents the CTC from being entangled by other blood cells, thus significantly increasing the direct contact between the CTC and the antibody functionalized device. To prevent cells clogging, a serpentine main channel may be designed between different columns of filters. When a cell flows through the LFAM device, it may have two velocity components along both the main channel direction and the filter direction. This design prevents cells from continuously clogging the same filter. Additionally, the wider main channel reduces to overall hydrodynamic resistance of the device and lowers the flow velocity in the filters, thus increasing the probability of CTC capture.

Geometry Layout of an LFAM Device

Figure 9:
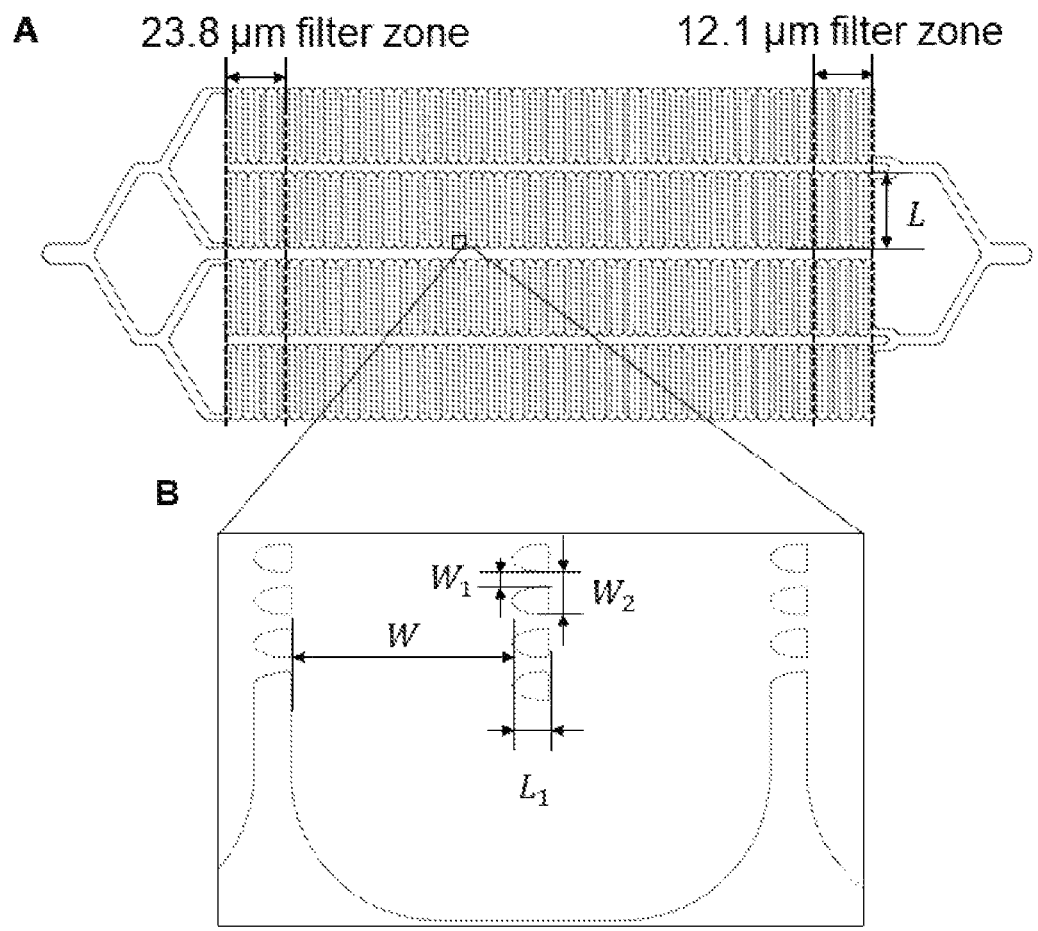
FIG. 9A: is an example according to various embodiments illustrating a schematic diagram of a LFAM device.
FIG. 9B: is an example according to various embodiments illustrating a detailed view of a section of the LFAM device illustrated in FIG. 9A.

FIG. 9A is an example according to various embodiments illustrating a schematic diagram of an LFAM device. As shown in FIG. 9A, the LFAM device comprises 4 serpentine main channels with an array of lateral filters incorporated in each serpentine main channel. The lateral filters are divided into 11 zones based on filter size. Each filter zone includes 10 columns of lateral filters of the same size. The biggest filter zone (23.8 µm filter zone) may be located near the inlet of the LFAM device. The smaller filter zone (12.3 µm filter zone) may be located near the outlet of the LFAM device. For different embodiment, there can be 68 or 34 lateral filters in a column. The folded length of the serpentine channel L=4526 µm. The width of the main channel may be W=300 µm, and its depth may be d=45 µm. An array of filters may be incorporated in the serpentine main channel. The distributed filters have different dimensions. Near inlet, the filter width may be $W_1$=23.8 µm. The filter width decreases by about 1.15 µm every 10 columns. There are total of 110 columns of filters. The smallest filter width may be 12.3 µm.

The length of each filter may be $L_1=50$ μm. The distance between two adjacent filters may be $W_2=58$ μm.

FIG. 9B is an example according to various embodiments illustrating a detailed view of a section of the LFAM device illustrated in FIG. 9B. To decrease cell deformation, the lateral filters are designed to be approximately 'wedge shape' with a wider opening in the entrance, as illustrated in FIG. 9B. The filter size is defined by the smallest width in the filter. The depth of the main channel and lateral filters are 40 μm. The LFAM device has 68 lateral filters per column. As shown in FIG. 9B, the width of the serpentine channel may be W=300 μm; The length of the filter $L1=50$ μm; the filter size W1 varies from 12.3 μm to 23.8 μm. The distance between to lateral filters W2 can be 50 μm or 100 μm depending on the number of filters.

Figure 10A:
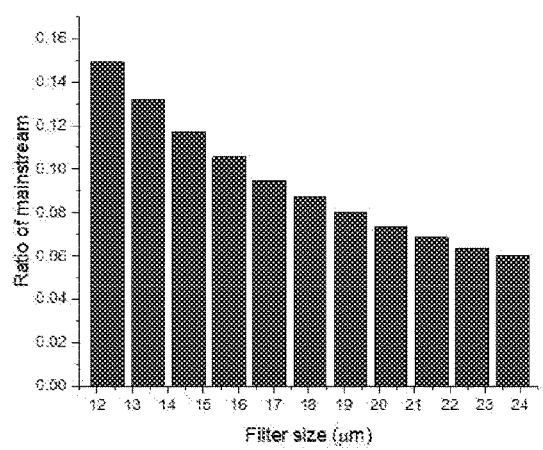
FIG. 10A: is an example according to various embodiments illustrating showing mainstream ratio in different filter zones in the LFAM device illustrated in FIG. 9A.
Figure 10B:
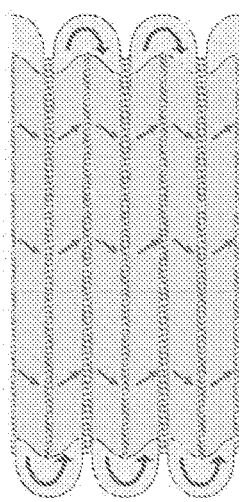
FIG. 10B: is an example according to various embodiments illustrating a streamline pattern in the LFAM device illustrated in FIG. 9A with a mainstream ratio<<50%.
Figure 10C:
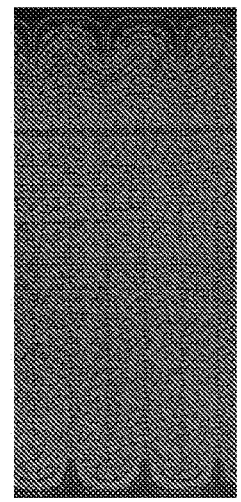
FIG. 10C: is an example according to various embodiments illustrating a photograph of the observed flow pattern for the LFAM device illustrated in FIG. 9A and FIG. 10B.

FIG. 10A is an example according to various embodiments illustrating showing mainstream ratio in different filter zones in the LFAM device illustrated in FIG. 9A. Using the theoretical model, the streamline pattern in the LFAM device was calculated and compared with experiment. As given in FIG. 10A, for different filter sizes from 12.3 μm to 23.8 μm, the mainstream ratio ranged from 6.0% to 14.9%, satisfying the condition mainstream<<50%. FIG. 10B is an example according to various embodiments illustrating a streamline pattern in the LFAM device illustrated in FIG. 9A with a mainstream ratio<<50%. FIG. 10C is an example according to various embodiments illustrating a photograph of the observed flow pattern for the LFAM device illustrated in FIG. 9A and FIG. 10B. Together FIG. 10B and FIG. 10C provide a comparison of streamline pattern predicted by the theoretical model and the streamline pattern observed in the experiment. The corresponding flow pattern was verified by observed streamline pattern in the experiment when 2-time diluted whole blood was infused to the LFAM device (FIGS. 10B and 10C). The streamline pattern study confirm that all cells will pass through certain filters in the LFAM device. Since the smallest feature in the LFAM device is bigger than 10 μm, the silicon master was made of SU8 photoresist and a silicon wafer through photolithography. The PDMS based LFAM device was then fabricated by soft lithography using soft lithography.

Figure 11:
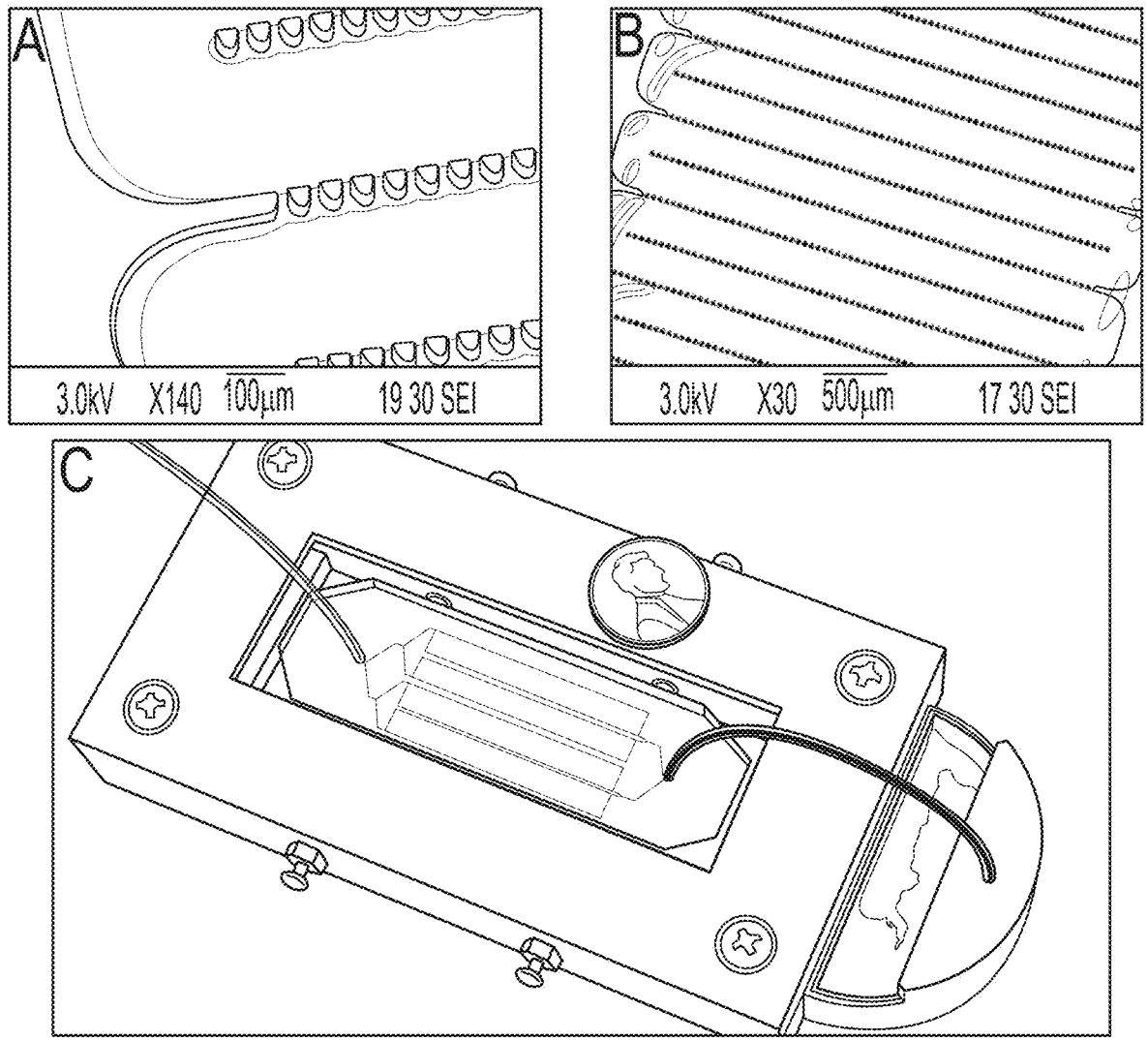
FIG. 11A: is an example according to various embodiments illustrating an SEM image that show the serpentine main channel and the arrangement of the lateral filters in an LFAM device.
FIG. 11B: is an example according to various embodiments illustrating an SEM image that show the serpentine main channel and the arrangement of the lateral filters in an LFAM device.
FIG. 11C: is an example according to various embodiments illustrating an entire PDMS-based LFAM device.

The fabricated LFAM device is shown in FIG. 11A, FIG. 11B, and FIG. 11C. FIG. 11A and FIG. 11B are examples according to various embodiments illustrating SEM images that show the serpentine main channel and the arrangement of the lateral filters in an LFAM device. FIG. 11C is an example according to various embodiments illustrating an entire PDMS-based LFAM device.

Cell Capture Pattern in the Microchannel

About 10000 fluorescence labeled L3.6pl cells were infused to LFAM device. The LFAM device can be functionalized with anti-EpCAM or simply passivated with BSA. The infusion flow rate was 1.8 ml/h, 3.6 ml/h, 5.4 ml/h, or 7.2 ml/h.

Figure 12A:
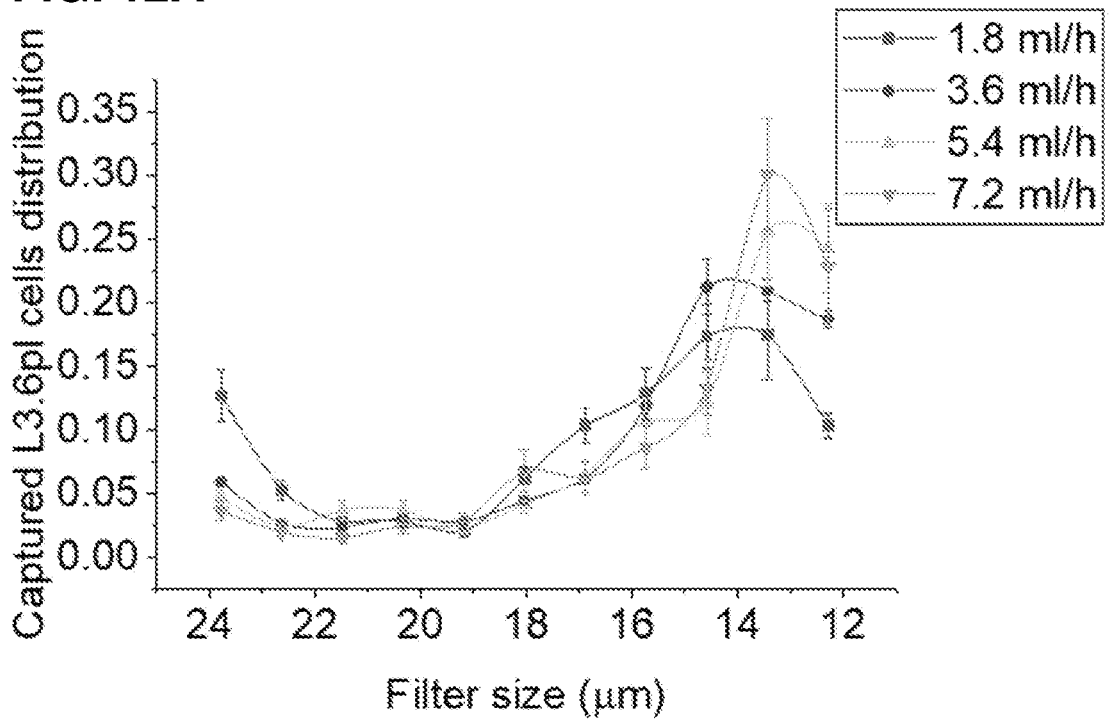
FIG. 12A: is an example according to various embodiments illustrating captured L3.6pl cells distribution in the LFAM device without antibody coated under different flow rates.
Figure 12B:
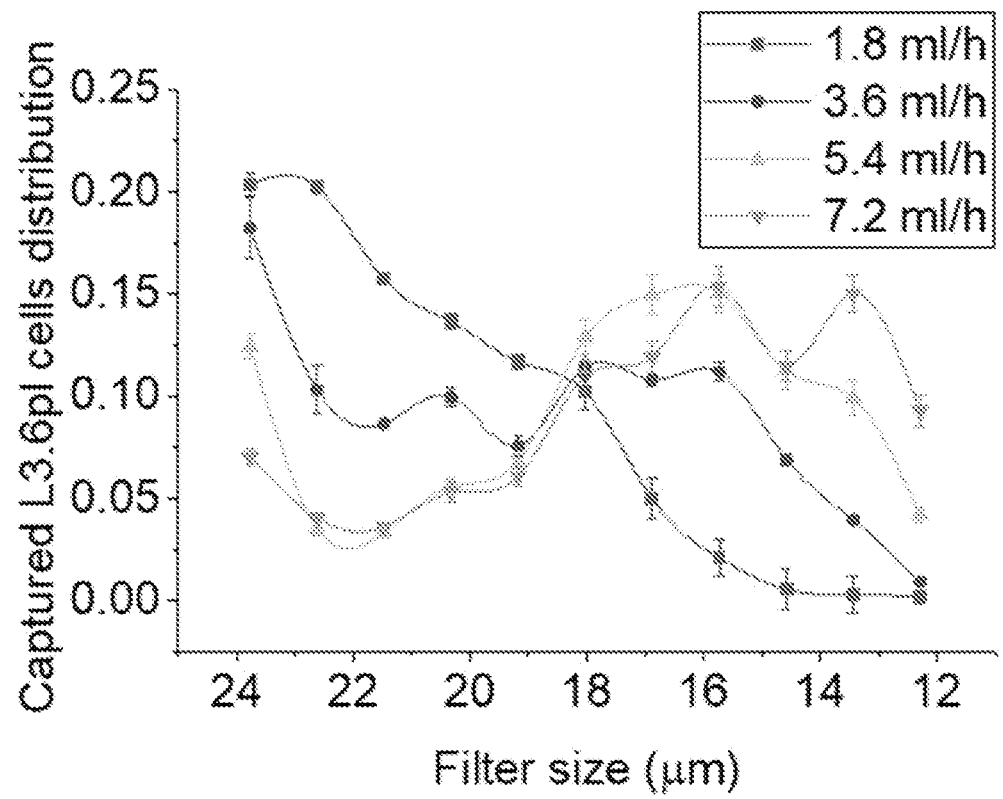
FIG. 12B: is an example according to various embodiments illustrating captured L3.6pl cells distribution in the LFAM device with antibody coated under different flow rates.

FIG. 12A is an example according to various embodiments illustrating captured L3.6pl cells distribution in the LFAM device without antibody coated under different flow rates. FIG. 12B is an example according to various embodiments illustrating captured L3.6pl cells distribution in the LFAM device with antibody coated under different flow rates.

The cell capture patterns in the anti-EpCAM coated LFAM device were also compared with the cell capture patterns in the LFAM device without anti-EpCAM coated. As shown in FIG. 12A, for different infused flow rates, cells capture peaks are all located between the 15.7 μm filter zone and 12.1 μm filter zone where filter sizes are smaller than the cell sizes.

The diameter of L3.6pl cells were measured to be 15.93±3.08 μm. The microchannel is divided into 11 zones based on the filter size. Each zone includes 10 columns of identical lateral filters. The capture ratio is defined as the number of cells captured in certain filter zone to the total number of cells captured in the LFAM device. FIG. 12B shows cell capture ratio in different filter zones of the anti-EpCAM-coated LFAM device under different flow rates. At 1.8 ml/h, most L3.6pl cells (91.8%) are captured in the front half of the microchannel (23.8 μm filter zone to 18.1 μm filter zone). The 23.8 μm filter zone and 22.6 μm filter zone include 40.6% of the total captured L3.6pl cells with 23.8 μm filter zone occupying 20.3% of the total captured cells. The capture ratio decreases along the microchannel and is close to zero near the outlet. The back half of the LFAM device (16.9 μm filter zone to 12.1 μm filter zone) captured only 8.2% of L3.6pl cells. At 3.6 ml/h, capture peak also exist in 23.8 μm filter zone (18.2%). The L3.6pl cells capture ratio between 22.6 μm filter zone and 19.2 μm filter zone in the front half decreases from 61.2% to 36.5% while the capture ratio between the 16.9 μm filer zone and 12.3 μm filter zone in the back half increases from 8.2% to 33.8%. At 5.4 ml/h, the capture peak near the capture ratio between 22.6 μm filter zone and 19.2 μm filter zone further decreases to 19.3% while the capture ratio between the 16.9 μm filer zone and 12.3 μm filter zone increases to 55.4%. At 7.2 ml/h, the capture pattern is close to that at 5.4 ml/h. For flow rates higher than 1.8 ml/h, capture peaks can be observed between 18.1 μm filter zone and 15.7 μm filter zone.

Several arguments can be made from the L3.6pl cells capture pattern in the anti-EpCAM-functionalized FLA device. First, the cell capture enhancement effect by the lateral filters is more significant as flow rate increase: more cells are captured on the back half of microchannel where filter sizes are similar or smaller than the cell size. Second, the 23.8 μm filter zone near the inlet gives high cell capture ratio even at relatively high flow rates (3.6 to 5.4 ml/h). It may be due to the fact that flow velocity is relatively low (since the filter size is big). Third, filters with similar size with the cells diameter give the best cell capture enhancement effect. For higher flow rates (3.6 to 7.3 ml/h), the filter zones between 18.0 μm and 15.7 μm give significantly high cell capture ratio. Noting that the measured diameters of the cells are in the same range, cells passing through these filters inevitably contact the antibody-functionalized lateral filters. Therefore, the cells are more likely to be captured in these zones of the microchannel.

FIG. 34E is an example according to various embodiments illustrating L3.6pl cells capture in an LFAM device under two different conditions: with antibody coated and without antibody coated. As given in FIG. 34E, without anti-EpCAM immobilization, the LFAM device brings low CTC capture efficiency. Only 10-20% of both types of cells are captured even at a low infused flow rate, 1.8 ml/h. This is expected as the filter sizes are relatively big compared with the cell size. The smallest filter size may be 12.3 μm. Noting that the channel height may be about 45 μm, it's easy for a cell to deform 23% in one-direction to pass the filter. However, when the device is functionalized with anti-EpCAM, the capture efficiency increases dramatically. For L3.6pl cells, the capture efficiency may be 91.3±3.0% at 1.8 ml/h. The significantly improvement of cell capture capability demonstrates that affinity-based cell capture may be predominated in the anti-EpCAM-functionalized LFAM device.

Capture of Target Cells from a Cell Mixture 1000 of L3.6pl cells were spiked in non-target CCRF-CEM cells at a ratio of 1:20. The cell mixture was then infused to the antibody-functionalized LFAM device at 1.8 ml/h and 3.6 ml/h. The cell capture purity was defined as the number of captured target cells over the total cells enumerated in the LFAM device.

FIG. 35A is an example according to various embodiments illustrating capture of target L3.6pl cells in the antibody coated LFAM device from a population of cells at 1.8 ml/h and 3.6 ml/h. The target cell capture efficiency was 90.8±7.8% for 1.8 ml/h and 88.2±5.2% for 3.6 ml/h. FIG. 35B is an example according to various embodiments illustrating capture of target L3.6pl cells purity in the antibody coated LFAM device at 1.8 ml/h and 3.6 ml/h. At the same time, the purity increased from 49.5±6.7% to 57.5±1.2% as the flow rate increased from 1.8 ml/h to 3.6 ml/h.

The sorting purity shows that the control cells decreased by more than 95% as the flow rates increases to 3.6 ml/h, while the target cell capture efficiency may be still as high as 88.2±5.2%. It demonstrates that the antibody-functionalized LFAM device, according to various embodiments, may be efficient at relatively high flow rate and gives good capture purity as well.

Capture of Target Cells Spiked in Diluted Blood

Figure 13A:
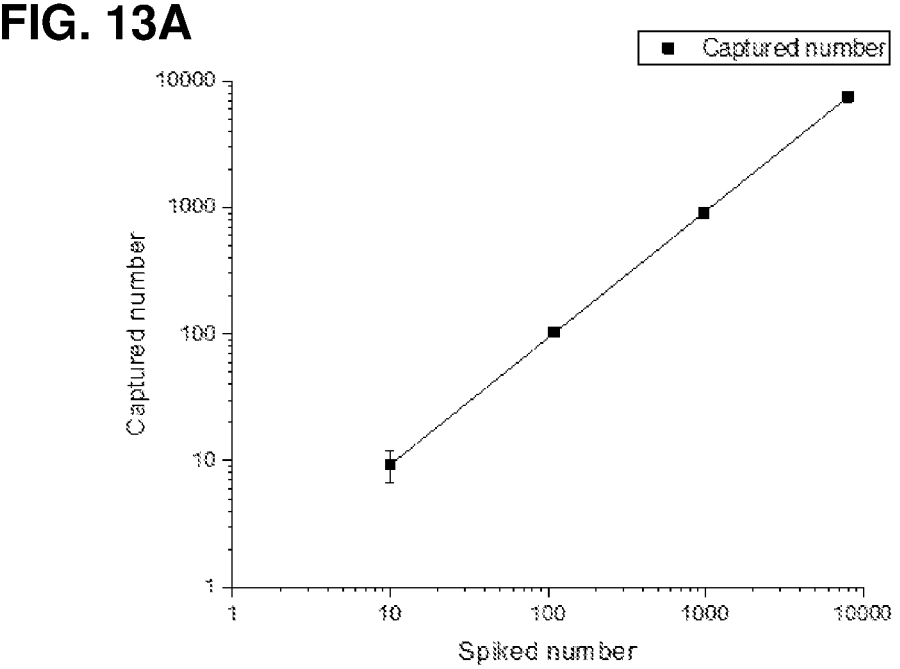
FIG. 13A: is an example according to various embodiments illustrating comparison of spiked L3.6pl cells and captured L3.6pl cells.
Figure 13B:
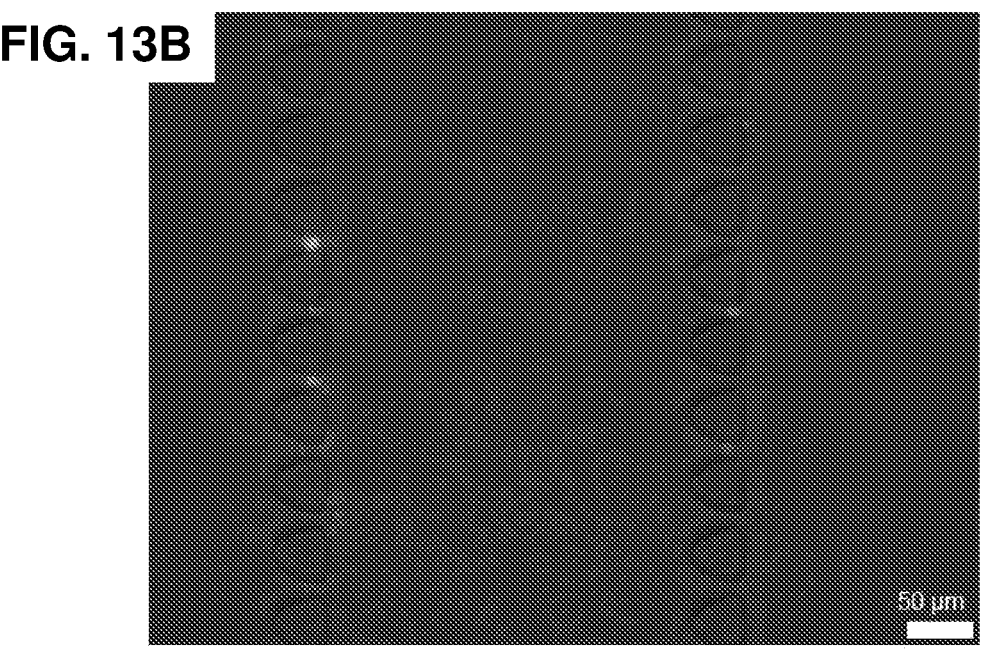
FIG. 13B: is an example according to various embodiments illustrating captured L3.6pl cells (green) and non-specific captured white blood cells (red)

Different amount of L3.6pl cells are spiked in 1 mL of 2-time diluted healthy whole blood and infused to the antibody functionalized LFAM device. FIG. 13A is an example according to various embodiments illustrating comparison of spiked L3.6pl cells and captured L3.6pl cells. FIG. 13B is an example according to various embodiments illustrating captured L3.6pl cells (green) and non-specific captured white blood cells (red).

To mimic CTC capture in clinical condition, L3.6pl cells were spiked to healthy blood samples and introduced to the EpCAM-functionalized LFAM device. 10 to 10,000 of L3.6pl cells were spiked to 2 times diluted whole blood (whole blood:DPBS=1:1) and the infusion flow rate was 3.6 ml/h. The number of spiked cells versus the number of captured L3.6pl cells was given in FIG. 13A. The captured/spiked ratio maintained good linearity for different spike concentrations. The capture efficiency was as high as 93.5±0.5%, which was higher than the capture efficiency with pure cell lines. FIG. 13B showed spiked L3.6pl cells captured in the lateral filters.

Isolation of CTCs from Blood of Pancreatic Patients

The antibody-functionalized LFAM device was used for CTC isolation from clinical blood samples from patients with metastatic pancreatic cancer. The clinical sample tests of the LFAM device were compared with an ongoing clinical study using GEM chips. [5] A clinical sample of 2~4 ml was first treated with Ficoll-Paque to separate plasma and red blood cells from mononuclear cells. Afterwards, the isolated nucleated cells were resuspended in 1 ml DPBS. The nucleated cell sample was then introduced to the anti-EpCAM coated LFAM device at 1 µl/s. After DPBS washing, captured cells were fixed with 4% paraformaldehyde (PFA) for 10 minutes, followed be permeabilized with 0.2% Triton X-100 for 10 minutes. Then, a mixture of labeling dye containing 10% of 10 µg/ml FITC anti-cytokeratin, 10% of 10 µg/ml PE anti-CD45 and 80% of 500 nM DAPI were introduced into the LFAM device and incubated for 30 min. After DPBS washing, CTCs were enumerated under the optical microscope. When processing clinical sample with the LFAM device, the clinical study using the GEM device was conducted separately.

Figure 14:
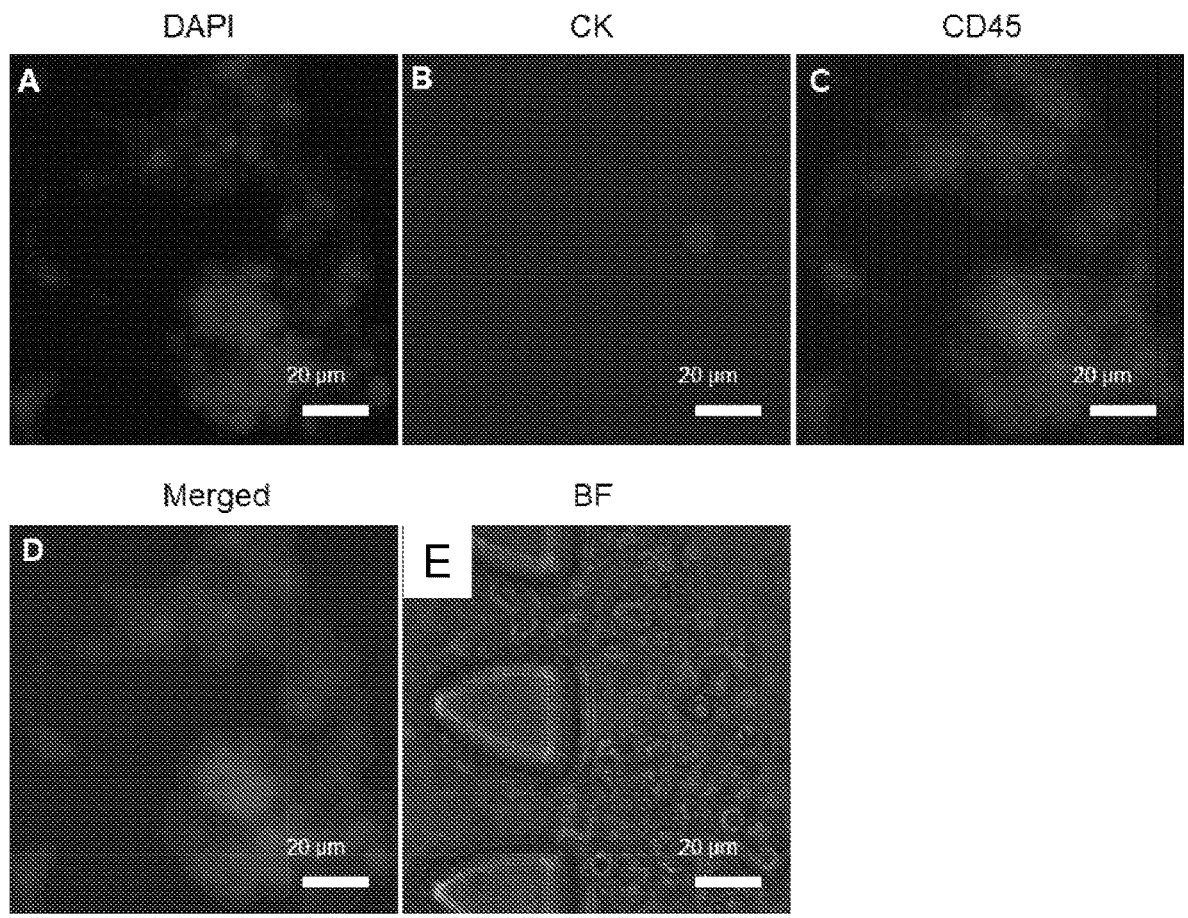
FIG. 14A: is an example according to various embodiments illustrating a DAPI channel image of captured CTC and nonspecific captured white blood cells.
FIG. 14B: is an example according to various embodiments illustrating a CK-FITC channel image of captured CTC and nonspecific captured white blood cells.
FIG. 14C: is an example according to various embodiments illustrating a CD45-PE channel image of captured CTC and nonspecific captured white blood cells.
FIG. 14D: is an example according to various embodiments illustrating a merged image of the 3 channels of captured CTC and nonspecific captured white blood cells.
FIG. 14E: is an example according to various embodiments illustrating a brightfield image of captured CTC and nonspecific captured white blood cells.

FIG. 14A, FIG. 14B, FIG. 14C, FIG. 14D, and FIG. 14E are sample images of captured CTC and nonspecific captured white blood cells. FIG. 14A is an example according to various embodiments illustrating a DAPI channel image of captured CTC and nonspecific captured white blood cells. FIG. 14B is an example according to various embodiments illustrating a CK-FITC channel image of captured CTC and nonspecific captured white blood cells. FIG. 14C is an example according to various embodiments illustrating a CD45-PE channel image of captured CTC and nonspecific captured white blood cells. FIG. 14D is an example according to various embodiments illustrating a merged image of the 3 channels of captured CTC and nonspecific captured white blood cells. FIG. 14E is an example according to various embodiments illustrating a Brightfield image of captured CTC and nonspecific captured white blood cells. CTC is defined as DAPI+, CK+, CD45−; white blood cells is defined as DAPI+, CK−, CD45+. To eliminate false positive signals, various embodiments only consider cytokeratin positive, CD45 negative, DAPI positive (CK+/CD45−/DAPI+) cells as CTCs (FIG. 14A, FIG. 14B, FIG. 14C, and FIG. 14D). White blood cells should be labeled as CK−/CD45+/DAPI+. Any other labeling formats were considered as false positive signals or cell debris. CTCs were detected in all 16 clinical samples ranging from 1 to 15 CTCs/ml. As comparison, the GEM device detected CTCs ranging from 1-10 CTCs/ml.

Comparison of LFAM device and a geometric enhanced microchip (GEM) in CTCs isolation from 16 clinical samples. FIG. 36B is an example according to various embodiments illustrating CTCs per mL enumerated from the LFAM device and GEM device from 16 samples. FIG. 36C is an example according to various embodiments illustrating the average CTCs/mL in the 16 clinical sample in the LFAM device and the GEM chip. From FIG. 36B and FIG. 36C, the LFAM device generally gave higher CTC isolation efficiency compared with the GEM device. Considering that small amount of blood sample consumed by the LFAM device, the LFAM device was very sensitive for detecting CTCs.

Example 3

Geometry Layout of a LFAM Device

The LFAM device according to this example and according to various embodiments included 4 serpentine main channels. An array of in-plane filters is embedded into each serpentine main channel. The main channel height may be 45 µm; the width of the main channel may be 300 µm. The filters share the same height with the main channel, and the filter size may be defined by its width. Therefore, cells only deform in the width direction inside the filter. The filters in each serpentine channel are divided into 5 zones with each zone containing 10 columns of filters. The filter size within the same filter zone may be identical.

Figure 15:
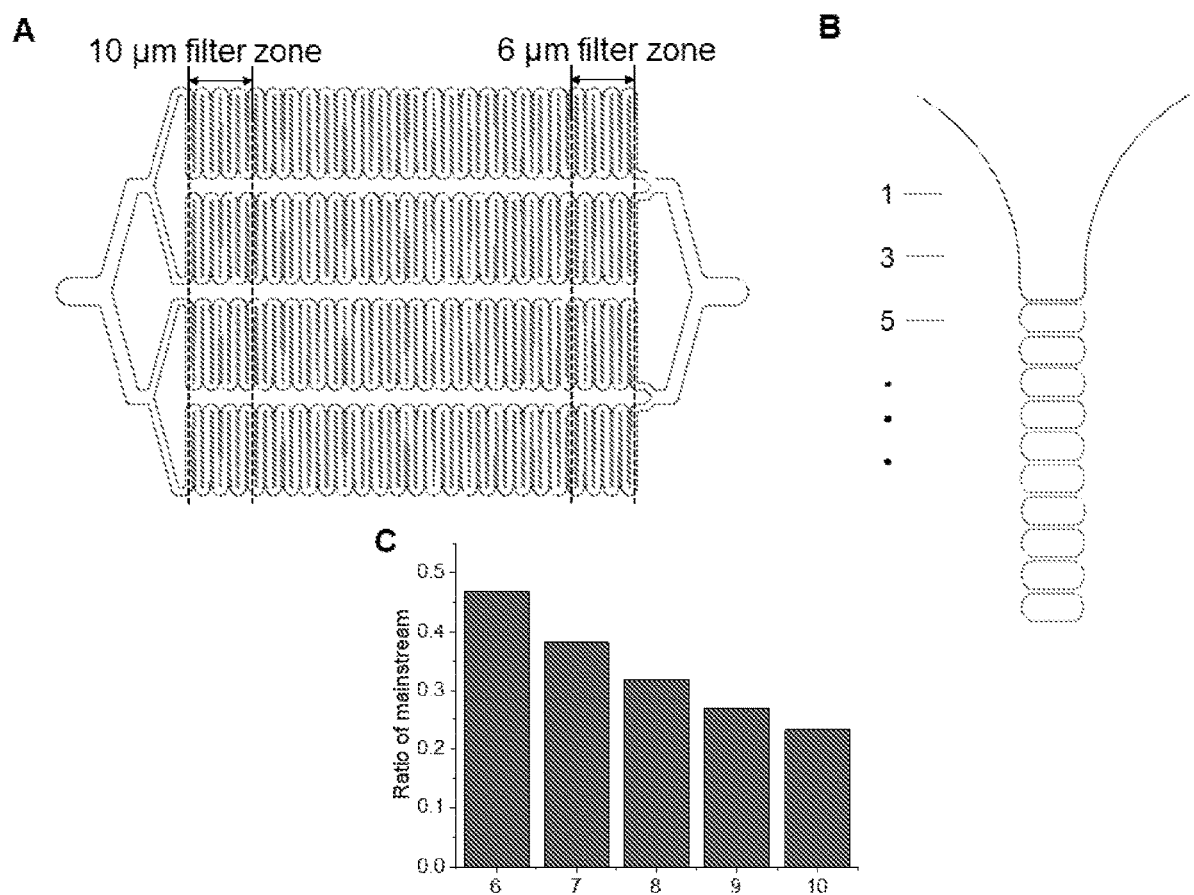
FIG. 15A: is an example according to various embodiments illustrating a schematic diagram of a LFAM device.
FIG. 15B: is an example according to various embodiments illustrating the filters within the same column of the LFAM device according to FIG. 15A.
FIG. 15C: is an example according to various embodiments illustrating mainstream ratio in different filter zones in LFAM device illustrated in FIG. 15A and FIG. 15B.

FIG. 15A is an example according to various embodiments illustrating a schematic diagram of a LFAM device. The overall geometry layout of LFAM device is given in FIG. 15A. It has four serpentine main channels with a filter array imbedded in each main channel. It is divided into 5 zones based on filter size. The 10 µm filter zone (biggest filter) may be located near the inlet. The 6 µm filter zone (smallest filter) may be near the outlet. The decrement in filter size between adjacent zones may be 1 µm.

FIG. 15B is an example according to various embodiments illustrating the filters within the same column of the LFAM device according to FIG. 15A. As shown in FIG. 15B, the filters are designed with decreasing length to produce relatively even flow rates distributed in the filters.

FIG. 15C is an example according to various embodiments illustrating mainstream ratio in different filter zones in LFAM device illustrated in FIG. 15A and FIG. 15B. The filter sizes in different zone are between 6 μm and 10 μm with an increment of 1 μm (FIG. 15A). Different filter zones are distributed in a descending order, with the biggest filters located near the inlet of the LFAM device. Within the same column, the filter length linearly changes from 50 μm to 100 μm (FIG. 15B). Such design produces more evenly distributed flow rates among filters in the same column. The LFAM device has 68 filters in a column and the distance between adjacent filters may be 47 μm. The mainstream ratio increases from 23.2% to 46.9% when the filter size decreases from 10 μm to 6 μm (FIG. 15C), showing that the flow in the LFAM device according to this example has higher velocity components along the main channel direction compared with the LFAM device as illustrated in FIG. 9A.

Figure 16:
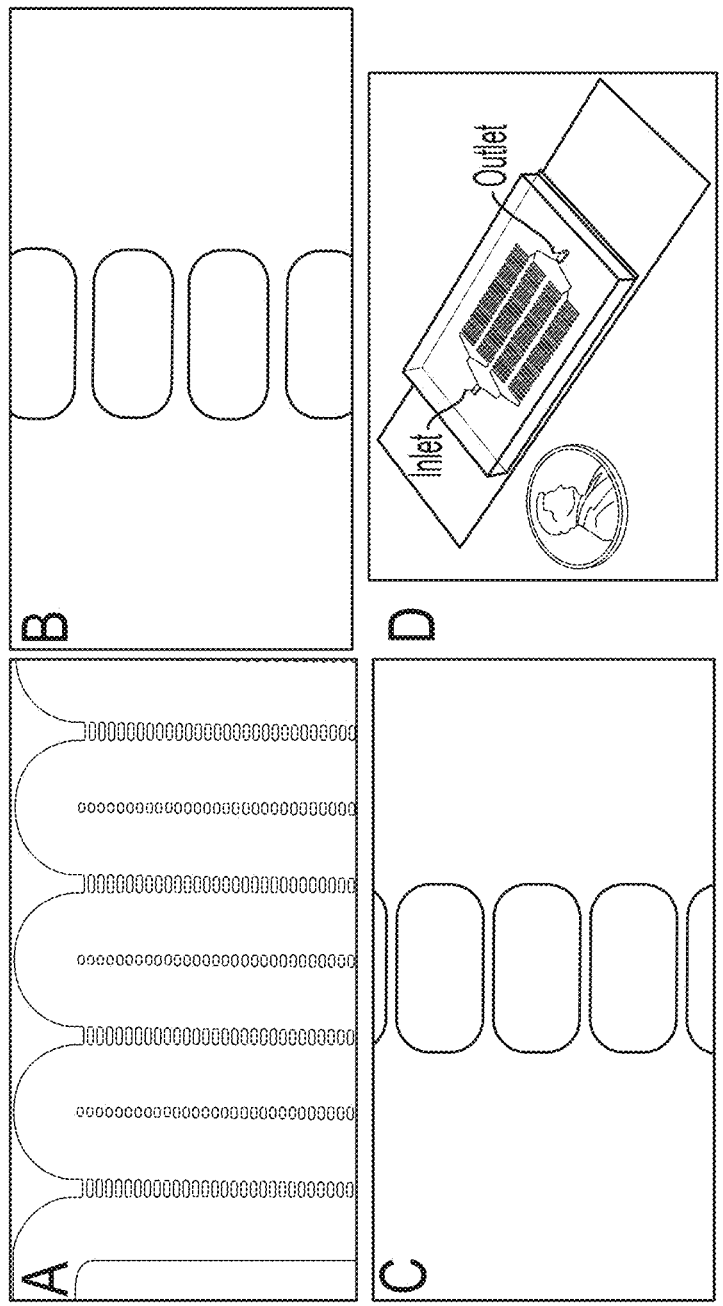
FIG. 16A: is an example according to various embodiments illustrating the serpentine channel of the LFAM device, shown schematically in FIG. 15A, with filters imbedded under 50× magnification.
FIG. 16B: is an example according to various embodiments illustrating the serpentine channel of the LFAM device, shown schematically in FIG. 15A, with 10 μm filter under 400× magnification.
FIG. 16C: is an example according to various embodiments illustrating the serpentine channel of the LFAM device, shown schematically in FIG. 15A, with 6 μm filter under 400× magnification.
FIG. 16D: is an example according to various embodiments illustrating a photograph of the overall PDMS-based LFAM device, shown schematically in FIG. 15A.

FIG. 16A is an example according to various embodiments illustrating the serpentine channel of the LFAM device, shown schematically in FIG. 15A, with filters imbedded under 50× magnification. FIG. 16B is an example according to various embodiments illustrating the serpentine channel of the LFAM device, shown schematically in FIG. 15A, with 10 μm filter under 400× magnification. FIG. 16C is an example according to various embodiments illustrating the serpentine channel of the LFAM device, shown schematically in FIG. 15A, with 6 μm filter under 400× magnification. FIG. 16D is an example according to various embodiments illustrating a photograph of the overall PDMS-based LFAM device, shown schematically in FIG. 15A. The smallest filter size of the LFAM device, according to this example, may be smaller than 10 μm. Therefore, the silicon master of the LFAM device was fabricated using photolithography and DRIE as discussed above. FIG. 16A-16C show the microchannel and filters of the fabricated silicon master. The PDMS-based LFAM device was fabricated by soft lithography using the silicon master, as shown in FIG. 16D.

Cell Capture in Buffer and in Blood

For cell capture in buffer, ~1000 of L3.6 cells were spiked in the 1 ml of DPBS buffer and infused to LFAM device (either functionalized by anti-EpCAM or not). The infusion flow rate varied from 1.8 ml/h to 7.2 ml/h. After sample infusion, LFAM device was washed by infusing 250 μl of DPBS.

Figure 17:
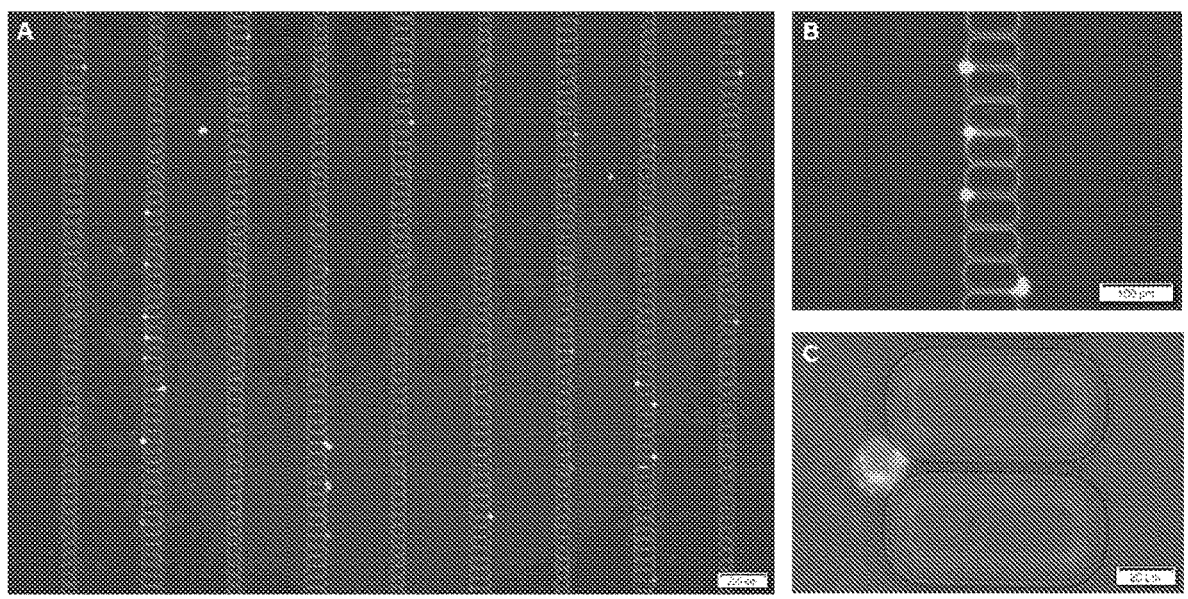
FIG. 17A: is an example according to various embodiments illustrating cells captured in the LFAM device, schematically illustrated in FIG. 15A, without antibody coated at 100× magnification.
FIG. 17B: is an example according to various embodiments illustrating cells captured in the LFAM device, schematically illustrated in FIG. 15A, without antibody coated at 200× magnification.
FIG. 17C: is an example according to various embodiments illustrating cells captured in the LFAM device, schematically illustrated in FIG. 15A, without antibody coated at 400× magnification.

FIG. 17A-17C shows cells captured in the LFAM device without antibody coated. FIG. 17A is an example according to various embodiments illustrating shows cells captured in the LFAM device, schematically illustrated in FIG. 15A, without antibody coated at 100× magnification. FIG. 17B is an example according to various embodiments illustrating shows cells captured in the LFAM device, schematically illustrated in FIG. 15A, without antibody coated at 200× magnification. FIG. 17C is an example according to various embodiments illustrating shows cells captured in the LFAM device, schematically illustrated in FIG. 15A, without antibody coated at 400× magnification.

To comprehensively study the integration of filtration and affinity-based CTC isolation, the LFAM device was used for examination under different conditions. For cell capture based on methods integration, anti-EpCAM was immobilized in the LFAM device following surface modification as discussed above; for cell capture by filtration, the LFAM device was simply passivated with BSA buffer.

Figure 18:
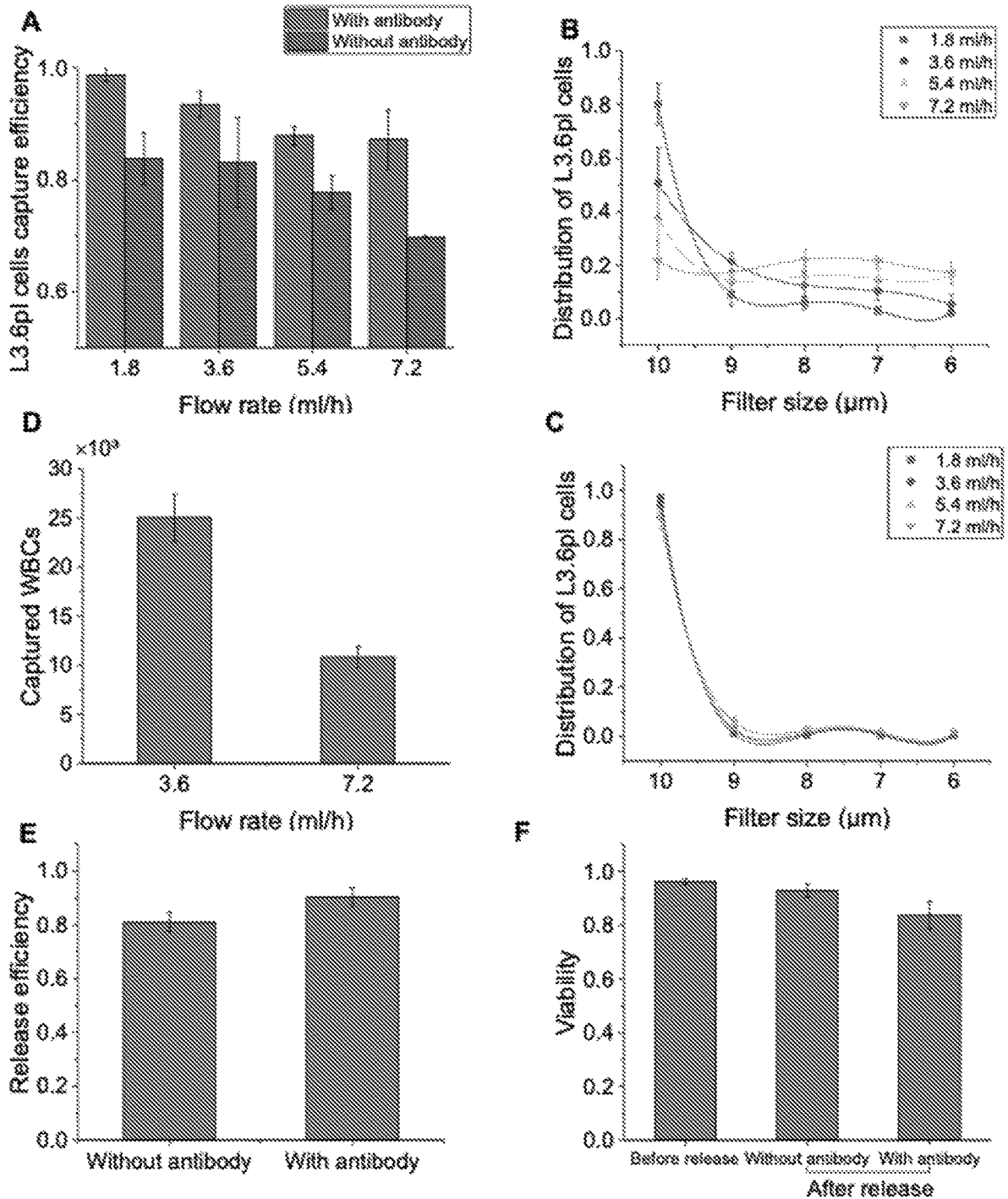
FIG. 18A: is an example according to various embodiments illustrating a comparison in capture efficiency of L3.6pl cells between a LFAM device with antibody and a device without antibody.
FIG. 18B: is an example according to various embodiments illustrating a cell distribution pattern in LFAM without antibody, the Y-axis indicating the percentage of cells captured in each filter zone.
FIG. 18C: is an example according to various embodiments illustrating the cell distribution pattern in LFAM with antibody.
FIG. 18D: is an example according to various embodiments illustrating nonspecific capture of white blood cells in the LFAM device.
FIG. 18E: is an example according to various embodiments illustrating release efficiency of L3.6pl cells from LFAM with or without antibody.
FIG. 18F: is an example according to various embodiments illustrating viability of the released L3.6pl cells.

FIG. 18A is an example according to various embodiments illustrating L3.6pl cells capture efficiency LFAM device, schematically illustrated in FIG. 15A, with or without antibody coated. As shown in FIG. 18A, 83.9±4.6% of L3.6pl cells are captured at 1.8 ml/h. When LFAM device is functionalized with anti-EpCAM, 98.7±1.3% of L3.6pl cells are captured at 1.8 ml/h. The improvement may be more than 10%. The analysis of captured cells distribution clearly indicates the effectiveness of integration of filtration and immunoaffinity based CTC isolation. With filtration only, more than 60% of captured cells are distributed near the inlet (10 μm zone) at 1.8 ml/h.

FIG. 18B is an example according to various embodiments illustrating captured L3.6pl cells distribution in LFAM device, schematically illustrated in FIG. 15A, without antibody coated. FIG. 18C is an example according to various embodiments illustrating captured L3.6pl cells distribution in LFAM device, schematically illustrated in FIG. 15A, with antibody coated. Increasing flow rates largely weakens the distribution peak near the inlet and more cells are captured in the filter zones between 9 μm and 6 μm, as shown in FIG. 18B. More cells squeeze through the 10 μm filters when background pressure and shear force increase at high infusion flow rates. However, when the device is functionalized with anti-EpCAM, more than 90% of captured cells are distributed in the 10 μm filters zone (FIG. 18C) even at a high flow rate 7.2 ml/h, showing that antibodies significantly improve the cell capture capability of the filters through antibody-antigen conjugation. The more deformable L3.6pl cells which might have passed through the 10 μm filters are captured in the 10 μm filter zone due to their EpCAM expressions.

To simulate clinical application of LFAM device, tumor cells spiked in blood samples were used. Healthy donor blood samples were ordered from the Innovative Research, Inc. (MI, USA). 10, 100, 500, or 1000 of L3.6pl cells were spiked in 1 ml of 2-time diluted healthy whole blood (blood/DPBS=1:1) and infused to the anti-EpCAM-coated LFAM device. After sample infusion, the device was also washed with 250 μl DPBS to remove impurities.

After sample processing, the LFAM device was anchored on the stage of the microscope. An Olympus TX71 fluorescence microscope (Olympus America, PA) equipped with a scientific-grade CCD camera (Hamamatsu C4742-80-12AG) was used for device scanning. A whole device scan under bright field was conducted first to acquire an overview of the LFAM device. Then different filter zones were individually scanned under the fluorescence channel. Focusing was manually re-adjusted before scanning each zone to prevent out-of-focus problems. Images from the same filter zone were stitched after scanning and saved as one whole image. Through analyzing the image of an individual zone and compared with the total images of the device, the captured cell distribution pattern in different filter zones was obtained.

We further studied CTC capture in LFAM through force analysis. Considering a cell an elastic sphere, a compression force may be required to deform the cell so that it can squeeze through a filter. The compression force was calculated using the Hertz model (FIGS. 23A and 23B). [6] When the hydrodynamic force a cell experiences overcomes the required compression force, the cell starts to squeeze through the filter. A computational fluid dynamic model (COMSOL Multiphysics) was employed to simulate the hydrodynamic force a CTC experiences. The hydrodynamic force under different flow rates may be compared with the compression force (FIG. 24A, FIG. 24B, FIG. 24C, FIG. 24D, and FIG. 24E). The compression force calculated for WBCs (FIG. 24A) shows that WBCs can squeeze through the filters at these flow rates. CTCs with a diameter bigger than 15 μm can be trapped by the lateral filters at various flow rates. CTCs with a diameter smaller than 15 μm can be compressed into the lateral filter at a high flow rate. The capture of these types of CTCs relies on immunoaffinity. The hydrodynamic force a cell experiences in the filter may then be compared with the bond force between antibodies and the cell (FIG. 25A, FIG. 25B, and FIG. 25C). For tumor cells with high expression level of the biomarker targeted by the antibody, the bond force may be more than 10 times larger than the hydrodynamic force the tumor cell experiences. The force analysis theoretically proves the feasibility of integrating lateral filter arrays with immunoaffinity for CTC isolation.

To test LFAM and verify simulation, L3.6pl cells (metastatic human pancreatic cancer cells) were spiked in Dulbecco's phosphate-buffered saline (DPBS) buffer for performance evaluation. L3.6pl cells express a high level of EpCAM. Devices functionalized with anti-EpCAM were studied and compared to devices without antibody.

FIG. 18A is an example according to various embodiments illustrating a comparison in capture efficiency of L3.6pl cells between a LFAM device with antibody and a device without antibody. FIG. 18B is an example according to various embodiments illustrating a cell distribution pattern in LFAM without antibody, the Y-axis indicating the percentage of cells captured in each filter zone. FIG. 18C is an example according to various embodiments illustrating the cell distribution pattern in LFAM with antibody. FIG. 18D is an example according to various embodiments illustrating nonspecific capture of white blood cells in the LFAM device. FIG. 18E is an example according to various embodiments illustrating the release efficiency of L3.6pl cells from LFAM with or without antibody. FIG. 18F is an example according to various embodiments illustrating viability of the released L3.6pl cells.

As shown in FIG. 18A, without antibody functionalization, the capture efficiency of L3.6pl cells varies from 69.8% to 83.9% at different flow rates. The capture efficiency decreases with the flow rate because of increasing shear-induced hydrodynamic force. [7] When the LFAM device according to various embodiments is functionalized with anti-EpCAM, the capture efficiency may increase by about 10% or more at all flow rates. The capture efficiency may be 98.7±1.2% at 1.8 ml/h. Even at a high flow rate of 7.2 ml/h, the capture efficiency may be 87.2±5.3%, showing that the antibody-functionalized LFAM device maintains high capture efficiency.

The distribution of cells captured in different filter zones indicates the effect of immunoaffinity on cell capture. In a LFAM device without antibody immobilized (FIG. 18B), at the flow rate of 1.8 ml/h, 80.2±7.7% of captured cells are in the 10-μm filter zone. As flow rate increases, more cells are captured downstream (i.e., 9 μm to 6 μm filter zones); only 21.8±7.4% of captured cells are in the 10-μm filter zone when the flow rate may be 7.2 ml/h.

For comparison, in a LFAM device functionalized with anti-EpCAM (FIG. 18C), the captured cell distribution patterns are almost identical for different flow rates. Over 90% of captured cells are distributed in the 10-μm filter zone for all four flow rates. This shows that the functionalization of antibody significantly increases the capability of filters to capture tumor cells.

Figure 28:
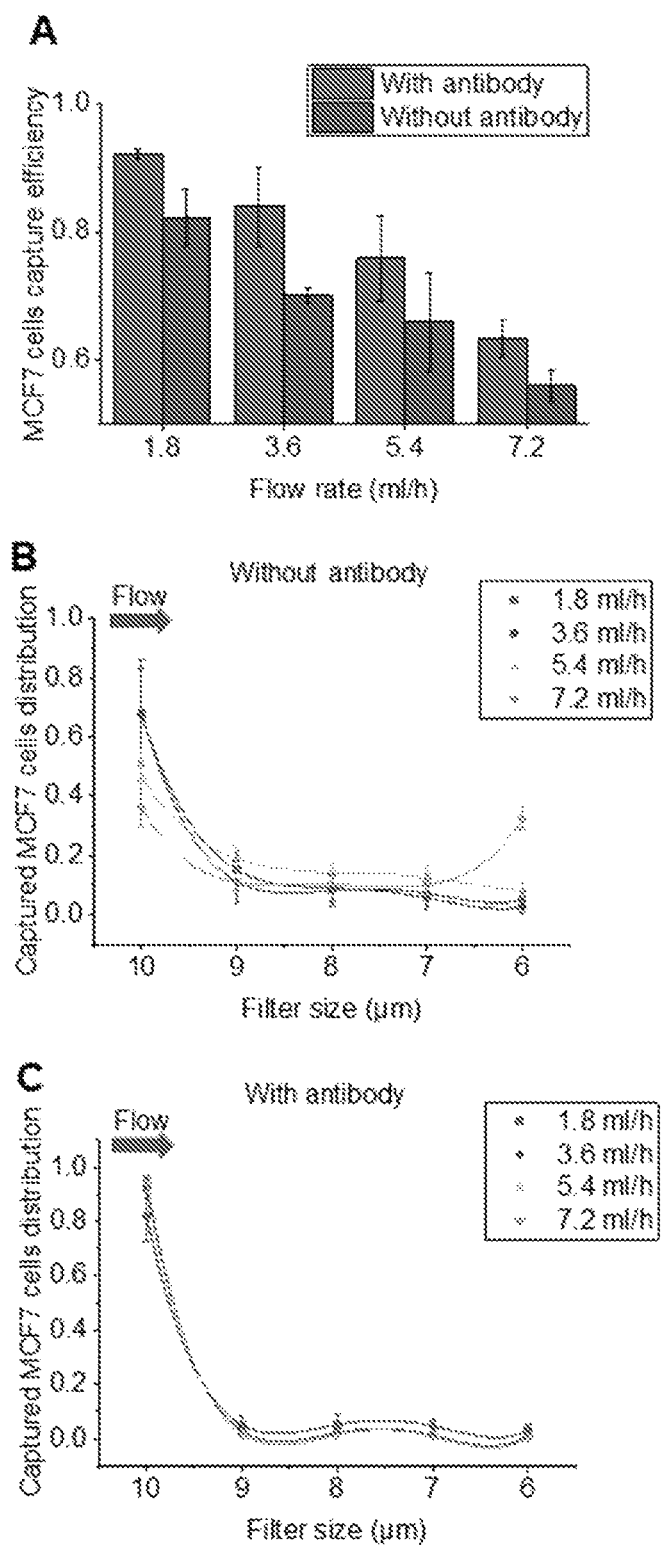
FIG. 28A: is an example according to various embodiments illustrating a comparison of MCF7 cells captured in LFAM with and without antibody.
FIG. 28B: is an example according to various embodiments illustrating MCF7 cell distribution pattern in LFAM without antibody.
FIG. 28C: is an example according to various embodiments illustrating MCF7 cell distribution pattern in LFAM with antibody.

To further demonstrate the advantages of integrating size-based separation with immunoaffinity-based isolation, MCF7 cells (human breast adenocarcinoma cells) were spiked in the buffer and tested in LFAM. Significant improvement in cell capture efficiency was also observed when LFAM was functionalized with anti-EpCAM (FIG. 28A, FIG. 28B, and FIG. 28C). The change of distribution pattern for captured MCF7 cells after antibody functionalization in LFAM was similar to that observed for L3.6pl cells (FIG. 28A, FIG. 28B, and FIG. 28C).

To study nonspecific capture of control cells in LFAM, a mixture containing 1000 L3.6pl cells and $3\times10^6$ WBCs (control cells) were infused to the antibody-functionalized LFAM. FIG. 18D shows the non-specific capture of WBCs in LFAM at a flow rate of 3.6 ml/h and 7.2 ml/h, at a value of $(2.50\pm0.24)\times10^4$ WBCs (or 0.83% of WBCs introduced) and $(1.08\pm0.11)\times10^4$ WBCs (or 0.36%), respectively. The capture efficiency of the target L3.6pl cells are 93.8±1.5% at 3.6 ml/h and 88.5±1.6% at 7.2 ml/h.

The captured L3.6pl cells were then released from LFAM by pumping from the outlet. As shown in FIG. 18E, the cell release efficiency in an antibody functionalized device according to various embodiments may be 90.2±3.5%, which is higher than the corresponding release efficiency of 81.0±3.7% in LFAM without antibody. This result seems to be counter intuitive, but it can be explained by two facts: (1) more than 90% of captured L3.6pl cells are located in the 10-μm filter zone (i.e., near the inlet) of the antibody-functionalized LFAM and they are easier to be pumped out with a reverse flow; and (2) antibody-functionalized LFAM may be treated with a trypsin solution to disassociate EpCAM-antibody bond and the solution may slightly affect the cell membrane structure. FIG. 18F shows that the viability of L3.6pl cells released from LFAM without antibody may be 92.9±2.4%, which is close to the viability of the cells before infusion, 96.1±1.2%. The viability of cells released from the antibody-functionalized device may be 83.8±5.1%; the decrease in viability probably results from the trypsin treatment. The released L3.6pl cells from antibody-functionalized LFAM were re-cultured and proliferated in a petri dish for two weeks (FIGS. 30A, 30B, and 30C).

Figure 20:
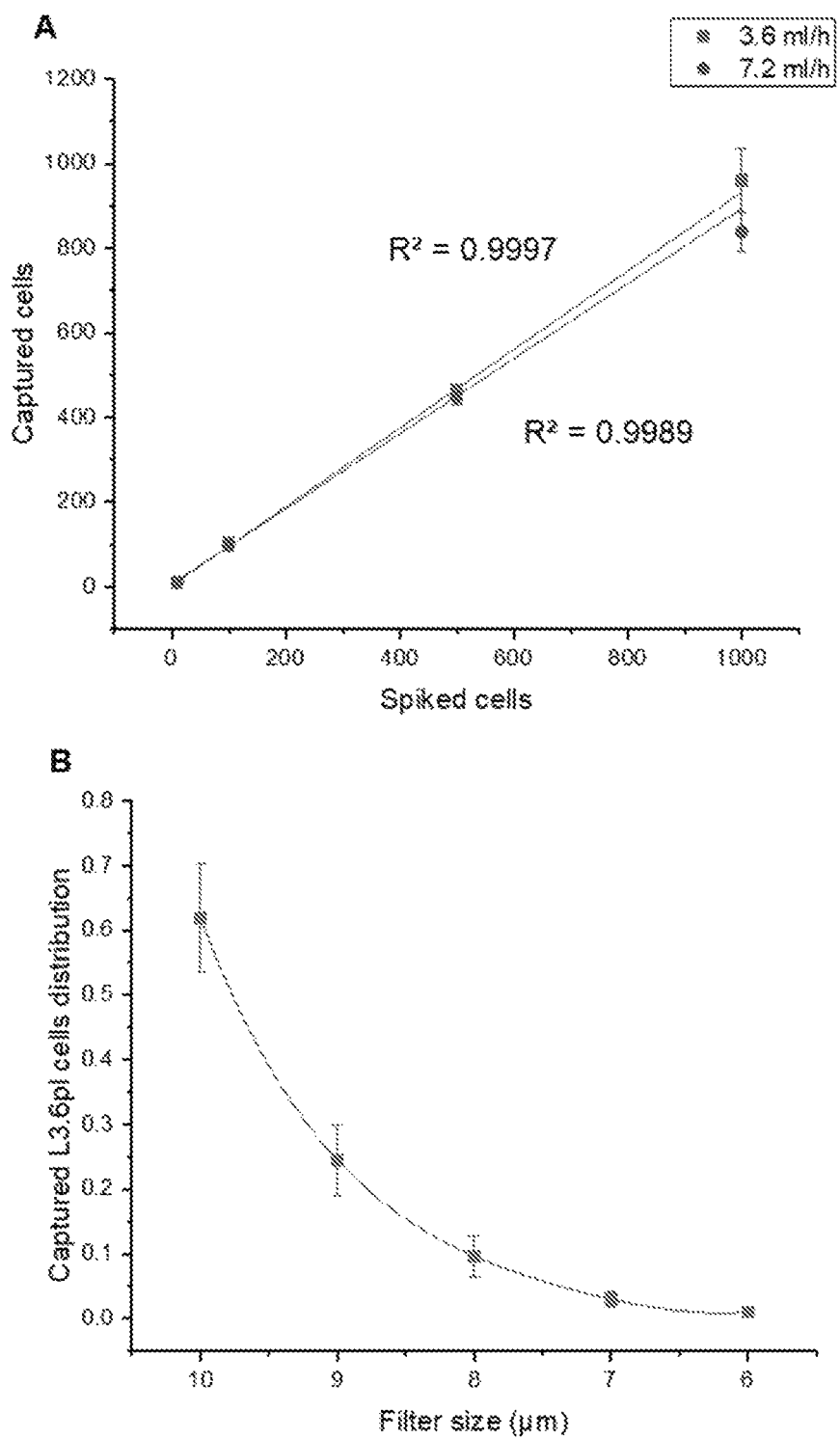
FIG. 20A: is an example according to various embodiments illustrating L3.6pl cells infused to the antibody coated LFAM device.
FIG. 20B: is an example according to various embodiments illustrating captured L3.6pl cells distribution pattern in the LFAM device at 3.6 ml/h.

Before using LFAM for clinical application, the device was studied by spiking 10-1000 of L3.6pl cells into 1 ml of 2-time diluted healthy blood samples and then infusing the sample into the anti-EpCAM-functionalized device. As shown in FIG. 20A, the capture efficiency may be 95.4±1.1% and 88.7±3.5% at a flow rate of 3.6 ml/h and 7.2 ml/h, respectively. The antibody-functionalized LFAM gives sufficiently high capture efficiency even at a high flow rate.

Figure 19:
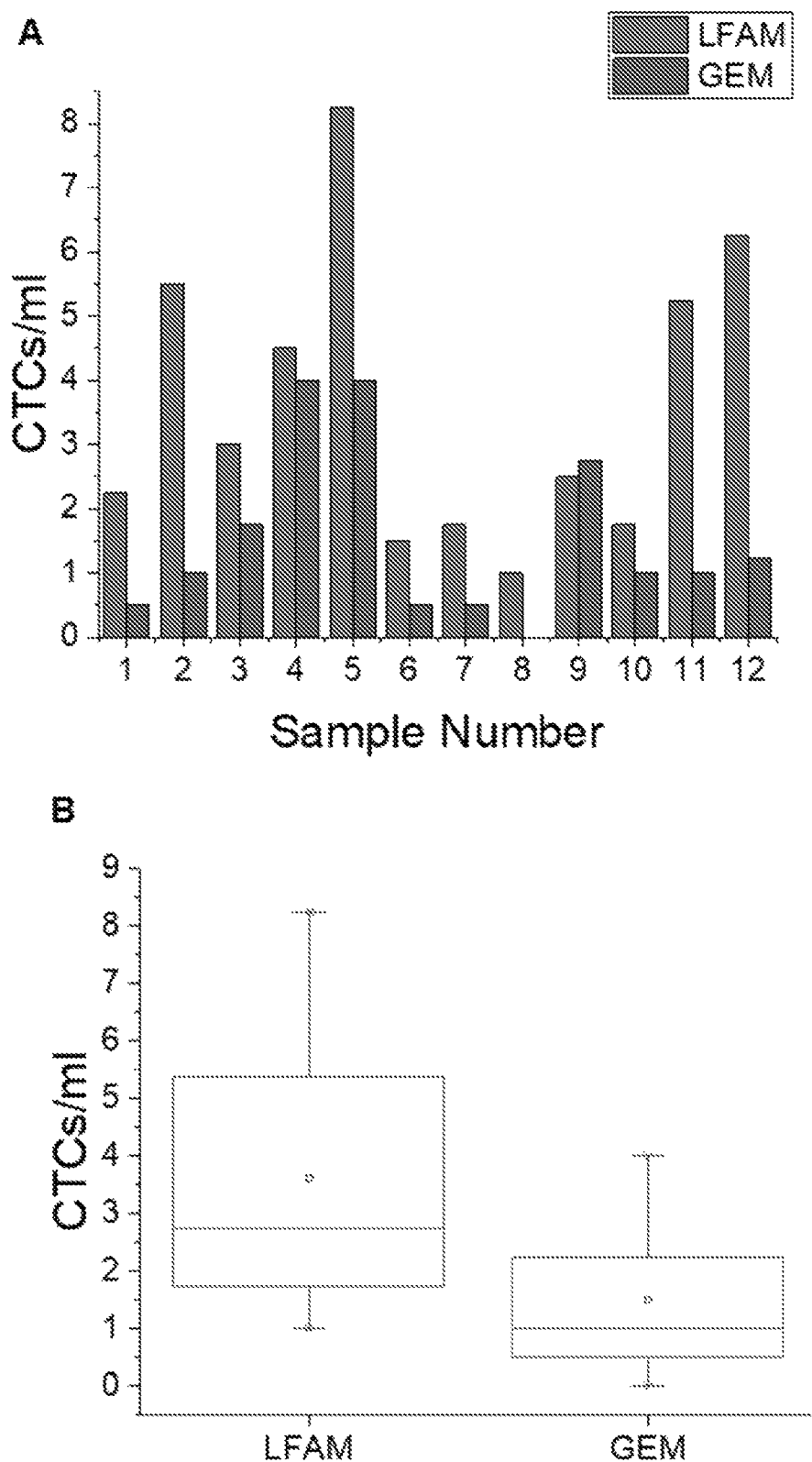
FIG. 19A: is an example according to various embodiments illustrating CTCs isolated from clinical samples using LFAM or GEM.
FIG. 19B: is an example according to various embodiments illustrating the average number of CTCs per ml of blood samples detected using LFAM or GEM.

FIG. 19A is an example according to various embodiments illustrating CTCs isolated from clinical samples using the LFAM device or the geometric enhanced microchip (GEM). FIG. 19B is an example according to various embodiments illustrating the average number of CTCs per ml of blood samples detected using the LFAM or GEM.

Finally, anti-EpCAM functionalized devices were used for CTC isolation from clinical samples. De-identified blood samples were voluntarily collected from patients with metastatic colorectal cancer after approval from the University of Florida institutional review board (IRB). A half of blood sample (4 mL) was diluted with equal volume of DPBS and then processed in the antibody-functionalized LFAM. The equal volume blood dilution was to reduce the blood viscosity and diminish the effect of viscosity variation among different patients, as practiced in commercial Ficoll-Paque process and in the literature. [8] For comparison, the other half of the blood sample was processed under the same condition (e.g., immobilized with anti-EpCAM) using a geometrically enhanced mixing (GEM) device containing herringbone micromixers. [5] Captured cells were fixed with 4% paraformaldehyde (PFA) and permeabilized with Triton X-100. Three reagents, 4',6-diamidino-2-phenylindole (DAPI), anti-cytokeratin (CK) labelled with fluorescein isothiocyanate (FITC), and anti-CD45 labelled with phycoerythrin (PE), were used to interrogate the cells captured. DAPI+/CK+/CD45− cells were considered CTCs. A total of 12 clinical samples were processed. CTCs were detected in 12/12 patients using LFAM and 11/12 using GEM. LFAM generally gives better CTC capture efficiency than GEM, as shown in FIG. 19A. Their box plots are given in FIG. 19B, showing an average of 3.2 CTCs/ml with a range of 1-8.25 CTCs/ml using LFAM, and an average of 1.3 CTCs/ml with a range of 0-4 CTCs/ml using GEM. The difference in the CTC number between LFAM and GEM is statistically significant ($p=0.00224$).

Nonspecific capture of WBCs in LFAM was also studied. About 12,100 to 64,300 WBCs per device were observed, corresponding to 0.078% to 0.41% capture efficiency. All captured cells were then released from LFAM by using a reverse flow. CTCs were released 100% and WBCs were released between 55.6% to 79.1%.

In summary, integration of size-based separation with immunoaffinity-enabled isolation has produced high CTC capture efficiency. The flow pattern in LFAM was simulated and the device design, according to various embodiments, was then optimized. The comparison studies suggest that the antibody-functionalized LFAM has better performance than the device based on tumor cell's size only (i.e. without antibody). In addition, the antibody-functionalized LFAM shows high cell purity and viability, with a greater potential for clinical applications than those devices based on immunoaffinity only. Future studies will focus on in-depth analysis of CTCs isolated using next-generation sequencing and modern single-cell technologies, as well as on clinical utilities such as anticancer treatment monitoring.

For spiked blood sample study, 10-1000 of L3.6pl cells were spiked into 1 ml 2-time diluted healthy whole blood and infused to the anti-EpCAM coated LFAM device at 3.6 ml/h and 7.2 ml/h.

FIG. 20A is an example according to various embodiments illustrating 0, 100, 500, 1000 of L3.6pl cells were infused to the antibody coated LFAM device. The infused flow rates are 3.6 ml/h and 7.2 ml/h. FIG. 20B is an example according to various embodiments illustrating captured L3.6pl cells distribution pattern in the LFAM device at 3.6 ml/h. The capture efficiency may be 95.4±1.1% and 88.7±3.5% (FIG. 20A). The captured cell distribution pattern at 3.6 ml/h is generally agreed with the distribution pattern of pure cell line, as shown in FIG. 20B. Lower distribution ratio (61.8%) in the 10 μm filter zone and higher distribution ratio in 9 μm and 8 μm filter zones reflects the influence of normal blood cells on the target cell capture in the filters. The antibody-coated LFAM device, according to various embodiments, gives sufficiently high CTC capture efficiency even at a high flow rate.

Example 4

Experimental Procedures

Device Fabrication and Preparation

To fabricate a silicon master, a bright field chrome mask was first created with a resolution of 1 μm using a Heidelberg laser writer (Heidelberg Instruments Inc., MA). The pattern on the mask was transferred to a 2-μm-thick of AZ1512 photoresist (Integrated Micro Materials, TX) on a silicon wafer by photolithography. Deep reactive-ion etching (DRIE) was then used to etch the silicon. Using the silicon master, a polydimethylsiloxane (PDMS) substrate was fabricated using soft lithography. The PDMS substrate was then bonded with a glass slide after being treated with UV-Ozone for 5 minutes.

An LFAM device was first filled with 99% ethanol to exhaust air in microchannels, followed by washing using Dulbecco's phosphate buffered saline (DPBS; Fisher Scientific, Hampton, NH). For size-based isolation of tumor cells, the device was passivated with DPBS containing 1% BSA (bovine serum albumin). For immunoaffinity capture combined with size-based isolation, the device was functionalized with anti-EpCAM using the following protocol. One channel-volume (~50 μl) of 1 mg/ml avidin solution was introduced to the device, followed by incubation for 15 minutes. Avidin was immobilized on the device surfaces by physical adsorption and the extra avidin solution was removed by washing the device with DPBS. Then one channel volume of 10 μg/ml biotinylated anti-EpCAM solution was introduced to the device and incubated for 15 minutes, followed by washing and passivation with 1% BSA in DPBS.

Cell Culture and Sample Preparation

Breast cancer cell line, MCF7, was obtained from Dr. Carlos Rinaldi at Department of Chemical Engineering in University of Florida (UF) and it was originally purchased from ATCC. Pancreatic cancer cell line, L3.6pl, was obtained from Dr. Jose Trevino (Department of Surgery, UF) and its detail has been previously reported. [5] These cell lines were cultured using DMEM (ATCC) supplemented with 10% fetal bovine serum (FBS; GIBCO) and 100 units/ml penicillin-streptomycin (Cellgro, Manassas, Va.). The cell culture was carried out at 37 with 5% of $CO_2$. Before experiments, cells were harvested with 0.25% trypsin-EDTA (GIBCO, Fisher Scientific), neutralized with whole growth medium, and resuspended in DPBS. These cells were stained with Vybrant dyes (Thermo Fisher Scientific, NH) by following the manufacturer's instruction. The dyed cells were then rinsed with DPBS before spiking into either DPBS buffer or blood samples.

Tumor Cell Capture in Devices

For samples in a buffer, 1000 cells (either L3.6pl cells or MCF7 cells) were spiked in 1 ml of DPBS buffer. The infusion flow rate of the sample into the device varied from 1.8 ml/h to 7.2 ml/h. After sample infusion, the device was washed by infusing 250 pl of DPBS. For samples in blood, healthy blood samples were purchased from the Innovative Research, Inc. (MI, USA). A total of 10, 100, 500, 1000 L3.6pl cells were spiked in 1 ml of 2-time diluted blood (blood:DPBS=1:1) and the resulting samples were infused to the device. Fluorescence signals of tumor cells captured in the device were collected using an Olympus IX71 fluorescence microscope (Olympus America, PA) equipped with a scientific-grade CCD camera (Hamamatsu C4742-80-12AG).

Release of Captured Tumor Cells

For devices not functionalized with antibody, DPBS was pumped into the device from the outlet at a high flow rate, 18 ml/h, and the released L3.6pl cells were collected from the inlet. For devices functionalized with antibody, the captured L3.6pl cells were first trypsinized with one channel-volume of 0.25% trypsin-EDTA for 10 minutes, followed by pumping DPBS from the outlet at 18 ml/h. The viability of released L3.6pl cells were determined by staining with 4% Trypan blue (Fisher Scientific, NH) by following the manufacturer's instruction.

Clinical Samples

Blood samples were collected from patients with metastatic colorectal cancers at UF Health Shand's Hospital. According to the protocol approved by the UF institutional review board (IRB), all specimens were processed within four hours after blood draw. Before clinical sample arrival, two LFAM devices and two geometrically enhanced mixing (GEM) chips[5] were functionalized with anti-EpCAM and passivated with 1% BSA solution as discussed above. The clinical samples were 2-time diluted (blood:DPBS=1:1) and infused to the antibody functionalized device at 3.6 ml/h. A total of 8 mL of diluted clinical samples were processed by two LFAM devices in parallel (i.e., 4 mL for each device) and the same amount of diluted clinical samples were processed by two GEM chips in parallel. After infusion, 9-channel volume of DPBS were infused to each device to wash away impurities. Then one-channel volume of 4% paraformaldehyde (PFA) solution was introduced to the device and incubated for 10 minutes for cell fixation. After DPBS washing, one-channel volume of 0.2% Triton X-100 solution was introduced to the device and incubated for 10 minutes for cell membrane permeabilization. After washing, one-channel volume of a mixture containing 10 g/mL anti-CD45-PE, 10 g/mL anti-cytokeratin-FITC and 500 nM DAPI was introduced to the device and incubated for staining for 30 minutes. After washing, the device was mounted at the stage of the fluorescence microscope for CTC enumeration. Cells that are DAPI+, CD45−, CK+ are counted as CTCs. Other cells such as white blood cells (DAP+, CD45+, CK−), red blood cells (DAPI−), or others (e.g. triple positive) are excluded.

To release captured CTCs in LFAM, the device was first trypsinized by one-channel volume of 0.25% trypsin-EDTA for 15 minutes, followed by pumping 600 μL of DPBS from the outlet at 18 ml/h.

Results and Discussion

Device Layout

Figure 21:
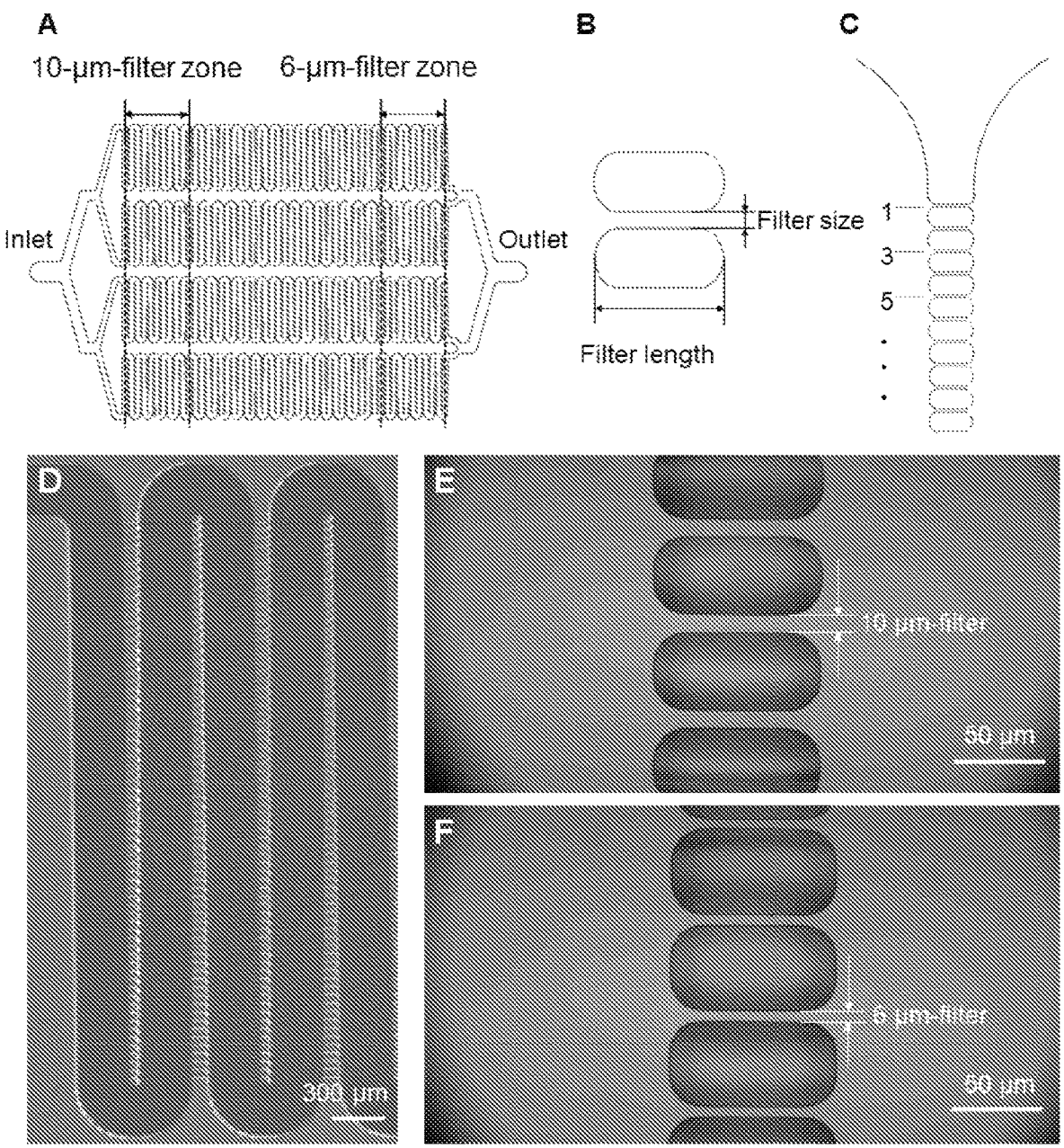
FIG. 21A: is an example according to various embodiments illustrating a layout of a LFAM device having four serpentine main channels with filter arrays embedded in each main channel.
FIG. 21B: is an example according to various embodiments illustrating a filter is defined by the gap between two obstacles.
FIG. 21C: is an example according to various embodiments illustrating the distribution of filters in the same column.
FIG. 21D: is an example according to various embodiments illustrating an image of the silicon master showing a serpentine main channel with lateral filters.
FIG. 21E: is an example according to various embodiments illustrating a photograph of 10-μm filters.
FIG. 21F: is an example according to various embodiments illustrating a photograph of 6-μm filters.

FIG. 21A is an example according to various embodiments illustrating a layout of a LFAM device having four serpentine main channels with filter arrays embedded in each main channel. It is divided into 5 zones based on filter size. The 10 μm-filter zone (the biggest filter size) may be located near the inlet. The 6-μm filter zone (the smallest filter size) may be near the outlet. The decrement in the filter size between adjacent zones may be 1 μm. FIG. 21B is an example according to various embodiments illustrating a filter may be defined by the gap between two obstacles. The filter size may be the smallest width of the filter. The filter length may be the length of the obstacle. FIG. 21C is an example according to various embodiments illustrating the distribution of filters in the same column. The filters with a decreasing length produce relatively even flow rate distribution in the same column. FIG. 21D is an example according to various embodiments illustrating an image of the silicon master showing a serpentine main channel with lateral filters. FIG. 21E is an example according to various embodiments illustrating a photograph of 10-μm filters. FIG. 21F is an example according to various embodiments illustrating a photograph of 6-μm filters.

The LFAM device, according to various embodiments, includes 4 serpentine main channels. An array of in-plane filters may be embedded into each main channel, as shown in FIG. 21A. The depth of the main channel may be 45 μm and the width may be 300 μm. The filters share the same depth with the main channel. The filter size may be defined by the smallest width of the space, as illustrated in FIG. 21B. The filter array may be divided into five zones based on filter size. The filter size in different zones changes from 10 μm to 6 μm with a decrement of 1 μm. The 10 μm-filter zone may be located near the inlet of LFAM. Each zone includes 10 columns of filters with an identical filter size. Each column includes 68 lateral filters. The filter length in each column linearly decreases from 100 μm to 50 μm (FIG. 21C). Such design produces more evenly distributed flow rates among filters in the same column (more discussion in the next section). A picture of a serpentine main channel containing 4 columns of filters is shown in FIG. 21D while a close-up view of 10-μm filters and 6-μm filters is in FIG. 21E and FIG. 21F.

Streamline Pattern Simulation

A theoretical model was developed to simulate the flow pattern in the LFAM device. The flow pattern in LFAM is analogous to an electrical circuit network. The basic components of the circuit network are three types of hydrodynamic resistors (FIG. 5): main channel sections ($R_c$), channel elbows ($R_n$) and filters ($R_f$). $R_e$ is defined as the small section of the main channel connecting two neighbouring filters. $R_n$ is defined as the elbow that is in parallel with the neighbouring filter. As shown in FIG. 6, filters in the adjacent columns are distributed in a reversed order. Accordingly, the flows in the adjacent columns should also be distributed in a reversed order. Considering the total infusion flow rate as I, using the Kirchhoff's current law (KCL):

$$I_1 + I_2 + I_3 + \ldots + I_{n-2} + I_{n-1} + I_n = I \quad (1)$$

Because flows in adjacent columns are distributed in a reversed order, using the Kirchhoff's voltage law (KVL):

$$R_f(k)I_k = R_f(k+1)I_{k+1} + 2R_e[(I_n + I_{n-1} + \ldots + I_{n-k+1}) - (I_1 + I_2 + \ldots + I_k)] \quad (2)$$

The hydrodynamic resistance of each component was simulated using COMSOL Multiphysics. Given certain flow rate, the pressure drop through the component was simulated, as shown in FIG. 7. Using ΔP=RI, the hydrodynamic resistance of the component was calculated. To ensure the accuracy of the hydrodynamic resistance simulated using COMSOL, a single flat channel was simulated, and the simulated result was compared with hydrodynamic resistance calculated by a widely used formula given below[9]

$$R = \frac{12\mu L}{wh^3\left(1 - \frac{0.63h}{w}\right)} \text{ for } h \ll w \quad (3)$$

where μ is the dynamic viscosity of the fluid; L is the length of the channel; w is the width of the channel; h is the height of the channel. The difference between the simulation and calculation methods is 2.2%, indicating the accuracy of the COMSOL simulation.

FIG. 5 Circuit network representation of LFAM. Three basic components include main channel sections ($R_c$), channel elbows ($R_n$) and filters ($R_f$). FIG. 6 Interconnection of filters. Filters from the same column are connected across a main channel section. The filters in the adjacent columns are distributed in a reversed order. Within the same column, the filter located farthest from the channel elbow experiences the maximum pressure drop and the channel elbow experiences the minimum pressure drop. (C) The pressure drop across different basic components were simulated by COMSOL.

Figure 22:
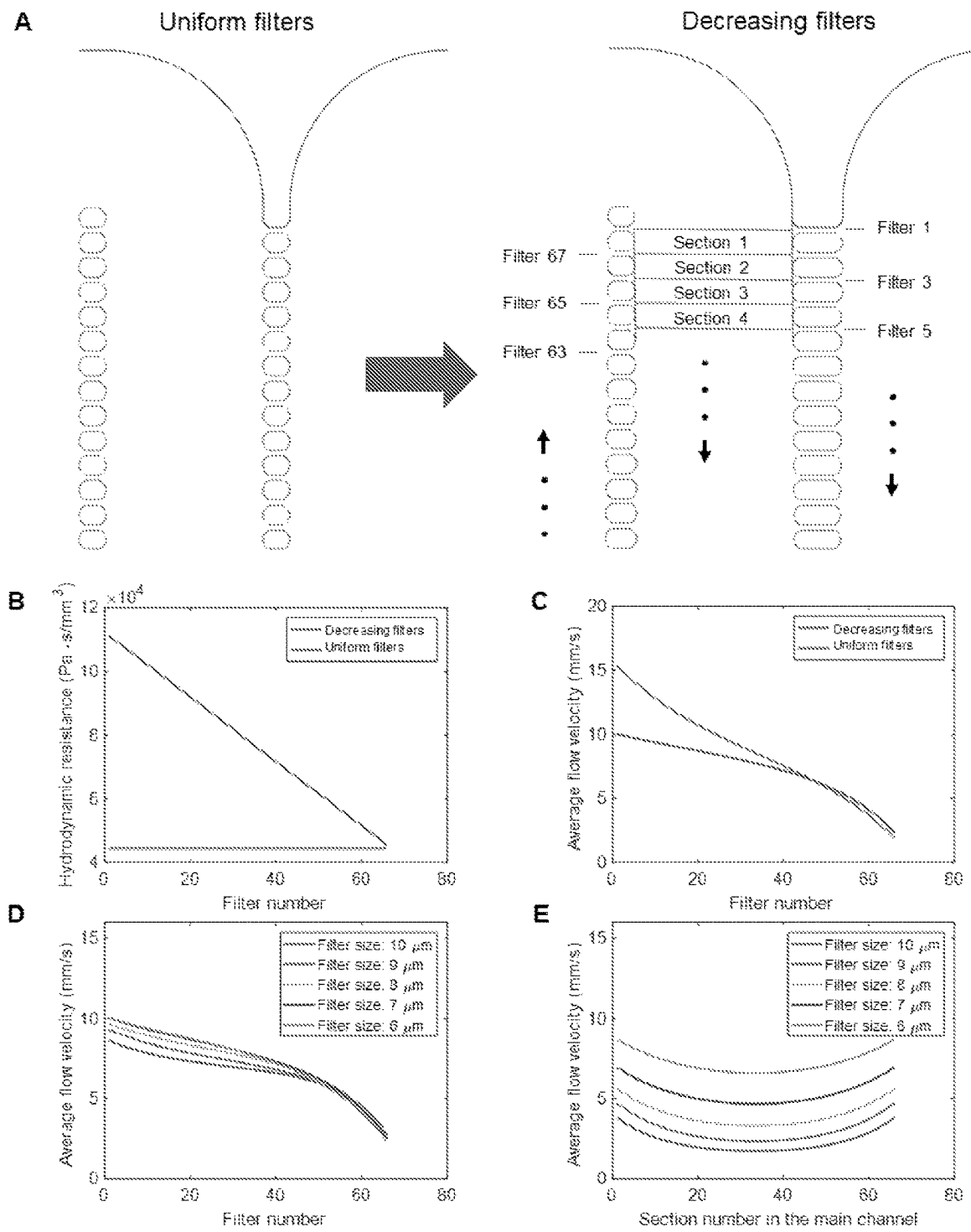
FIG. 22A: is an example according to various embodiments illustrating uniform filters and filters with decreasing lengths (decreasing filters)
FIG. 22B: is an example according to various embodiments illustrating hydrodynamic resistance comparison between uniform filters and filters with decreasing filter length in the same column.
FIG. 22C: is an example according to various embodiments illustrating the average flow velocity distribution along filters in the column with 6-μm-filters at an infusion flow rate of 3.6 ml/h.
FIG. 22D: is an example according to various embodiments illustrating average flow velocity distribution along the same column for different filter zones when the design of decreasing filter length was used.
FIG. 22E: is an example according to various embodiments illustrating the average velocity along the main channel for different filter zones.

The pressure drop of filters embedded in the serpentine main channel is dependent on their locations. For filters in the same column, the closer to the elbow the filter is, the smaller the pressure drops along the filter (FIG. 6). To obtain relatively even flow rate distribution among the same column of filters, a column of filters was designed with linearly decreasing hydrodynamic resistances, as shown in FIG. 22A. From Equation 3, hydrodynamic resistance is proportional to the length of the filter. Therefore, the filter length linearly decreasing by ΔL along the column will produce a serial of filters with linearly decreased hydrodynamic resistance. Considering the hydrodynamic resistance of the Filter 1 (length $L_0$) being simulated as $R_0$, the hydrodynamic resistance of the Filter k in the same column can be calculated as $$R_f(k) = \left[1 - (k-1)\frac{\Delta L}{L_0}\right]R_0 \quad (4)$$

FIG. 22A is an example according to various embodiments illustrating uniform filters and filters with decreasing lengths (decreasing filters). FIG. 22B is an example according to various embodiments illustrating hydrodynamic resistance comparison between uniform filters and filters with decreasing filter length in the same column. FIG. 22C is an example according to various embodiments illustrating the average flow velocity distribution along filters in the column with 6-μm-filters at an infusion flow rate of 3.6 ml/h. FIG. 22D is an example according to various embodiments illustrating average flow velocity distribution along the same column for different filter zones when the design of decreasing filter length was used. FIG. 22E is an example according to various embodiments illustrating the average velocity along the main channel for different filter zones.

The filters with length linearly decreasing from 100 μm to 50 μm were compared with filters with uniform length of 50 μm. FIG. 22B shows the hydrodynamic resistance comparison between the uniform filters and the linearly decreasing filters along the filter number in the same column. The introduction of linearly decreasing filters leads to more evenly flow distribution within the column. FIG. 22C shows the average flow velocity distribution among filters with decreasing length in comparison with uniform filters, at a flow rate of 3.6 ml/h. The change in average flow velocity among filters with decreasing filter length is much less than that among uniform filters. The average flow velocity for Filter 1 reduces by 34.6% after using the design with decreasing filter length. The average flow velocity distribution among filters in the same column for different filter zones at a flow rate of 3.6 ml/h is given in FIG. 22D. The average flow velocity for Filter 1 from 10-μm-filter zone to 6-μm-filter zone changes from 8.9 mm/s to 10.5 mm/s, with a difference of 18.0%. Accordingly, average velocity along the main channel in different filter zones are shown in FIG. 22E. The average flow velocity distribution along the main channel is symmetric with reference to the middle section (Section 34). The maximum average velocity located near the channel elbow (Section 1), changes from 4.2 mm/s in the 10-μm-filter zone to 8.6 mm/s in the 6-μm-filter zone, with a difference of 104.8%. The primary reason for the significant increase in flow velocity along the main channel is that the ratio of fluid through the main channel increases dramatically due to the decrease in filter size.

A key objective of LFAM design is to guarantee the interaction between all cells and filters. All cells flowing through LFAM should cross certain filters to prevent possible cell loss. To track potential paths of cells, the streamline pattern in LFAM was studied. Since the Reynold's number in the channel is always less than 1.18 (depending on the flow rate used), laminar flow is dominant. Through the mainstream ratio, the streamline pattern in LFAM was predicted. The mainstream ratio is defined as the ratio of the flow through the elbow to the flow through the whole column as discussed in the main text. Since streamlines will not intersect, the streamlines through the channel elbow determines its affected zone downstream. This zone is considered as the mainstream zone. As shown in FIG. 7A, the mainstream zone expands as the mainstream ratio increases. The bigger the mainstream zone, the larger the velocity component along the main channel. However, the mainstream ratio cannot exceed 50%. Otherwise, the adjacent elbows will create an overlapped zone in the main channel. Cells in the overlapped zone will stay int the main channel without passing any filters.

The mainstream ratio determines the range of the mainstream zone. FIG. 7A When the mainstream ratio is <<50%, the mainstream zone covers only a few filters in the next column. The velocity component in the main channel direction is very small. FIG. 7B When mainstream ratio is sufficiently bigger but still smaller than 50%, more downstream filters are affected by the mainstream zone. FIG. 7C When the mainstream ratio=50%, the mainstream zone covers all filters in the next column. The velocity component in the main channel direction is maximum in the applicable range. FIG. 7D When the mainstream ratio is >50%, the mainstream zones in the neighboring columns have an overlapped zone. Cells flowing in the overlapped zone will stay in the main channel without interacting with filters, which is not suitable for CTC isolation.

Force Analysis

A flow-structure interaction (FSI) model was built using COMSOL Multiphysics to simulate the hydrodynamic force a cell experiences when interacting with a filter. The cell is considered a sphere. Under an applied pressure, the cell can be trapped by the filter, or squeeze through the filter.

Two different situations are considered when a cell interacts with the filter. FIG. 23A is an example according to various embodiments illustrating a CTC cell coming into contact with the filter without deformation. FIG. 23B is an example according to various embodiments illustrating a CTC cell fully compressed in the filter. FIG. 23C is an example according to various embodiments illustrating the hydrodynamic force a cell experiences near the entrance of a lateral filter. FIG. 23D is an example according to various embodiments illustrating the hydrodynamic force a cell experiences near the entrance of a lateral filter. FIG. 23E is an example according to various embodiments illustrating the deformation of the cell from the initial state (circular dashed line) to the fully deformed state (represented by solid lines). To simplify the complicated cell deformation, two extreme cases are simulated: (1) the cell in contact with the filter inlet without deformation (FIG. 23A) and (2) the cell fully compressed into the filter (FIG. 23B). A constant pressure is set at the entrance of the filter and zero pressure is at the end of the filter. The pressure value is simulated using lumped element model discussed above. The flow field and shear stress distribution around the cell are simulated using the FSI model (FIG. 23C and FIG. 23D). The hydrodynamic force the cell experiences can be obtained from the simulation.

When a cell comes into contact with the filter, the hydrodynamic force it experiences determines whether it is trapped. Without considering immunocapture, if the hydrodynamic force (FIG. 23C and FIG. 23D) exceeds the force required to compress the cell into the filter, the cell may squeeze through the filter. The compression force was calculated using the Hertz model (FIG. 23E). [6] It is given as $$F_{compression} = \frac{4E_{cell}}{3(1-v^2)}\sqrt{D_{cell}/2}\left(\frac{D_{cell} - W_{deformed}}{2}\right)^{3/2} \quad (5)$$

where $E_{cell}$ is the Young's modulus of the cell; $D_{cell}$ is the cell diameter; $W_{deformed}$ is the filter size; v is Poisson's ratio.

Figure 24:
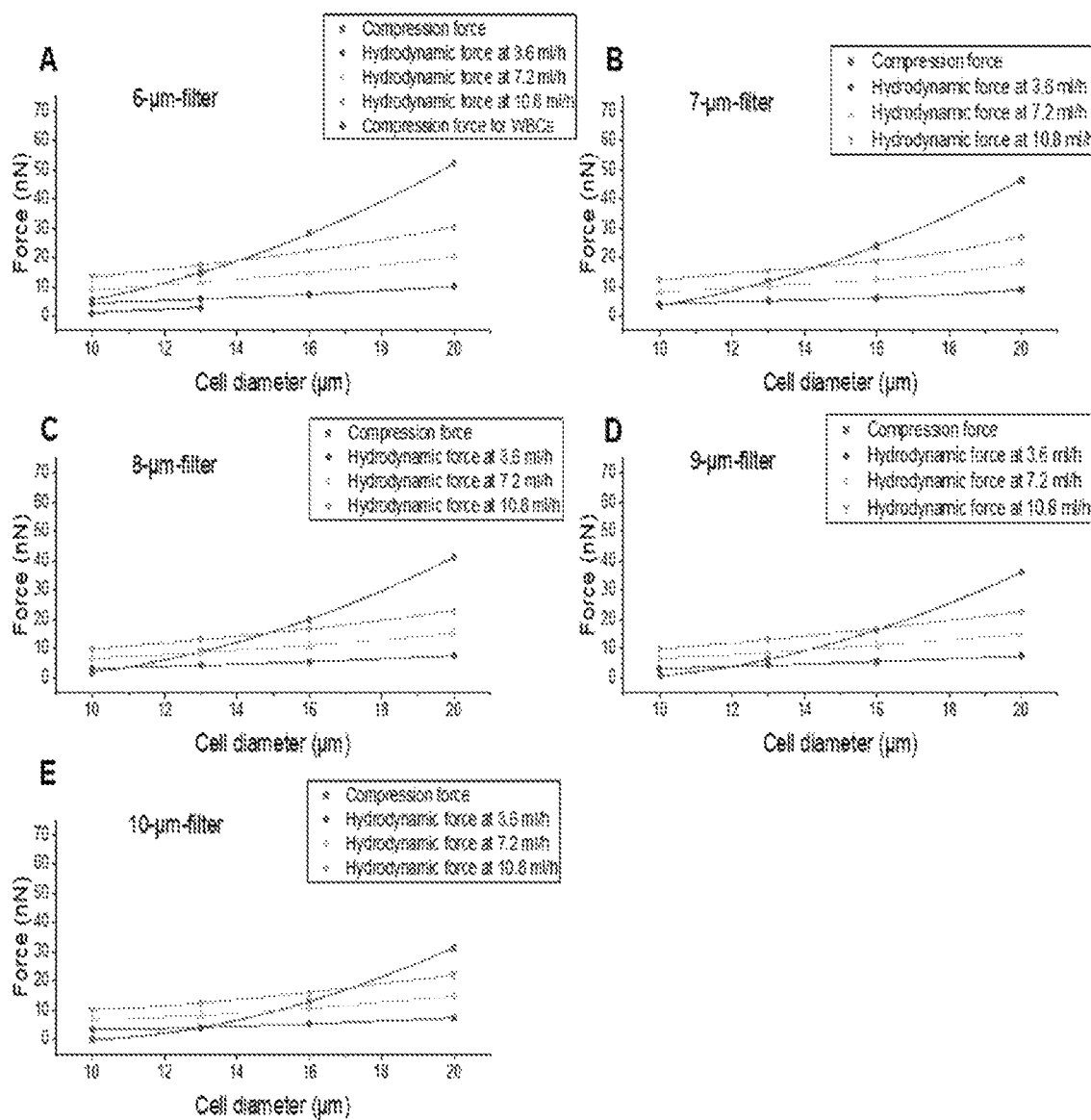
FIG. 24A: is an example according to various embodiments illustrating a plot of cell compression force and hydrodynamic force of tumor cells of various diameters in a 6-μm-filter zone.
FIG. 24B: is an example according to various embodiments illustrating a plot of cell compression force and hydrodynamic force of tumor cells of various diameters in 7-μm-filter zone.
FIG. 24C: is an example according to various embodiments illustrating a plot of cell compression force and hydrodynamic force of tumor cells of various diameters in 8-μm-filter zone.
FIG. 24D: is an example according to various embodiments illustrating a plot of cell compression force and hydrodynamic force of tumor cells of various diameters in 9-μm-filter zone.
FIG. 24E: is an example according to various embodiments illustrating a plot of cell compression force and hydrodynamic force of tumor cells of various diameters in 10-μm-filter zone.
Figure 25:
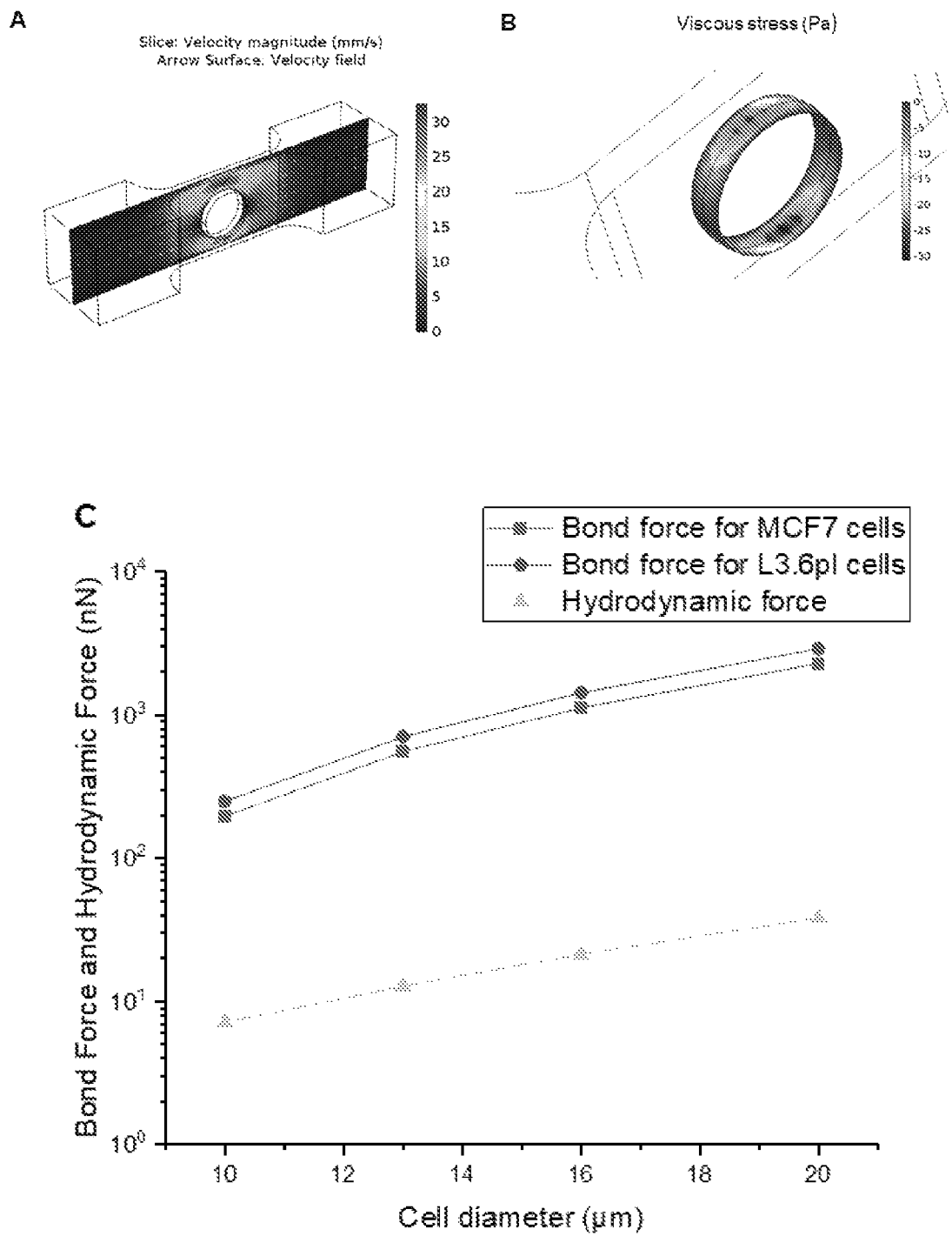
FIG. 25A: is an example according to various embodiments illustrating velocity distribution in a 7-μm filter when a cell is fully compressed.
FIG. 25B: is an example according to various embodiments illustrating the viscous stress distribution around the cell.
FIG. 25C: is an example according to various embodiments illustrating a comparison between the bond force and hydrodynamic force a cell experiences at a flow rate of 3.6 ml/h.

FIG. 24A, FIG. 24B, FIG. 24C, FIG. 24D, and FIG. 24E provide a comparison between compression force and hydrodynamic force of a tumor cell in 5 different filter zones. FIG. 24A is an example according to various embodiments illustrating showing a plot of cell compression force and hydrodynamic force of tumor cells of various diameters in a 6-μm-filter zone. FIG. 24B is an example according to various embodiments illustrating showing a plot of cell compression force and hydrodynamic force of tumor cells of various diameters in 7-μm-filter zone. FIG. 24C is an example according to various embodiments illustrating showing a plot of cell compression force and hydrodynamic force of tumor cells of various diameters in 8-μm-filter zone. FIG. 24D is an example according to various embodiments illustrating showing a plot of cell compression force and hydrodynamic force of tumor cells of various diameters in 9-μm-filter zone. FIG. 24E is an example according to various embodiments illustrating showing a plot of cell compression force and hydrodynamic force of tumor cells of various diameters in 10-μm-filter zone. In each filter zone, cells with different sizes (from 10 μm to 20 μm) are considered.

The hydrodynamic force the CTC experiences under different infusion flow rates is compared with the compression force calculated using Equation 5 (FIG. 24A, FIG. 24B, FIG. 24C, FIG. 24D, and FIG. 24E). To guarantee CTCs not squeezing through the filter, a sufficiently low hydrodynamic force is necessary. This is achieved by optimizing the numbers of filters in each column and reducing background pressure through cutting filter columns. Hydrodynamic forces under different flow rates were simulated in COMSOL. Compression forces were calculated based on the Hertz model. The comparison of the compression force and hydrodynamic force of a WBC is also given in (A).

Due to the heterogeneity in the size of CTCs, filtration alone cannot capture all CTCs. The integration with immunoaffinity capture is essentially a 'double check' for CTC isolation. Supposing a cell is fully compressed into the filter and ignoring the friction effect, the hydrodynamic force cannot exceed the bond force between antibodies and the cell in order to retain the cell. The hydrodynamic force the cell experiences is simulated in COMSOL (FIG. 25A, FIG. 25B, and FIG. 25C). FIG. 25A is an example according to various embodiments illustrating velocity distribution in a 7-μm filter when a cell is fully compressed. FIG. 25B is an example according to various embodiments illustrating the viscous stress distribution around the cell. FIG. 25C is an example according to various embodiments illustrating a comparison between the bond force and hydrodynamic force a cell experiences at a flow rate of 3.6 ml/h. Bond forces for both MCF7 cells and L3.6pl cells are provided. The bond force is more than 10 times higher than the hydrodynamic force. The bond force is defined as the sum of all conjugation forces between antibodies and receptors on the cell. The contact area is denoted as $A_{contact}$, given as $$A_{contact} = 2\pi\left(\frac{D_{contact}}{2}\right)^2 \quad (6)$$

$D_{contact}$ is the diameter of the contact (7) area (FIG. 23E). It is calculated from[10]

$$D_{contact} = \sqrt{D_{deformed}^2 - W_{deformed}^2}$$

$D_{deformed}$ is the cell diameter after deformation. It is estimated as [11] (8)

$$D_{deformed} \approx \left(\frac{2D_{cell}^3}{3W_{deformed}} + \frac{W_{deformed}^2}{3}\right)^{1/2}$$

Take a MCF7 cell as an example, the antibody-antigen bond density is 29.71±2.66 bonds/μm²; anti-EpCAM/EpCAM bond strength is 6.7×10⁻⁶ dyne. [11] Consider a cell compressed into a 7-μm filter, the contact area of the cell with a diameter ranging from 10 to 20 μm is calculated as 49.1 to 572.7 μm². Assuming evenly distribution of antibody-antigen bonds, the bond force experienced by the cell is 195.6-2280.2 nN, which is more than 10 times higher than the hydrodynamic force the cell experiences (FIG. 25C). The comparison between the bond force and hydrodynamic force confirms the effectiveness of immunocapture in LFAM.

L3.6pl cells are a type of pancreatic cancer cells. Results obtained according to various embodiments show that L3.6pl cells and BxPC3 cells (another cell line of pancreatic cancer) express similar level of EpCAM. [5] It is reported that there are around 2800 antibody-antigen bonds per cell for BxPC3 cells. [12] Using this number, it was estimated that L3.6pl cells have a bond density of 37.8 bonds/μm². The corresponding bond force L3.6pl cells experience is 248.9-2901.1 nN.

Cell Counting Using CellProfiler

CellProfiler, a free open-source software for measuring and analyzing cell images, was used for the enumeration of cells (L3.6pl cells, MCF7 cells, or WBCs) captured as discussed in the literature. [13] As discussed above, each LFAM device was fully scanned to collect fluorescence signals of cells using the CCD camera. A cell counting script (pipeline) was built in CellProfiler which was amenable for auto processing of a large number of images. For each LFAM device, several sample images were chosen to be processed with the pipeline and compared with manually counting to ensure the accuracy. Briefly, the sample images were first uploaded to the pipeline.

Figure 26:
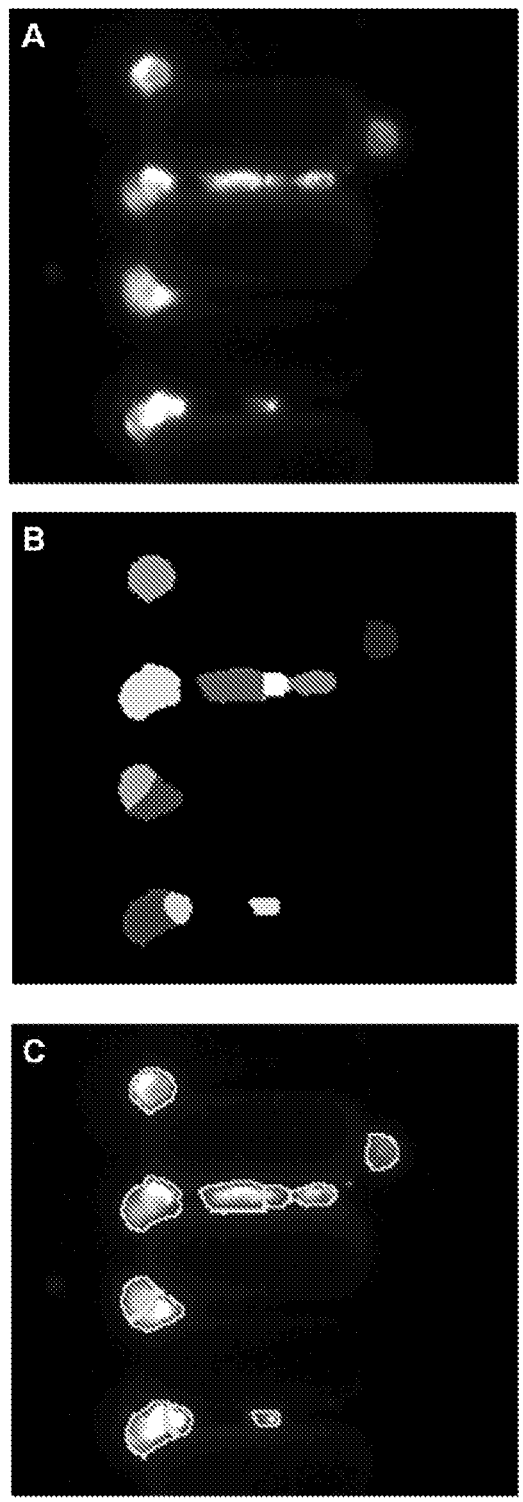
FIG. 26A: is an example according to various embodiments illustrating a sample image of fluorescence signals of cells in a LAFM device using a CCD camera for cell enumeration.
FIG. 26B: is an example according to various embodiments illustrating a sample image of tumor cells in LFAM device detected by CellProfiler.
FIG. 26C: is an example according to various embodiments illustrating a sample image of detected tumor cells in the LFAM device declumped by CellProfiler.

FIG. 26A is an example according to various embodiments illustrating a sample image of a scanned LFAM device to collect fluorescence signals of cells using a CCD camera for cell enumeration. FIG. 26B is an example according to various embodiments illustrating a sample image of a scanned LFAM device to collect fluorescence signals of cells using a CCD camera for cell enumeration. FIG. 26C is an example according to various embodiments illustrating a sample image of a scanned LFAM device to collect fluorescence signals of cells using a CCD camera for cell enumeration, including cell boundaries drawn by Cell-Profiler. Cells were identified based on intensity (FIG. 26B). Clumped cells were distinguished from one another by intensity gradient (FIG. 26C). Intensity threshold was manually tuned to remove background. The difference between results of cell counting given by Cellprofiler and those by manually enumeration are less than 5%.

L3.6pl Cells in Different Filter Zones

As discussed in the main text, L3.6pl cells are captured in different filter zones of LFAM. In general, bigger and more rigid cells are captured in larger filters (e.g., 10-μm-filter) while smaller cells are captured in smaller filters. FIGS. 27A-27E shows some representative images of L3.6pl cells captured in each filter zones of LFAM without antibody functionalization.

FIG. 27A is an example according to various embodiments illustrating an images of L3.6pl cells captured in a 10-μm-filter zone. FIG. 27B is an example according to various embodiments illustrating an images of L3.6pl cells captured in a 9-μm-filter zone. FIG. 27C is an example according to various embodiments illustrating an images of L3.6pl cells captured in a 8-μm-filter zone. FIG. 27D is an example according to various embodiments illustrating an images of L3.6pl cells captured in a 7-μm-filter zone. FIG. 27E is an example according to various embodiments illustrating an images of L3.6pl cells captured in a 6-μm-filter zone.

Capture of MCF7 Cells in LFAM

Besides L3.6pl cells discussed in the main text, MCF7 cells were also used to test the performance of LFAM. FIG. 28A is an example according to various embodiments illustrating a comparison of MCF7 cells captured in LFAM with and without antibody. As shown in FIG. 28A, at various flow rates, the capture efficiency of MCF7 cells ranges from 56.0±2.7% to 82.3±4.4% in LFAM without antibody. The capture efficiency may be from 63.4±2.8% to 92.1±0.8% in LFAM with antibody. The increase in capture efficiency due to the antibody presence may be around 10%. Compared with L3.6pl cells, the capture efficiency of MCF7 cells is slightly lower. The possible reason is that L3.6pl cells are generally more rigid[14,15] and express more EpCAM than MCF7 cells. [5, 16] FIG. 28B is an example according to various embodiments illustrating MCF7 cell distribution pattern in LFAM without antibody. Without antibody, fewer MCF7 cells are captured in the 10-μm-filter zone near the inlet when infusion flow rate increases, as shown in FIG. 28B. FIG. 28C is an example according to various embodiments illustrating MCF7 cell distribution pattern in LFAM with antibody. With antibody, the captured cells distribution patterns are almost identical for different flow rates as given in FIG. 28C. This is in accordance with the distribution pattern that was observed for L3.6pl cells as shown in FIG. 18B-C.

FIG. 17A, FIG. 17B, and FIG. 17C shows images of MCF7 cells captured in LFAM without antibody. FIG. 17A is an example according to various embodiments illustrating captured MCF7 cells in the LFAM chip at 100× magnification. The scale bar in FIG. 17A is 200 μm. FIG. 17B is an example according to various embodiments illustrating captured MCF7 cells in the LFAM chip at 200× magnification. The scale bar in FIG. 17B is 100 μm. FIG. 17C is an example according to various embodiments illustrating captured MCF7 cells in the LFAM chip at 400× magnification. The scale bar in FIG. 17C is 20 μm. Note that LFAM is not coated with antibody, thus no bond force will hold the captured cells in place. At the end of the experiment, the pumping force is stopped and the back pressure abruptly drops. As a result, a small percentage of cells detach from the filter and flow back to the main channel as observed in FIG. 17A, FIG. 17B, and FIG. 17C. Possible flow perturbation in the device during the motion of the microscope stage (with the device) could also cause cell detachment from the filters.

Capture Efficiency Comparison Among Different Types of Tumor Cells in LFAM

Figure 29A:
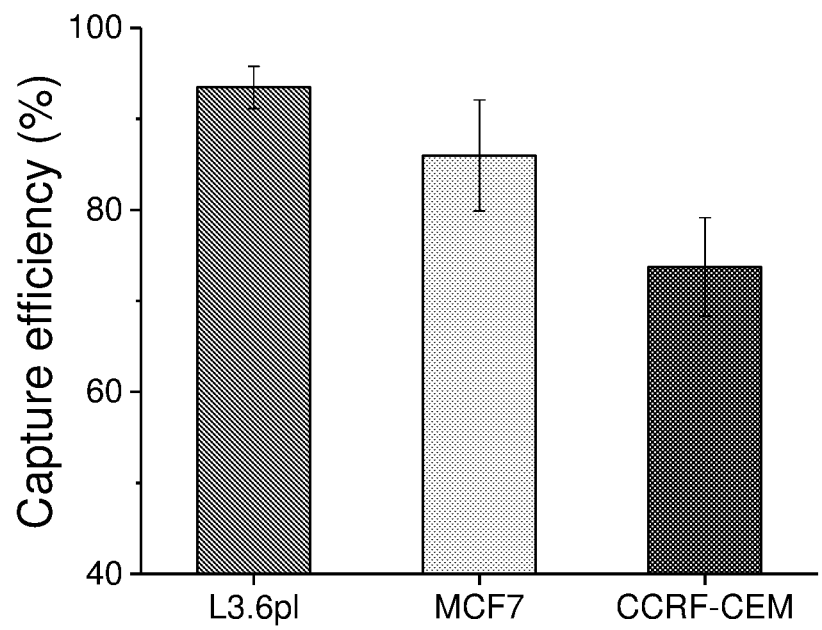
FIG. 29A: is an example according to various embodiments illustrating a capture efficiency comparison among L3.6pl, MCF7, and CCRF-CEM cells in the antibody-functionalized LFAM.

Cells with different sizes and EpCAM expression level were used to test the efficiency of the antibody-functionalized LFAM. L3.6pl cells (high EpCAM expression; diameter: 15.9±3.1 μm), MCF7 cells (medium EpCAM expression; diameter: 16.1±2.5 μm), CCRF-CEM cells (acute lymphoblastic leukemia cells with no EpCAM expression; diameter: 12.9±2.3 μm) were infused to antibody-functionalized LFAM devices. The infusion flow rate was 3.6 ml/h. FIG. 29A is an example according to various embodiments illustrating a capture efficiency comparison among L3.6pl, MCF7, and CCRF-CEM cells in the antibody-functionalized LFAM. More specifically, FIG. 29A shows capture efficiency of the three types of tumor cells. The capture efficiency of L3.6pl cells is 93.5±2.3%. The capture efficiency of MCF7 cells is 86.0±6.1%, which is lower than L3.6pl cell due to lower EpCAM expression level. The size of MCF7 cells and L3.6pl cell are similar. The capture efficiency of CCRF-CEM cells is 73.7±5.4%, which is the lowest since CCRF-CEM cells don't express EpCAM and their sizes are slightly smaller than MCF7 cells and L3.6pl cell.

Comparison Between LFAM and GEM

Figure 29B:
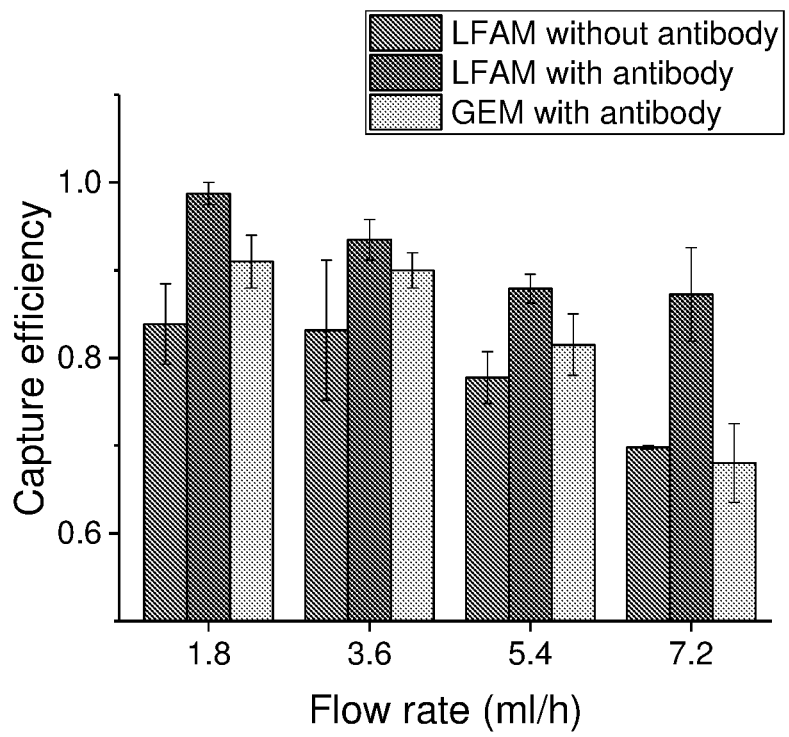
FIG. 29B: is an example according to various embodiments illustrating a comparison of L3.6pl cells capture efficiency among LFAM without antibody, LFAM with antibody, and GEM with antibody.

The performance of LFAM was compared with a GEM device that contains herringbone mixers. [5] Noting that the L3.6pl cell capture efficiency in GEM under different infusion flow rates has been published, the results from previous work are used here for comparison. [5] FIG. 29B is an example according to various embodiments illustrating a comparison of L3.6pl cells capture efficiency among LFAM without antibody, LFAM with antibody, and GEM with antibody. As shown in FIG. 29B, the antibody-functionalized LFAM produces higher capture efficiency than the antibody-functionalized GEM in all flow rates tested. At an infusion flow rate of 7.2 ml/h, the capture efficiency in the antibody-functionalized LFAM (87.2%) is 19.2% higher than the antibody-functionalized GEM (68.0%). On the other hand, LFAM without antibody gives similar capture efficiency with the antibody-functionalized GEM at 7.2 ml/h. The results indicate that integrating filtration with immunoaffinity-based capture is more advantageous at a high flow rate when filtration or immunocapture has low capture efficiency by itself.

Culture of Tumor Cells Isolated

The released L3.6pl cells were captured in LFAM with antibody and released as discussed in Experimental Procedure. They were then cultured in full growth medium.

FIGS. 30A-30C The growth of L3.6pl cells at different time points after being released from LFAM. The scale bar is 100 μm. FIG. 30A is an example according to various embodiments illustrating a photograph of a culture of L3.6pl cells on day 2 after release. FIG. 30B is an example according to various embodiments illustrating a photograph of a culture of L3.6pl cells on day 9 after release. FIG. 30C is an example according to various embodiments illustrating a photograph of a culture of L3.6pl cells on day 14 after release.

Tumor Cells Spiked in Blood

L3.6pl cells were spiked in 1 mL of 2-time-diluted healthy blood at different concentrations and then infused to the antibody-functionalized LFAM at 3.6 ml/h and 7.2 ml/h, as given in FIG. 20A. FIG. 20A is an example according to various embodiments illustrating a calibration curve of L3.6pl cells spiked in 2-time-diluted blood and infused to an antibody-functionalized LFAM. The flow rates are 3.6 ml/h and 7.2 ml/h.

CTCs in Clinical Samples

Figure 31:
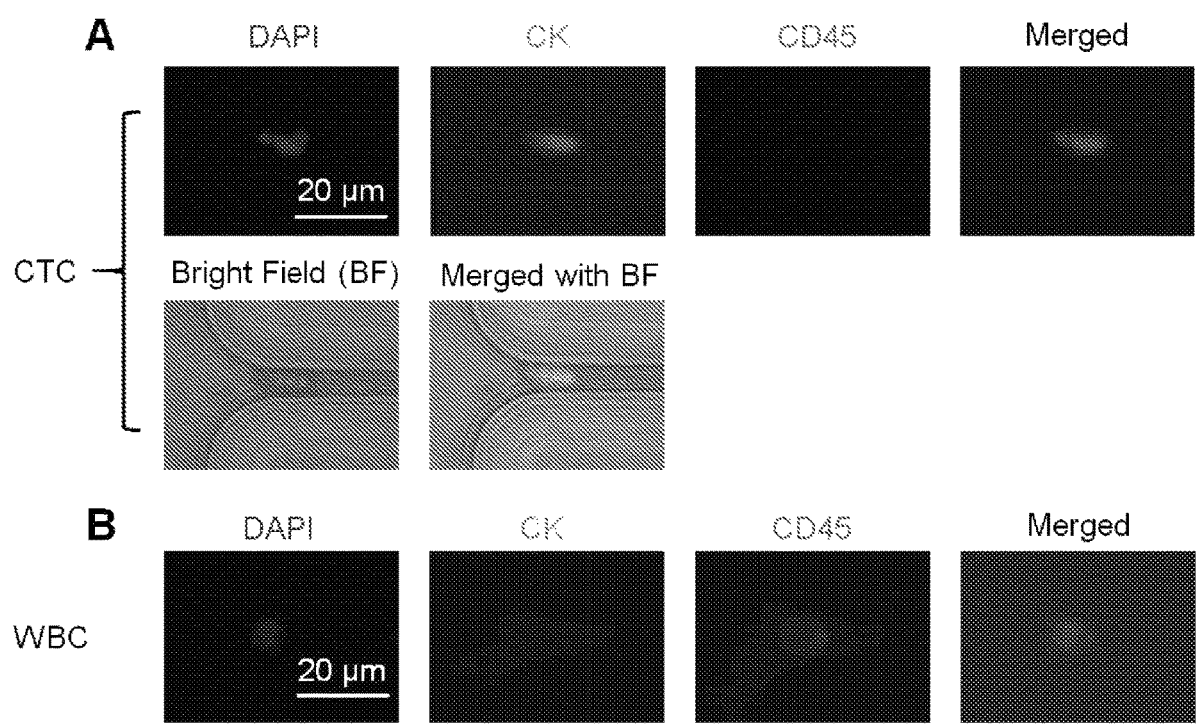
FIG. 31A: is an example according to various embodiments illustrating a CTC in a lateral filter of the antibody-functionalized LFAM.
FIG. 31B: is an example according to various embodiments illustrating a WBC nonspecifically captured in the lateral filter.

Clinical samples were collected from patients with metastatic colorectal cancers. The samples were divided into two portions. One was processed using the antibody-functionalized LFAM and the other portion was processed using antibody-functionalized GEM. Table S1 lists CTC counts in clinical samples by using either LFAM or GEM. The results show LFAM isolates more CTCs than GEM in nearly all cases. FIG. 31A is an example according to various embodiments illustrating a CTC in a lateral filter of the antibody-functionalized LFAM. The scale bar is 20 μm. FIG. 31B is an example according to various embodiments illustrating a WBC nonspecifically captured in the lateral filter. The scale bar is 20 μm. FIGS. 31A-31B show pictures of a CTC (DAPI+, CD45−, CK+) captured in the antibody-functionalized LFAM and a non-specifically captured WBC (DAPI+, CD45+, CK−) in the antibody-functionalized LFAM.

interference of normal blood cells. Therefore, CTC isolation in such LFAM devices does not require RBCs removal. Herein, the design and characterization of the LFAM is given. The flow pattern in the LFAM device was designed to maximize the interaction between cells and antibodies on filters. A fluid-solid interaction (FSI) model was developed to analyze the hydrodynamic force tumor cells experience to ensure active immunoaffinity-based cell capture. Different cell lines were used to test the performance of the device. Cultured tumor cells were spiked in diluted whole blood and infused to the antibody functionalized LFAM device to simulate CTC isolation. Eventually, the LFAM device was used for CTC isolation from blood samples of patients with metastatic pancreatic cancer.

Experimental Section

Fabrication of LFAM

The channel pattern of the LFAM device, according to one embodiment, was first sketched using AutoCAD. The CAD file was the sent out to a company (CAD/Art Services, Inc. OR) for transparency film printing. A dark field transparency film containing the channel pattern was obtained and taped on a 4×4 in$^2$ glass plate to make a photomask. A silicon master with complimentary feature was fabricated based on the pattern on the photomask using photolithography. A negative photoresist SU8 2025 photoresist was used for photolithography. Base on the silicon master, a PDMS substrate was fabricated using soft lithography. The PDMS

TABLE 1 provides information for the clinical samples.

| Sample No. | Patient No. | Date | Time (Blood Drawn) | Time (Sample Infusion) | Cancer type | CTCs ml$^{-1}$ by LFAM | CTCs ml$^{-1}$ by GEM |
|---|---|---|---|---|---|---|---|
| 1 | CTC001 | Aug. 15, 2018 | 15:19 | 17:00 | Colorectal | 2.25 | 0.5 |
| 2 | CTC003 | Sep. 10, 2018 | 11:52 | 12:50 | Colorectal | 5.5 | 1 |
| 3 | CTC004 | Sep. 10, 2018 | 12:57 | 15:10 | Colorectal | 3 | 1.75 |
| 4 | CTC006 | Sep. 19, 2018 | 11:50 | 13:42 | Colorectal | 4.5 | 4 |
| 5 | CTC009 | Oct. 19, 2018 | 10:42 | 11:41 | Colorectal | 8.25 | 4 |
| 6 | CTC005 | Nov. 13, 2018 | 9:30 | 12:00 | Colorectal | 1.5 | 0.5 |
| 7 | CTC008 | Nov. 13, 2018 | 11:30 | 13:25 | Colorectal | 1.75 | 0.5 |
| 8 | CTC011 | Nov. 15, 2018 | 10:00 | 12:40 | Colorectal | 1 | 0 |
| 9 | CTC018 | Nov. 20, 2018 | 10:30 | 13:00 | Colorectal | 2.5 | 2.75 |
| 10 | CTC022 | Nov. 26, 2018 | 10:30 | 12:30 | Colorectal | 1.75 | 1 |
| 11 | CTC020 | Nov. 29, 2018 | 10:30 | 12:30 | Colorectal | 5.25 | 1 |
| 12 | CTC023 | Nov. 29, 2018 | 11:30 | 14:30 | Colorectal | 6.25 | 1.25 |

Example 5

Various embodiments relate to a lateral filter array microfluidic (LFAM) device that combines size-based CTC isolation and immunoaffinity-based CTC isolation. Lateral filters with size of 6-10 μm were used to trap CTCs. Filters functionalized with antibodies gave higher tumor cell capture efficiency than filters without antibodies. However, the role of filters for immunoaffinity-based cell capture was unclear, especially the effect of filter size on immunocapture.

Other embodiments relate to a lateral filter array microfluidic device to study filter-like microfeatures for enhanced immunoaffinity CTC isolation. In this device, filters are either bigger or close to the size of CTCs. Instead of trapping CTCs, filters work as gates to prevent clumped cells from passing through and increase the probability of direct contact between tumor cells and antibodies immobilized on the surface of the filters. The antibody-antigen interaction is significantly enhanced due to the effective exclusion of substrate was bonded with a microscope slide after 5 minutes of UV Ozone treatment. The fabricated PDMS substrate of the LFAM device is shown in FIGS. 11A and 11B.

Cell Culture

L3.6pl cells (metastatic human pancreatic cancer cells) were obtained from Dr. Jose Trevino (Department of Surgery, University of Florida). MCF7 (human breast adenocarcinoma cells) cells were provided by Dr. Carlos Rinaldi (Department of Chemical Engineering, University of Florida) which were originally purchased from American Type Culture Collection (ATCC). CCRF-CEM cells (acute lymphoblastic leukemia cells) were purchased from ATCC. The L3.6pl cells and MCF7 cells were cultured in DMEM medium (ATCC) supplemented with 10% fetal bovine serum (FBS, GIBCO) and 100 units/mL penicillin-streptomycin (Cellgro, Manassas, Va.). The CCRF-CEM cells were cultured in RPMI1640 medium (ATCC) with 10% FBS and 100 units/mL penicillin-streptomycin. Different cell lines were cultured at 37° C. with 5% $CO_2$.

FIG. 2A, and FIG. 2B Illustration of filter-enhanced immunoaffinity based CTC isolation compared with traditional CTC isolation. Left: the capture efficiency can be reduced in a traditional device when a CTC is surrounded by a big number of normal blood cells. Right: filters force direct contacted between antibodies in the device and antigens on the tumor cell, while preventing the interference of normal blood cells. FIG. 1B Illustration of the antibody functionalized LFAM device. The serpentine main channel is incorporated with an array of filters, producing a two-dimensional flow to prevent cells from clogging. Antibodies are immobilized in the inner face of the channel for CTC capture. The LFAM device was mounted to a 3D printed fixture. The inset on the left illustrates the term "column" which includes filters and the channel elbow. The inset on the right shows the dimension of the serpentine main channel and filters.

Cell Sample Preparation

L3.6pl cells and MCF7 cells are adherent cells. The cells were first trypsinazed by 0.25% trypsin-EDTA for 10 minutes and then neutralized by full growth medium. The detached cells were later rinsed with Dulbecco's phosphate-buffered saline (DPBS) twice to remove impurities. Finally, the cells were resuspended in 1 mL of DPBS. CCRF-CEM cells are floating cells. For cell sample preparation, the cells were simply withdrawn from the flask and rinsed with DPBS twice and resuspended in 1 mL of DPBS. Vybrant fluorescence dyes were used for cell labeling. The dye was added to the suspended cells at 7 µL per $10^6$ cells and incubated for 20 minutes at 37° C. Afterwards, the cells were rinsed with DPBS for 3 times and resuspended in DPBS.

Device Preparation

An LFAM was first wetted by 99% ethanol and washed with 300 µL of DPBS. Then 100 µL of 1 mg/mL avidin was infused to LFAM and incubated for 10 minutes. Avidin was immobilized through physical adsorption. Following DPBS washing, 100 µL of 10 µg/mL biotinylated anti-Epithelial cell adhesion molecules (EpCAM) were introduced to LFAM and incubated for 10 minutes. Anti-EpCAM was immobilized in the device by avidin-biotin binding. The LFAM device was then washed and passivated with 300 µL of DPBS containing 1% bovine serum albumin (BSA).

Spiked Sample

Fluorescence labeled cells were diluted and spiked in DPBS buffer or diluted blood sample. The sample was then loaded in a syringe. The syringe was fixed in a syringe pump and connected to the LFAM device through tubing. The sample was infused to the antibody functionalized LFAM device by syringe pumping. A rotating magnetic bar was put in the syringe to agitate the sample during infusion to prevent cells from settling in the syringe. After sample infusion, DPBS was infused to LFAM to wash away leftover impurities.

Clinical Sample

Blood samples from patients with metastatic pancreatic cancer were obtained from the University of Florida Healthcare Cancer Center. The samples were collected in BD Vacutainers containing anti-coagulant sodium heparin. All samples were processed within 5 hours after collection. LFAM was compared with a previously reported geometrically enhanced mixing (GEM) chip. A total of 2-4 mL of whole blood was processed by each device.

For LFAM, two methods were used for blood treatment. The first method is simply diluting the whole blood with an equal volume of DPBS. The second method is the application of Ficoll-Paque following the manufacture's protocol. First, 2-4 mL of whole blood was mixed with equal amount of DPBS, and then added to a 50 mL-centrifugal tube with 8 mL of Ficoll Paque in it. The sample was then centrifuged at 800*g for 30 minutes to separate red blood cells and nucleated cells. The plasma, buffy coat and the majority of the Ficoll Paque layer were extracted and added to a new 15 mL-tube. The extracted substance was centrifuged again at 200*g for 10 minutes and supernatant was removed afterwards. The nucleated cells were then resuspended at 1 mL of DPBS. For the GEM chip, the second blood pretreatment method was used.

The sample was infused to the anti-EpCAM functionalized device (LFAM or GEM) at 1 µL/s. After washing with DPBS, 100 µL of 4% paraformaldehyde was infused to the device and incubated for 10 minutes for fixation. After washing with 200 µL of DPBS, 100 µL of 0.2% Triton X-100 was introduced and incubated for another 10 minutes for cell permeabilization. After washing with DPBS, a cocktail of fluorescence dye including 60 µL of 500 nM DAPI (4',6-diamidino-2-phenylindole), 10 µL of 10 µg/mL anti-cytokeratin-FITC, 10 µL of 10 µg/mL anti-CD45-PE, was introduced and incubated for 25 minutes for captured cells labeling. The device was washed with 500 µL of DPBS after cells labeling. Captured cells were enumerated under the fluorescence microscope, Olympus IX71 microscope. CTCs were detected as DAPI+, CK+, CD45−, while white blood cells were detected as DAPI+, CK−, CD45+. Triple positive cells were considered as false positive signals that may come from impurities.

Results and Discussion

Design of LFAM

For affinity-based CTC isolation, direct contact between CTCs and antibody immobilized inner surface of the microfluidic is required. However, the interaction between antigens on a CTC and antibodies in the device can be diminished when the CTC is surrounded by large amounts of normal blood cells (FIG. 2A).

An LFAM device, according to an embodiment, was used to combine filtration and immunoaffinity-based tumor cell capture. Enlighted by the strong interaction between CTCs and the device during filtration, filter-like features were applied to force the interaction between CTCs and the antibody functionalized device. An array of obstacles was employed to constitute a serpentine main channel (FIG. 11C). There are narrow gaps between neighboring obstacles which are considered "filters". As shown in FIG. 2B right, the filter size is designed to be similar to the size of a CTC. When entering the filter, the flow is regulated so that a single CTC can cross the filter more easily. This prevents the CTC from being entangled by other blood cells, thus significantly increasing the direct contact between the CTC and antibodies in the device. To prevent cells from clogging, a serpentine main channel is designed between different columns of filters, as given in FIG. 1B. When a cell flows through the LFAM device, it has two velocity components along both the main channel direction and the filter direction. Additionally, the wider main channel reduces the overall hydrodynamic resistance of the device.

As given in FIG. 11C, the LFAM device includes four serpentine main channels. The width of the main channel is W=300 µm. An array of filters are incorporated in the serpentine main channel. The filter size is defined by the smallest width of the gap ($W_1$). The filters are designed to be approximately 'wedge shape' with a wider opening in the entrance to decrease cell deformation.[17] The depth of the main channel and filters are 40 µm. The filters in the microchannel can be divided into 11 zones based on filter size with each zone including 10 columns of filters. There are 68 filters within each column. Near inlet, the filter width is $W_1=23.8$ μm. The filter width between neighboring zones decreases by about 1.1 μm. The smallest filter width is 12.3 μm. The length of each filter is $L_1=50$ μm. The distance between two adjacent filters is $W_2=58$ μm.

Flow Pattern in the LFAM

The LFAM device included filters with a significantly bigger size. Therefore, the flow pattern may be different than other embodiments. A theoretical model was developed to characterize the flow pattern in the LFAM device. The microchannel is modeled as a network of hydrodynamic resistors.

Figure 32:
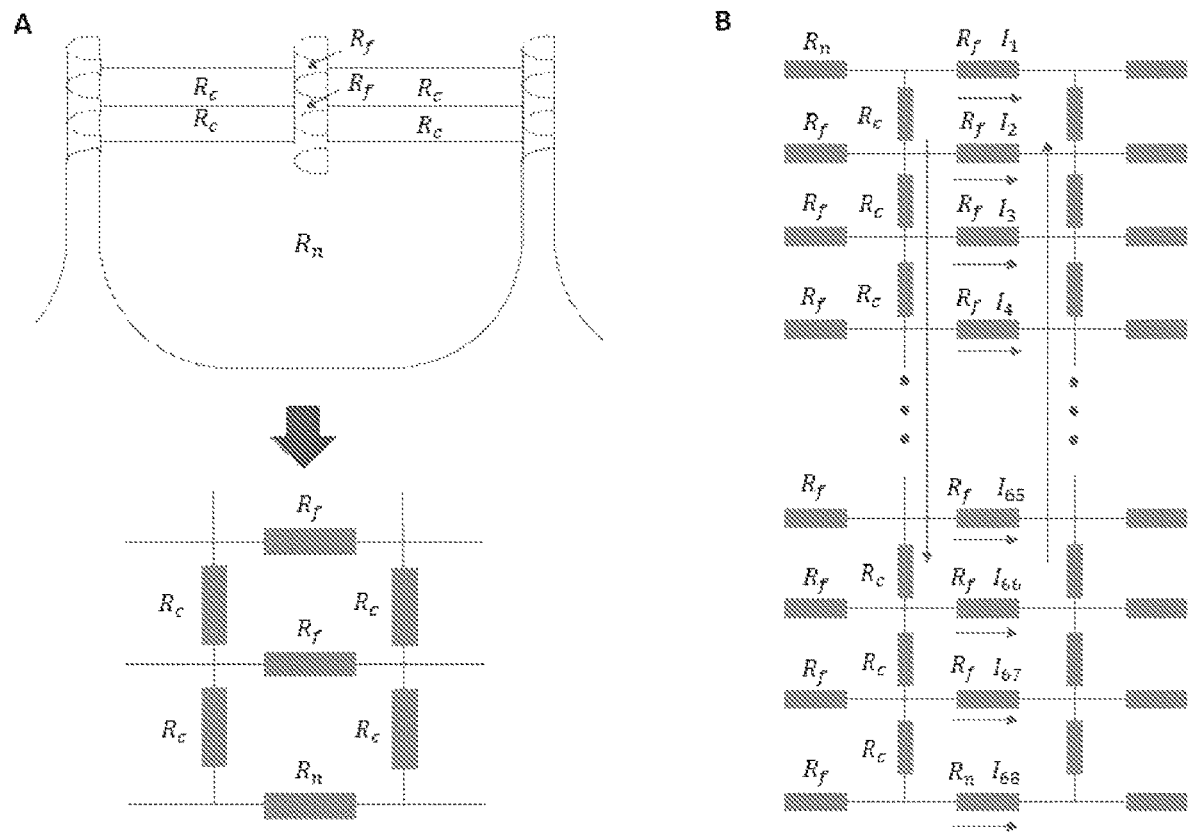
FIG. 32A: is an example according to various embodiments illustrating the combination of serpentine channel filters are modeled as a hydrodynamic resistor network.
FIG. 32B: is an example according to various embodiments illustrating the three basic components are interconnected in the hydrodynamic resistor network.

FIG. 32A is an example according to various embodiments illustrating the combination of serpentine channel filters are modeled as a hydrodynamic resistor network. The filters ($R_f$) in the same column are modeled as a group of paralleled hydrodynamic resistors. The serpentine main channel are modeled as a series of hydrodynamic resistors including main channel sections ($R_c$) and channel elbows ($R_n$). As shown in FIG. 32A, the network includes three basic components. $R_f$ is the hydrodynamic resistance of a filter. The serpentine main channel is considered as a series of hydrodynamic resistors. $R_c$ is the hydrodynamic resistance of a section of the main channel between adjacent filters. $R_n$ is the paralleled hydrodynamic resistance of the channel elbow and its adjacent filter. Since the hydrodynamic resistance of the elbow is much smaller than the filter. $R_n$ can be estimated by the hydrodynamic resistance of the channel elbow.

FIG. 32B is an example according to various embodiments illustrating the three basic components are interconnected in the hydrodynamic resistor network. The filters and the channel elbows in adjacent columns are distributed in a reversed order. As shown in FIG. 32B, the flow rate through Filter-k is denoted as $I_k$. Since channel elbow is in paralleled with the filters, the flow rate denotation is also applicable for the channel elbow and it is denoted as $I_{68}$. Considering the total flow through the whole microchannel as I, using the Kirchhoff's current law (KCL):

$$I_1+I_2+ \ldots +I_{68}=1 \quad (1)$$

FIG. 32B shows that filters and channel elbow in the neighboring columns are distributed in a reversed order. Therefore, the flow rates in the neighboring columns are also distributed in a reversed order. The pressure difference along a certain filter $\Delta P_k=I_k R_f$. Using the Kirchhoff's voltage law (KVL):

$$2R_c(I_{68}-I_1)+(I_2-I_1)R_f=0$$

$$2R_c(I_{67}+I_{68}-I_1-I_2)+(I_3-I_2)R_f=0$$

$$\ldots$$

$$2R_c(I_{67}+I_{68}-I_1-I_2)+(I_{67}-I_{66})R_f=0$$

$$2R_c(I_{68}-I_1)+I_{68}R_n-I_{67}R_f=0 \quad (2)$$

Using KCL and KVL, flow rate in each filter and channel elbow can be calculated. The mainstream is defined as the flow through the channel elbow ($I_{68}$). The total flow is defined as the flow through the whole column (I). The mainstream ratio is defined as the ratio of flow rate in the mainstream to the total flow rate ($I_{68}$/I). The mainstream ratio largely determine the layout of the flow pattern in LFAM and subsequently affect the interaction between cells and filters.

Using the theoretical model, the flow rates distribution in the same column of filters and the channel elbow in the LFAM device was calculated. The infused flow rate to one serpentine main channel was set as 0.25 μL/s. FIG. 10A is an example according to various embodiments illustrating the main channel flow ratio for different filter sizes. For different filter sizes from 12.3 μm to 23.8 μm, the mainstream ratio ranged from 6.0% to 14.9%, as given in FIG. 10A, showing that the majority of the flow (94.0% to 85.1%) is distributed in filters within a column. This is confirmed by experimental observation; FIG. 10C is an example according to various embodiments illustrating the flow pattern in the LFAM device. The filter size is 18.1 μm. The scale bar is 300 μm.

The flow rate and flow velocity distribution in the same column of filters and channel elbow for different filter sizes is given in FIG. 37A-37C. The flow rate in different filters including different filter sizes ranged from 0.0013 μL/s to 0.0053 μL/s. Correspondingly, the average velocity ranged from 2.4 mm/s to 13.2 mm/s.

Hydrodynamic Force Analysis

To ensure the LFAM device applicable for immunoaffinity-based cell capture, hydrodynamic force analysis may be necessary. It requires that the hydrodynamic force a cell experiences is smaller than the dislodge force needed to detach the cell from the filter. Hydrodynamic force analysis for cells by the filters were simulated COMSOL Multiphysics.

Incompressible flow was assumed in the microfluidic channel and the fluid flow was described by the Navier-Stokes Equation. A two dimensional (2D) fluidic dynamic simulation was applied to reduce computational demand. The motion and deformation of the cell was achieved by a time-dependent fluid-solid interaction (FSI) model. A linearly deformable moving mesh was created in the cell-flow interface where fluid pressure and viscous drag were imposed. The cell was considered as a solid domain with linear elasticity where solid mechanics was applied.

When the cell interacted with the filter, three conditions were considered: the cell size was smaller than the filter; the cell size was the same as the filter; the cell size was bigger than the filter. Without considering filtration effect (the external force added on the cell when the filter is smaller than the cell size), the hydrodynamic force the cell experiences should be smaller than the bond force caused by antibody-antigen bonds. Hydrodynamic force simulation for cells of different diameters captured in a 15-μm-filter at a flow rate of 1.0 L/s, is given in FIG. 33A-G.

Figure 33:
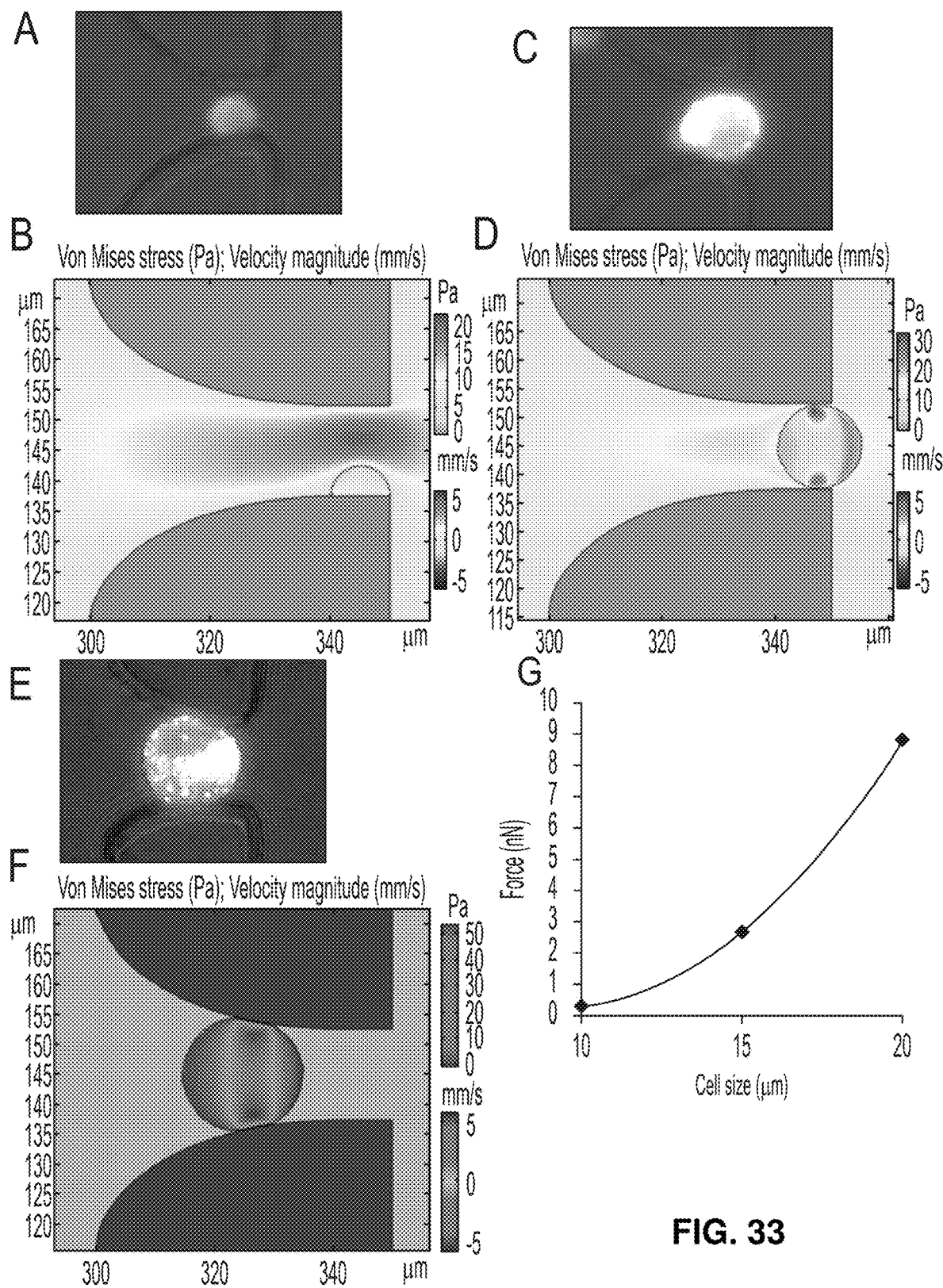
FIG. 33A: is an example according to various embodiments illustrating a photograph of a cell captured by the filter.
FIG. 33B: is an example according to various embodiments illustrating shear stress distribution on the surface the captured cell, shown in FIG. 33A, when the cell diameter is smaller than the filter.
FIG. 33C: is an example according to various embodiments illustrating a photograph of a cell captured by the filter.
FIG. 33D: is an example according to various embodiments illustrating shear stress distribution on the surface of the captured cell, shown in FIG. 33C, when the cell diameter is the same as the filter.
FIG. 33E: is an example according to various embodiments illustrating a photograph of a cell captured by a filter.
FIG. 33F: is an example according to various embodiments illustrating shear stress distribution on the captured cell, shown in FIG. 33E, when the cell diameter is bigger than the filter.
FIG. 33G: is an example according to various embodiments illustrating the hydrodynamic force the capture cell experiences depending on its size.

FIG. 33A is an example according to various embodiments illustrating a photograph of a cell captured by the filter. FIG. 33B is an example according to various embodiments illustrating shear stress distribution on the surface the captured cell, shown in FIG. 33A, when the cell diameter is smaller than the filter. FIG. 33C is an example according to various embodiments illustrating a photograph of a cell captured by the filter. FIG. 33D is an example according to various embodiments illustrating shear stress distribution on the surface of the captured cell, shown in FIG. 33C, when the cell diameter is the same as the filter. FIG. 33E is an example according to various embodiments illustrating a photograph of a cell captured by a filter. FIG. 33F is an example according to various embodiments illustrating shear stress distribution on the captured cell, shown in FIG. 33E, when the cell diameter is bigger than the filter. The hydrodynamic force analysis for the captured cells was performed using COMSOL Multiphysics. FIG. 33G is an example according to various embodiments illustrating the hydrodynamic force the capture cell experiences depending on its size. For the same flow rate and the same filter, the hydrodynamic force is positively related to the cell diameter.

From simulation, the hydrodynamic force a cell experiences is positively related to the surface area of the cell. The biggest simulated force here is 8.9 nN. The simulated hydrodynamic force is compared with the bond force the captured cell experienced. Take MCF7 cells (human breast adenocarcinoma cells) as an example, the literature gave the bond force at a scale of $10^2$~$10^4$ nN.[11] The simulation shows that the bond force the cell experiences is bigger than the hydrodynamic force by more than one order of magnitude. Therefore, the LFAM device is applicable for immunoaffinity based cell capture.

Cell Capture Pattern in the Microchannel

To explore the effect of filters on immunoaffinity capture, filters with different sizes were used in the device, according to various embodiments. At a given flow rate, flow velocity and shear rate are smaller in bigger filters, which is beneficial to cell capture. However, bigger filters cannot effectively exclude the interference of normal blood cells. To find out the best filter size for enhanced immunoaffinity capture, the cell capture pattern in the LFAM device was studied. L3.6pl cells and MCF7 cells were used. They are known to express plentiful of EpCAM antigens. About 10000 fluorescence labeled L3.6pl cells or MCF7 cells were infused to the device at different flow rates.

FIG. 34A is an example according to various embodiments illustrating captured MCF7 cell distribution in the LFAM device without antibody under different flow rates. FIG. 34B is an example according to various embodiments illustrating captured MCF7 cell distribution in the LFAM device with antibody under different flow rates. FIG. 34C is an example according to various embodiments illustrating captured L3.6pl cell distribution in the LFAM device without antibody under different flow rates. FIG. 34D is an example according to various embodiments illustrating captured L3.6pl cell distribution in the LFAM device with antibody under different flow rates. FIG. 34E is an example according to various embodiments illustrating L3.6pl cells captured in the LFAM device under different flow rates. FIG. 34F is an example according to various embodiments illustrating MCF7 cells captured in the LFAM device under different flow rates.

L3.6pl cells were 15.9±3.1 µm and MCF7 cells were 16.1±2.5 µm.[18] The capture ratio is defined as the ratio of the number of cells captured in a filter zone to the total number of cells captured in the LFAM device. FIGS. 34A and 34C show the capture pattern of L3.6pl cells and MCF7 cells in anti-EpCAM functionalized LFAM devices under different flow rates. Capture ratio in the front half of the microchannel (23.8 µm-filter zone to 18.1 µm-filter zone) decreases with increasing flow rates for both cell lines. The reason behind is that a higher flow rate produces a higher shear rate which makes it harder for tumor cells to be captured.[19] Therefore, it requires longer interaction distance for cells to slow down and be captured. Capture ratio in the front half of the microchannel for L3.6pl cells is generally higher than that for MCF7 cells. It is probably because L3.6pl cells express more EpCAM than MCF72 cells.[5, 16] While capture ratio in the back half of the microchannel (18.1 µm-filter zone to 12.3 µm-filter zone) increases as flow rate increases, capture picks can be observed in the region between the 18.1 µm-filter zone and 15.7 µm-filter zone at flow rates higher than 0.5 µL/s for both cell lines. Noting that these filters sizes and the measured diameters of the two types of cells are in the same range, it probably demonstrates that filters with size similar to the cell diameter give the best cell capture enhancement effect.

As comparison, the cell capture patterns in the device without anti-EpCAM were also studied. As shown in FIGS. 34B and 34D, for different flow rates, cells capture peaks are all located between the 15.7 µm-filter zone and 12.3 µm-filter zone where filter sizes are smaller than the cell sizes. It is coherent with the fact that filtration is predominant in the device without antibody functionalization.

Tumor cell capture efficiency was also studied in the LFAM device. Capture efficiency is defiend as the number of tumor cells captured in the LFAM device to the number of tumor cells spiked in the buffer. Without anti-EpCAM immobilization, the LFAM device brings low CTC capture efficiency (FIGS. 34E and 34F). Only 10-20% of both types of cells are captured even at a low flow rate of 0.5 µL/s. This is expected as the filter sizes are generally bigger than the cells. Though the smallest filter size is 12.3 µm, the channel height is 40 µm, which means cells only deform in the width direction. It's not difficult for a tumor cell to deform by ~23% in one-direction to pass the filter.[17] However, when the chip is functionalized with Anti-EpCAM, the capture efficiency increases dramatically. For L3.6pl cells, the capture efficiency is 91.3±3.0% at 0.5 µL/s; the corresponding capture efficiency for MCF7 cells is 87.2±4.7%. The significant improvement of cell capture capability demonstrates that affinity-based cell capture is predominated in the anti-EpCAM functionalized LFAM device.

Capture of Target Cells from A Cell Mixture

About 1000 L3.6pl cells (target) were spiked in CCRF-CEM cells (control) at a ratio of 1:20. The cell capture purity was defined as the number of captured target cells over the total cells enumerated in the LFAM device. FIG. 35A is an example according to various embodiments illustrating capture of target L3.6pl cells in the antibody-functionalized LFAM device from a population of cells at 0.5 µL/s and 1 µL/s. The target cell capture efficiency was 90.8±7.8% for 0.5 l/s and 88.2±5.2% for 1.0 pl/s. FIG. 35B is an example according to various embodiments illustrating capture of target L3.6pl cells purity in the antibody-functionalized LFAM device at 0.5 µL/s and 1 µL/s. At the same time, the purity increased from 49.5±6.7% to 57.5±1.2% as the flow rate increased from 0.5 l/s to 1.0 pl/s. The sorting purity shows that the control cells decreased by more than 95%.

Capture of Target Cells Spiked in Diluted Blood

To mimic CTC capture in clinical condition, 10 to 10,000 L3.6pl cells were spiked to 1 mL of 2-time diluted blood (whole blood:DPBS=1:1) and then infused to the anti-EpCAM functionalized LFAM device at 1.0 pl/s. FIG. 36A is an example according to various embodiments illustrating capture of target cells from diluted blood. Different amount of L3.6pl cells are spiked in mL of 2-time diluted blood sample and infused to the antibody functionalized LFAM device. The spiked versus captured L3.6pl cells calibration is given in FIG. 36A. The captured/spiked ratio maintains good linearity for different spike concentrations. The capture efficiency is as high as 93.5±0.5%.

Isolation of CTCs from Clinical Samples. The antibody functionalized LFAM devices were used for CTC isolation from blood samples of patients with metastatic pancreatic cancer. The clinical sample tests of the LFAM device were compared with an ongoing clinical study using Geometric Enhanced Micromixer (GEM) chip reported previously.[5] Clinical samples of 2~4 mL were first treated with Ficoll-Paque to separate red blood cells from nucleated cells. After red blood cells removal, the extracted nucleated cells were resuspended in 1 mL of DPBS. The nucleated cell sample was then processed with the anti-EpCAM immobilized LFAM device, according to various embodiments. When processing clinical sample with the LFAM device, the clinical study using the GEM chip was conducted separately. To eliminate false positive signals, only cytokeratin positive, CD45 negative, DAPI positive (CK+/CD45−/DAPI+) cells were considered as CTCs. White blood cells should be labeled as CK−/CD45+/DAPI+). Any other labeling formats were considered as false positive signals or cell debris. CTCs were detected in all 16 clinical samples using antibody functionalized LFAM device, ranging from 1 to 15 CTCs/ml. FIG. 36B is an example according to various embodiments illustrating CTCs per mL enumerated from the LFAM device and GEM chip from 16 clinical samples. As comparison the GEM chip detected CTCs ranging from 1-10 CTCs/ml as shown in FIG. 36B. FIG. 36C is an example according to various embodiments illustrating the average CTCs per mL in the LFAM device and the GEM device. As given in FIG. 36C, the average CTC number enumerated in the LFAM device is 4.7 CTCs/mL in LFAM devices while it is 3.4 CTCs/mL in GEM devices, showing that LFAM devices generally gave higher CTCs isolation efficiency compared with GEM chips.

To find out if LFAM is applicable for whole blood process, two blood pretreatments methods were used (Ficoll-Paque pretreatment and 2-time dilution) and the samples were processed by LFAM. FIG. 36D is an example according to various embodiments illustrating a comparison of different blood pretreatment methods using LFAM. FIG. 36D shows the comparison of CTC counts between the two pretreatment methods. Given the smaller number of data points, it is reluctant to conclude that using 2-time diluted whole blood gives better CTC capture efficiency. However, it is clear that antibody-functionalized LFAM is amenable for CTC isolation from 2-time diluted blood samples.

The size of captured CTC in LFAM device was also measured as shown in FIGS. 39A and 39B. Since most CTCs are not strictly circular, the maximum dimension and minimum dimension of CTCs are given. The maximum dimension of CTCs is 14.8±5.4 μm and the minimum dimension of CTCs is 10.9±3.5 μm.

Conclusion

A LFAM device according to various embodiments was developed in this work for highly efficient CTC isolation. The device includes serpentine main channels, wherein filters are incorporated. The serpentine main channel is designed to induce 2-dimensional flow and prevent cells from clogging filters. The filters effectively reduce the interference of non-target cells and force direct contact between target cells and antibodies on the filter surface. It was found that when the filter size is close to the target cell size, the effect on immunoaffinity capture is optimal. The antibody-functionalized LFAM device gives good purity when cell mixtured is introduced. Finally, the antibody functionalized device was applied for CTC isolation from blood of patients with metastatic pancreatic cancer. It gives better CTC capture efficiency compared with GEM chips.

Comparison of Different Immunoaffinity-Based CTC Isolation Methods

TABLE 2 shows a comparison of different immunoaffinity-based CTC isolation methods.

| Device | Capture efficiency | Purity | Throughput | Pretreatment | Reference |
|---|---|---|---|---|---|
| CTC-Chip | 60-80% | ~50% | 1-2 mL/h | Whole blood or Lysed blood | [20] |
| GEM chip | 88% | ~70% | 3.6 mL/h | Lysed blood | [5] |
| HB chip | ~90% | Higher than Ref. 1 | 1.2 mL/h | Whole blood | [21] |
| SINP | 45~65% | NA | ~1 mL/h | Whole blood | [22] |
| TiO2 | >45% | NA | 1 mL/h | Whole blood | [23] |
| This work | >90% | 50-60% | 3.6 mL/h | 2-time diluted blood or Ficoll Paque treated | |

Fabrication of the LFAM Device

As given in the main text, fabrication of the LFAM device included two steps: 1. Fabrication of a silicon master using photolithography. 2. Fabrication of the PDMS substrate using soft lithography.

The silicon master was fabricated based on the pattern on the photomask using photolithography. The silicon wafer was first soaked in 99+% acetone for 10 minutes to remove organic impurities. After washing with Isopropyl alcohol ($C_3H_8O$) and Deionized (DI) water, the silicon wafer was soaked in Piranha solution for 5 minutes to remove any organic or inorganic impurities. After washing with large amount of running DI water, the water was treated with buffered oxide etchant (BOE) for 30 seconds to remove silicon oxide. The silicon wafer was washed with DI water again and dried in an oven at 120° C. for 10 minutes. Before spin coating, the wafer was treated with bis(trimethylsilyl)amine (HMDS). A layer of SU8 2025 photoresist was spin coated on the silicon wafer. The thickness of the photoresist was about 40 μm controlled by spinning speed. The SU8 coated silicon wafer was then put on a hotplate for soft bake. The temperature increased from room temperature (20° C.) to 85° C. at a heating rate of 120° C./hour and maintained at 85° C. for 90 minutes. The dried silicon wafer was directly contacted with the photomask and exposed under UV light. The exposure dose was chosen under manufacture's instruction. The exposed SU8 photoresist polymerized under UV exposure and the pattern from the photomask was transferred to the SU8 photoresist. After UV exposure, the silicon wafer was heated on the hotplate at 95° C. for 10 minutes. Then the silicon wafer was developed for 8 minutes using SU8 developer to remove exposed photoresist. After development, the silicon wafer was put in the oven for hard bake at 120° C. for 20 minutes. Thermal cracks on the SU8 photoresist was removed after hard bake. The accurate thickness of the SU8 feature on the silicon master was measured using Dektak 150.

Base on the silicon master, a PDMS substrate was fabricated using soft lithography. An aluminum foil bowl was made with the silicon master in the bottom to hold PDMS. Fully mixed liquid state PDMS (base/curing agent=10:1) was casted on the silicon master. The PDMS loaded aluminum foil bowl was put in a vacuum chamber to remove bubbles from PDMS. The aluminum foil bowl was then cured in an over at 65° C. for at least 4 hours. PDMS was polymerized and formed a transparent elastic substrate after curing in the oven. The PDMS was then peeled off from the silicon master, trimmed to fit a microscope slide and punched holes at the inlet and outlet. The PDMS substrate and a glass microscope slide were treated with UV Ozone for 5 minutes and bonded to form the final LFAM device. FIGS. 11A and 11B shows images of the PDMS substrate under scanning electron microscope (SEM). The LFAM device under SEM. The images show the serpentine main channel and the arrangement of filters.

A theoretical model was developed to study the flow pattern in the microfluidic device. For laminar flow, pressure drop $\Delta P$ is proportional to flow rate Q using Stokes Law. In microfluidics, a microchannel can be modeled as a hydrodynamic resistance $R_h$, wherein $\Delta P = R_h Q$. The hydrodynamic resistors network is analogous to a circuit network, wherein the Kirchhoff's Laws are applicable.

The KCL and KVL given in the main text can be further arranged in a matrix form $$\begin{bmatrix} -2R_c - R_f & R_f & & & & & & 2R_c \\ -2R_c & -2R_c - R_f & R_f & & & & 2R_c & 2R_c \\ -2R_c & -2R_c & -2R_c - R_f & R_f & & 2R_c & 2R_c & 2R_c \\ -2R_c & -2R_c & -2R_c & -2R_c - R_f & R_f & 2R_c & 2R_c & 2R_c & 2R_c \\ & & & & \vdots & & & \\ -2R_c & -2R_c & & & & & -R_f 2R_c + R_f 2R_c & \\ -2R_c & & & & & & -R_f & 2R_c + R_n \\ 1 & 1 & 1 & 1 & 1 & & 1 & 1 \end{bmatrix} \begin{Bmatrix} I_1 \\ I_2 \\ I_3 \\ I_4 \\ \vdots \\ I_{66} \\ I_{67} \\ I_{68} \end{Bmatrix} = \begin{Bmatrix} 0 \\ 0 \\ 0 \\ 0 \\ \vdots \\ 0 \\ 0 \\ I \end{Bmatrix}$$

Using the matrix, the flow rate and average flow velocity in each filter and the channel elbow can be calculated.

Flow Rate and Flow Velocity Distribution.

FIG. 37A-37C gives the flow rate and flow velocity distribution in the same column of filters and channel elbow for different filter sizes. FIG. 37A is an example according to various embodiments illustrating a flow rate distribution in different filters in the same column as compared with flow rate in the channel elbow. FIG. 37B is an example according to various embodiments illustrating a flow velocity distribution in different filters in the same column as compared with flow velocity in the channel elbow. FIG. 37C is an example according to various embodiments illustrating a schematic diagram of the channel for which data is presented in FIG. 37A and FIG. 37B.

Simulation of Hydrodynamic Force

To ensure the device may be applicable for immunoaffinity based cell capture, hydrodynamic force analysis may be necessary for cells captured by the filters. Hydrodynamic force analysis for captured cells by the filters were simulated using a Fluid-Structure Interaction (FSI) model in COMSOL. The fluid flow is expressed by Navier-Stokes equation:

$$\rho \nabla \cdot V = 0 \quad (7)$$

$$\frac{\partial V}{\partial t} + \rho(V \cdot \nabla)V = \nabla \cdot [-p + \mu(\nabla V + (\nabla V)^T)] + F \quad (8)$$

where $\rho$ is fluid density; V is flow velocity; p is pressure; $\mu$ is dynamic viscosity; F is external force; p is the pressure. On the fluid-structure interface, the governing equations are given as $$V = V_W \quad (9)$$

$$V_w = \frac{\partial U_{solid}}{\partial t} \quad (10)$$

$$\sigma \cdot n = \nabla \cdot [-p + \mu(\nabla V + (\nabla V)^T)] \cdot n \quad (11)$$

where $V_w$ is the velocity of the moving cell. $U_{solid}$ is the displacement of the cell. $\sigma$ is the stress on the cell.

Size of CTCs Captured in the LFAM Device

Figure 38:
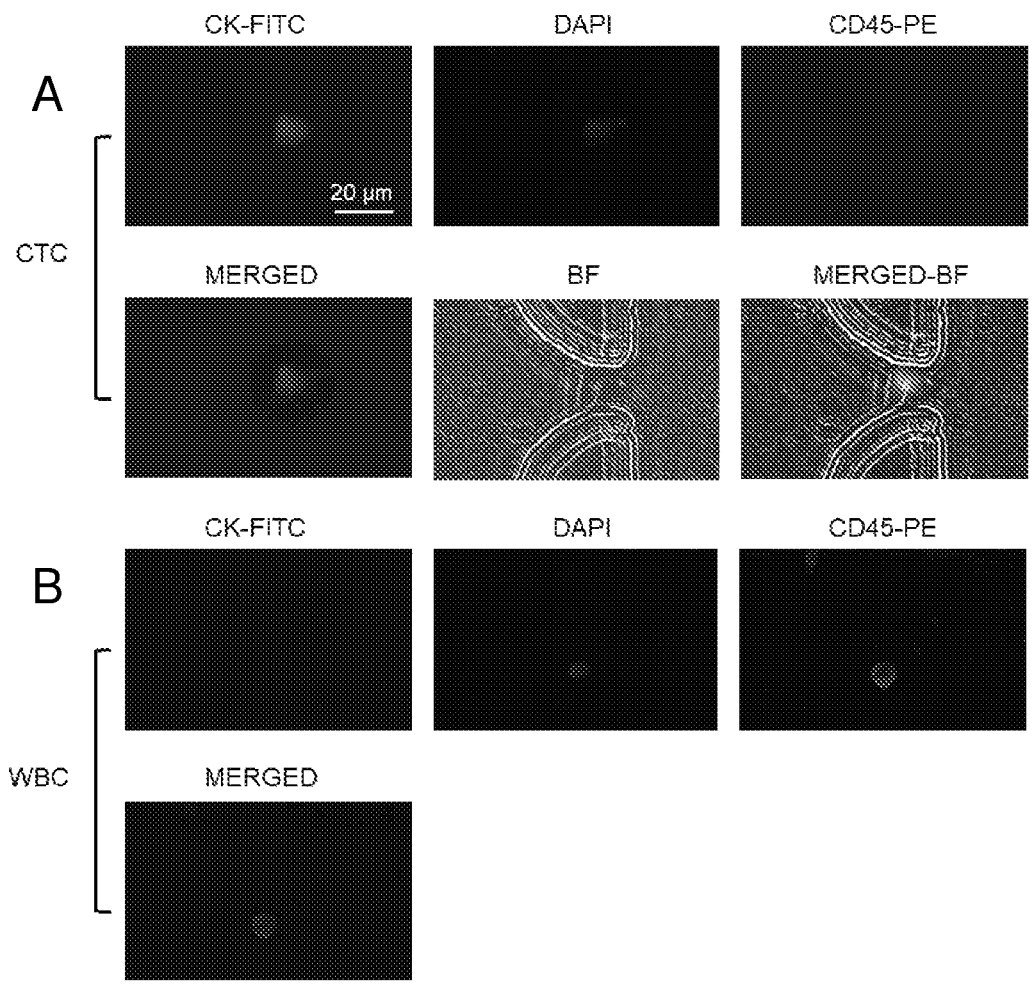

The sizes of captured CTCs in the LFAM device were measured using CellSens (Olympus, PA). Since CTCs are not exactly round, the maximum and minimum dimension of a CTC are measured. FIG. 38 shows a CTC and a white blood cell (WBC) in the LFAM device. FIGS. 39A and 39B give the distribution of maximum and minimum dimension of CTCs, with an average of 14.8 μm for maximum dimension and 10.9 μm for minimum dimension. FIG. 38A is an example according to various embodiments illustrating sample images of captured CTC (CK+/DAPI+/CD45−). FIG. 38B is an example according to various embodiments illustrating sample images of captured and nonspecific captured white blood cells WBC (CK−/DAPI+/CD45+).

FIG. 39A is an example according to various embodiments illustrating the distribution of minimum dimensions of CTCs measured by CellSens. FIG. 39B is an example according to various embodiments illustrating the distribution of maximum dimensions of CTCs measured by CellSens.

CONCLUSION

As a conclusion, integration of filtration and immunocapture can produce high CTC capture efficiency as it potentially isolate both rigid CTCs and CTCs with high biomarker expression levels. Various embodiments relate to LFAM devices involving an integration of filtration and immunocapture. The device flow pattern was simulated and optimized with the theoretical model. From the study of cell line capture in the anti-EpCAM-functionalized LFAM devices, it was found that added-up effect of filtration and immunocapture determines the cell capture capability of a filter device. Filters not only brings filtration effect, but also enhance immunocapture as they enforce direct interaction between biomarkers on the cells and antibody immobilized in the filters. The application of serpentine main channel produces two-dimensional flow in the LFAM device which prevents cells from clogging in the lateral filters and increases cell capture purity. It was found that the flow pattern in the LFAM device is adjustable through controlling the mainstream ratio and all cells can be forced to pass through filters. Overall, the antibody-functionalized LFAM device gives high capture efficiency and good purity, showing its great potential for clinical application.

All patents, patent applications, patent publications, technical publications, scientific publications, and other references referenced herein are hereby incorporated by reference in this application to the extent they are not inconsistent with the teachings herein. In particular, the following references are hereby incorporated by reference in their entirety.

REFERENCES

1. Karabacak, N. M., et al., Nature Protocols, 2014. 9(3): p. 694-710.
2. Ahmed, M. G., et al., Angewandte Chemie, 2017. 129 (36): p. 10821-10825.
3. Moon, H.-S., et al., Lab on a Chip, 2011. 11(6): p. 1118-1125.
4. Meunier, A., et al., Analytical Chemistry, 2016. 88(17): p. 8510-8517.
5. Sheng, W., et al., Lab on a Chip, 2014. 14(1): p. 89-98.
6. Zhang, W., et al., Proceedings of the National Academy of Sciences, 2012: p. 201209893.
7. Kuo, J. S., et al., Lab on a Chip, 2010. 10(7): p. 837-842.
8. Xu, L., et al., PLoS One, 2015. 10(9): p. e0138032.
9. Bruus, H., Lab on a Chip, 2011. 11(22): p. 3742-3751.
10. Lin, Y.-L., et al., Chemical Engineering Science, 2008. 63(1): p. 195-203.
11. Hu, S., et al., small, 2016. 12(17): p. 2300-2311.
12. Thege, F. I., et al., Lab on a Chip, 2014. 14(10): p. 1775-1784.
13. Carpenter, A. E., et al., Genome biology, 2006. 7(10): p. R100.
14. Rice, A., et al., Oncogenesis, 2017. 6(7): p. e352.
15. Dokukin, M. E., et al., Biophysical journal, 2013. 104(10): p. 2123-2131.
16. Kirpotin, D. B., et al., Cancer research, 2006. 66(13): p. 6732-6740.
17. McFaul, S. M., et al., Lab on a chip, 2012. 12(13): p. 2369-2376.
18. Chen, K., et al., Angew Chem Int Ed Engl, 2019.
19. Murlidhar, V., et al., Small, 2014. 10(23): p. 4895-904.
20. Nagrath, S., et al., Nature, 2007. 450(7173): p. 1235-9.
21. Stott, S. L., et al., Proceedings of the National Academy of Sciences, 2010. 107(43): p. 18392-18397.
22. Wang, S., et al., Angewandte Chemie, 2009. 121(47): p. 9132-9135.
23. Zhang, N., et al., Advanced Materials, 2012. 24(20): p. 2756-2760.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A lateral filter array microfluidic device for capturing a target isolate in a liquid sample, the device comprising
   a substrate; and
   at least one series of boundaries associated with the substrate,
   wherein the at least one series of boundaries are arranged to define at least one serpentine main channel coupled with an inlet and an outlet that allows flow of the liquid sample in serpentine flow pattern, and
   wherein the at least one series of boundaries comprise a plurality of filters with apertures that connect two sections of the serpentine main channel thereby allowing lateral flow of the liquid sample between the two sections.

2. The lateral filter array microfluidic device according to claim 1, wherein a width of the at least one serpentine main channel is greater than a filter size of the filters.

3. The lateral filter array microfluidic device according to claim 1, wherein the at least one serpentine main channel has a width ranging from 3 um to 1000 um.

4. The lateral filter array microfluidic device according to claim 1, wherein a filter size of the plurality of filters is from about 0.03 um to about 100 um.

5. The lateral filter array microfluidic device according to claim 1, wherein at least one boundary of the at least one series of boundaries is formed by one or more filter support structures having a height ranging from 3 um to 100 um.

6. The lateral filter array microfluidic device according to claim 1, wherein the target isolate is a cell or cell component, extracellular vesicle, exosome, virus, bacterium, or particle.

7. The lateral filter array microfluidic device according to claim 1, wherein at least one series of boundaries comprises two or more series of boundaries that each defines a separate serpentine main channel.

8. The lateral filter array microfluidic device according to claim 1, wherein at least one boundary of the at least one series of boundaries is functionalized to comprise a binding molecule having an affinity to the target isolate.

9. The lateral filter array microfluidic device according to claim 8, wherein the binding molecule comprises an antibody, an aptamer, multiple antibodies, multiple aptamers, or combinations thereof.

10. The lateral filter array microfluidic device according to claim 8, wherein the binding molecule is attached to one or more of the plurality of filters.

11. The lateral filter array microfluidic device according to claim 8, wherein the binding molecule is attached adjacent to apertures and on walls of the serpentine main channel of the device.

12. The lateral filter array microfluidic device according to claim 1, wherein the target isolate is a cell.

13. The lateral filter array microfluidic device according to claim 12, wherein the cell is a circulating tumor cell (CTC) or other rare cells.

14. The lateral fluid microfluidic device according to claim 1, wherein the series of boundaries comprises a first boundary comprising filters of a first filter size and a second boundary comprising a filters of a second filter size, wherein the first filter size and second filter size are different.

15. The lateral fluid microfluidic device according to claim 14, wherein the first boundary is closer to the inlet and the second boundary is closer to the outlet and wherein the first filter size is greater than the second filter size.

16. The lateral fluid microfluidic device according to claim 14, further comprising a third boundary having filters of a third filter size and a fourth boundary having filters of a fourth filter size, wherein the third filter size is smaller than the second filter size, and the fourth filter size is smaller than the third filter size.

17. The lateral fluid microfluidic device according to claim 1, further comprising a cover over the boundaries.

18. The lateral fluid microfluidic device according to claim 17, wherein the cover is a glass slide and the substrate is PDMS.

19. The lateral fluid microfluidic device according to claim 1, where the device is comprised of thermoplastic material, silicon or glass, adhesive tapes, thin films, or a combination thereof.

20. The lateral fluid microfluidic device according to claim 19, wherein the thermoplastic material comprises cyclic olefin copolymer (COC), poly(methyl methacrylate) (PMMA), polycarbonate (PC), polystyrene, polyester, polypropylene, polyurethane, acrylonitrile butadiene styrene (ABS), polylactic acid (PLA), and polytetrafluoroethylene (PTFE).

21. A method of capturing a target isolate in a liquid sample comprising applying the liquid sample to an inlet of a lateral flow microfluidic device according to claim 1; and
asserting a force to direct flow of the liquid sample along the serpentine main channel and laterally through filters in the series of boundaries, wherein the target isolate is captured at one or more of the filters.

22. The method according to claim 21, wherein the filters comprise a binding molecule having affinity for the target isolate.

23. The method of any according to claim 22, wherein the binding molecule is an antibody, aptamer, multiple antibodies, multiple aptamers, and combinations thereof.

24. The method according to claim 21, wherein the target isolate a particle, virus, bacterium, extracellular vesicle, exosome, cell or cell component.

25. The method of according to claim 24, wherein the target isolate is a circulating tumor cell.

26. The method according to claim 25, wherein the cell is a rare cell.

* * * * *